(12) United States Patent
Urry et al.

(10) Patent No.: US 6,533,819 B1
(45) Date of Patent: Mar. 18, 2003

(54) INJECTABLE IMPLANTS FOR TISSUE AUGMENTATION AND RESTORATION

(75) Inventors: Dan W. Urry, Birmingham, AL (US); Timothy M. Parker, Odenville, AL (US); Paul A. Glazer, Brookline, MA (US)

(73) Assignee: Bioelastics Research, Ltd., Birmingham, AL (US)

( * ) Notice: Subject to any disclaimer, the term of this patent is extended or adjusted under 35 U.S.C. 154(b) by 0 days.

(21) Appl. No.: 09/841,334

(22) Filed: Apr. 23, 2001

Related U.S. Application Data

(63) Continuation of application No. 09/258,723, filed on Feb. 26, 1999, now abandoned.
(60) Provisional application No. 60/076,297, filed on Feb. 27, 1998, and provisional application No. 60/087,155, filed on May 29, 1998.

(51) Int. Cl.[7] .................................................. A61F 2/44
(52) U.S. Cl. .................................................. 623/17.16
(58) Field of Search ........................... 623/16.11, 17.11, 623/17.12, 17.13; 128/898

(56) References Cited

U.S. PATENT DOCUMENTS

| | | |
|---|---|---|
| 4,870,055 A | 9/1989 | Urry et al. |
| 4,898,926 A | 2/1990 | Urry |
| 4,976,734 A | 12/1990 | Urry et al. |
| 5,226,292 A | 7/1993 | Urry |
| 5,250,516 A | 10/1993 | Urry |
| 5,336,256 A | 8/1994 | Urry |
| 5,428,022 A | 6/1995 | Palefsky et al. |
| 5,476,666 A | 12/1995 | Rhee et al. |
| 5,510,121 A | 4/1996 | Rhee et al. |
| 5,527,610 A | 6/1996 | Urry |
| 6,166,130 A * | 12/2000 | Rhee et al. .................. 525/54.1 |
| 6,264,695 B1 * | 7/2001 | Stoy .......................... 623/17.16 |
| 6,280,475 B1 * | 8/2001 | Bao et al. .................. 623/17.16 |
| 6,352,557 B1 * | 3/2002 | Ferree ....................... 623/17.11 |

FOREIGN PATENT DOCUMENTS

WO     WO 95/26761 A1     10/1995

OTHER PUBLICATIONS

Appell, Rodney A., "Collagen Injection Therapy for Urinary Incontinence", *The Craft of Urologic Surgery*, vol. 21(1), pp. 177–182 (1994).
Blaivas, Jerry G. and Jacobs, Ben Z., "Pubovaginal Fascial Sling for the Treatment of Complicated Stress Urinary Incontinence". *J. Urol.*, vol. 145, pp. 1214–1218 (1991).
Canning, Douglas A., "New Implants for Endoscopic Correction in the Nineties and Beyond", *Dial. Ped. Urol.*, vol. 14 (1991).
Frank, David H., et al. "Human Antibody Response Following Multiple Injections of Bovine Collagen", *Plastic and Reconstructive Surgery*, vol. 87, pp. 1080–1088 (1991).
Herschorn, et al., Followup of Intraurethral Collagen for Female Stress Urinary Incontinence, *J. Urol.*, vol. 156, pp. 1305–1309 (1996).
Kagan, Herbert M. et al., "Repeat Polypeptide Models of Elastin as Substrates for Lysly Oxidase" *J. Biol. Chem.*, vol. 255, pp. 3656–3659 (1980).
Malizia, et al., "Migration and Granulomatous Reaction After Periurethral Injection of Poytef (Teflon)", *JAMA*, vol. 251, pp. 3277–3281 (1984).
Murless, J., "The Injection Treatment of Stress Incontinence", *J. Obste. Gynaecol.*, vol. 45, pp. 67–73 (1938).
Nicol, Alastair, et al. "Cell Adhesive Properties of Bioelastic Materials Containing Cell Attachment Sequences", *Biot. and Bioactive Polymers*, Plenum Press, New York, pp. 95–113 (1994).
Nicol, Alastair, et al., "Cell Adhesion and Growth on Synthetic Elastomeric Matrices Containing ARG–GL-Y–ASP–SER–$^3$", *J. Biomed. Mat. Res.*, vol. 26; pp. 393–413 (1992).
Quackels, R., "Deux Incontinences Apres Adenomectomie Gueries Par Injection de Paraffine Dans le Perinee" *Acta. Urol. Belg.*, vol. 23, pp. 259–262 (1955).
Richardson, Thomas D., et al., "Endoscopic Injection of Glutaraldehyde Cross–Linked Collagen for the treatment of Intrinsic Sphincter Deficiency in Women", *Adult Urology*, vol. 46, pp. 378–381 (1995).
Santarosa, Richard P. and Blaivas, Jerry G., "Periurethral Injection of Autologous Fat for the Treatment of Sphincteric Incontinence", *J. Urol.*, vol. 151, pp. 607–611 (1994).
Siegle, Ronald, J., et al., "Intradermal Implantation of Bovine Collagen", *Arch. Dermatol.*, vol. 120, pp. 183–187 (1984).
Stricker, Phillip and Haylen Bernard, "Injectable Collagen for Type 3 Female Stress Incontinence: the First 50 Australian Patients", *The Medical Journal of Australia*, vol. 158, pp. 89–91 (1993).
Urry, Dan W., *Angew. Chem. Omt. Ed. Engl.*, vol. 32, pp. 819–841 (1993).

(List continued on next page.)

*Primary Examiner*—Corrine McDermott
*Assistant Examiner*—Hieu Phan
(74) *Attorney, Agent, or Firm*—Cooley Godward LLP; Richard L. Neeley; Shelley P. Eberle

(57) ABSTRACT

A method for tissue augmentation in a mammal is provided having injecting a polymer at a tissue site in need of augmentation and having a tissue temperature, the polymer having repeating peptide monomeric units selected from the group consisting of nonapeptide, pentapeptide and tetrapeptide monomeric units, wherein the monomeric units form a series of β-turns separated by dynamic bridging segments suspended between the β-turns, wherein the polymer has an inverse temperature transition $T_t$ less than the tissue temperature, and wherein the polymer is injected as a water solution at coacervate concentration in the substantial absence of additional water. A kit containing the injectable bioelastic polymer and a syringe is also provided.

30 Claims, 6 Drawing Sheets

OTHER PUBLICATIONS

Urry, Dan W., et al., "Medical Application of Bioelastice materials", Reprinted from *Biotechnological Polymers: Medical, Pharmaceutical and Industrial Applications*, pp. 82–103 (1993).

Urry, Dan W., et al., "Elastic Protein–Based Polymers in Soft Tissue Augmentation and Generation", *J. Biomater. Sci. Polymer Edn.*, vol. 9, No. 10, pp. 1015–1048 (1998).

Urry, Dan W., "Bioelastic Materials as Matrices for Tissue Reconstruction", *Tissue Engineering Current Perspectives*, (Eugene Bell, Ed.,) Birkhauser Boston, Div. Springer–Verlag, New York, Ny, pp. 199–206 (1993).

Walker, R. Dixon, et al., "Injectable Bioglass as a Potential Substitute for Injectable Polytetrafluoroethylene" *J. Urol.*, vol. 148, pp. 645–647 (1992).

* cited by examiner

```
gaggatccgaagacaacaGGTGGCGTGTTCCGGGGGCGTACCG                    (SEQ ID NO:1)
  BamH1            GlyGlyValValProGlyGlyGlyValPro              (SEQ ID NO:9)

GGTGGCGTACCGGGCGGTTTCCCGGGAGGTGTGCCG
                   GlyGlyValProGlyGlyPheProGlyGlyValPro

GGTGGGGTTCCAGGCGGTGTACCGGGTGGGGTTTCCG
                   GlyGlyValProGlyGlyValProGlyGlyPhePro

GGCGGTGTTCCGGGTGGAGTTCCGGGTGGCGTGCCG
                   GlyGlyValProGlyGlyValProGlyGlyValPro

GGCGGTTTTCCAggaagtcttcggatccag
                   GlyGlyPhePro    Bbs1     BamH1
```

FIGURE 1

```
           G    V    G    V    G    P    G    V    P
ggcgttggatccag   GGC  GTT  GGG  GTA  CCG  GGT  GTT  GGC  GTA  CCG     (SEQ ID NO:10)
 Pf1M1 BamH1    Pf1M1

G    K    G    V    P    G    V    P    G    V    P
           GGT  AAA  GGT  GTC  CCG  GGC  GTT  GGT  GTG  CCG

G    V    G    F    P    G    F    P    G    F    P
           GGT  GTA  GGC  TTT  CCG  GGC  TTC  GGA  TTC  CCA gaggatcca                                                    (SEQ ID NO:2)
            BamH1
```

```
       (Pf1M1)           Kpn1              Hinf1 (Pf1M1)
            TAGGGGTACCGGGTCGTGGTGACTCTCCGGGCG       (SEQ ID NO:3)
            CGCATCCCCATGGCCCAGCACCACTGAGAGGCC       (SEQ ID NO:4)
             V  G  V  P  G  R  G  D  S  P  G       (SEQ ID NO:11)
```

FIGURE 4

```
gaggatcca        G  V  G  V  G  V  P  G  V  G  V  P
BamH1          GGC GTT GGG GTA CCG GGT GTT GGC GTA CCG
               Pf1M1

G  V  G  V  G  V  P  G  V  G  V  P
               GGT GTT GGT GTC CCG GGC AAA GGT GTC CCG

G  V  G  V  G  V  P  G  V  G  V  P     (SEQ ID NO:12)
               GGT GTA GGC GTT CCG GGT GTG GGA GTC CCA  (SEQ ID NO:5)

ggcgttggatcc
               Pf1M1  BamH1
```

```
        G   V   G   V   P   G   V   G   V   P
       GGC GTT GGT GTA CCG GGT GTT GGT GTG CCG

G   V   G   V   P   G   V   G   V   P
       GGT GTT GGT GTT CCG GGC GTA GGC GTA CCG

G   V   G   V   P   G   V   G   V   P
       GGC GTA GGC GTG CCG GGC GTA GGC GTT CCG

G   V   G   V   P   G   V   G   V   P
       GGC GTG GGC GTA CCG GGC GTG GGC GTG CCG

G   V   G   V   P   G   V   G   V   P
       GGT GTG GGC GTC CCG GGT GTA GGT GTT CCA

G   V   G   V   P   G   R   G   D   S   P
       GGC GTA GGG GTA CCG GGT CGT GGT GAC TCT CCG

G   V   G   V   P   G   V   G   V   P
       GGC GTT GGT GTA CCG GGT GTT GGT GTG CCG

G   V   G   V   P   G   V   G   V   P
       GGT GTT GGT GTT CCG GGC GTA GGC GTA CCG

G   V   G   V   P   G   V   G   V   P
       GGC GTA GGC GTG CCG GGC GTA GGC GTT CCG

G   V   G   V   P   G   V   G   V   P
       GGC GTG GGC GTA CCG GGC GTG GGC GTG CCG

G   V   G   V   P   G   V   G   V   P     (SEQ ID NO:13)
       GGT GTG GGC GTC CCG GGT GTA GGT GTT CCA
```

(SEQ ID NO:13)

Ggcgttggatcc                                                        (SEQ ID NO:6)

FIGURE 5

```
            G   V   G   V   P   G   V   G   V   P
  ggatcca  GGC GTT GGT GTA CCG GGT GTT GGT GTG CCG G   V   G   V   P   G   V   G   V   P
           GGT GTT GGT GTT CCG GGC GTA GGC GTA CCG G   V   G   V   P   G   V   G   V   P
           GGC GTA GGC GTG CCG GGC GTA GGC GTT CCG G   V   G   V   P   G   V   G   V   P
           GGC GTG GGC GTA CCG GGC GTG GGC GTG CCG G   V   G   V   P   G   V   G   V   P
           GGT GTG GGC GTC CCA GGT GTA GGC GTT CCG G   V   G   V   A   P   G   V   G   V   A   P
           GGT GTG GGT GTA GCT CCG GGT GTT GGC GTT GCA CCG G   V   G   V   A   P   G   V   G   V   A   P
           GGC GTA GGT GTT GCT CCG GGC GTT GGC GTG GCG CCG G   V   G   V   A   P   G   V   G   V   A   P
           GGT GTT GGT GTT GCT CCG GGT GTA GGC GTT GCT CCG G   V   G   V   A   P   G   V   G   V   A   P
           GGC GTT GGT GTT GCC CCA GGT GTA GGT GTG GCA CCG G   V   G   V   P   G   V   G   V   P
           GGC GTT GGT GTA CCG GGT GTT GGT GTG CCG G   V   G   V   P   G   V   G   V   P
           GGT GTT GGT GTT CCG GGC GTA GGC GTA CCG G   V   G   V   P   G   V   G   V   P
           GGC GTA GGC GTG CCG GGC GTA GGC GTT CCG G   V   G   V   P   G   V   G   V   P
           GGC GTG GGC GTA CCG GGC GTG GGC GTG CCG G   V   G   V   P   G   V   G   V   P    (SEQ ID NO:14)
           GGT GTG GGC GTC CCG GGT GTA GGT GTT CCA ggcgttggatcc                                        (SEQ ID NO:7)

Pf1M1    BamH1
```

FIGURE 6

```
          G   V   G   P   G   V   G   P   G   V   G   P   G   V   P
gaggatcca GGC GTT GGG CCG GGT GTT GGC GTA CCG GGC GTA CCG                    (SEQ ID NO:15)
BamH1     Pf1M1

G   V   G   P   G   V   G   P   E   G   V   G   V   P
          GGT GTT GGT GTC CCG GGC GAA GGT GTG CCG

G   V   G   P   G   V   G   V   P
          GGT GTA GGC GTT CCG GGT GTG GGA GTC CCA
```

```
ggcgttggatcc                                                                  (SEQ ID NO:8)
Pf1M1 BamH1
```

FIGURE 7

5' adapter
(SEQ ID NO:30)

```
                                                      3' adapter
                                                     (SEQ ID NO:31)
   BamH1   Nco1                                                      Hind3   EcoR1   BamH1
CTGGATCCAGACCATGGGCG       TT---GGCG  TTGGTGTACCGTAAGCTTGAATTCGGATCCAG
GACCTAGGTCTGGTACC          CGCAA---C  CGCAACCACATGGCATTCGAACTTAAGCCTAGGTC
                                                                              (SEQ ID NO:33)
     (SEQ ID NO:32)
     Met       [ (GVGVP)₁₀ ]ₙ                         V  G  V  P  stop
```

FIGURE 8

SEQUENCE LISTING

<160> NUMBER OF SEQ ID NOS: 65

<210> SEQ ID NO 1
<211> LENGTH: 180
<212> TYPE: DNA
<213> ORGANISM: Artificial Sequence
<220> FEATURE:
<221> NAME/KEY: misc_feature
<222> LOCATION: (1)..(180)
<223> OTHER INFORMATION: Synthetic

<400> SEQUENCE: 1

```
gaggatccga agacaacagg tggtgttccg ggcggcgtac cgggtggcgt accgggcggt      60
ttcccgggag gtgtgccggg tggggttcca ggcggtgtac cgggtgggtt tccggcggt     120 gttccgggtg gagttccggg tggcgtgccg ggcggttttc caggaagtct tcggatccag    180
```

<210> SEQ ID NO 2
<211> LENGTH: 113
<212> TYPE: DNA
<213> ORGANISM: Artificial Sequence
<220> FEATURE:
<221> NAME/KEY: misc_feature
<222> LOCATION: (1)..(113)
<223> OTHER INFORMATION: Synthetic

<400> SEQUENCE: 2

| gaggatccag gcgttggggt accgggtgtt ggcgtaccgg gtaaaggtgt cccgggcgtt | 60 |
| ggtgtgccgg gtgtaggctt tccgggtttc ggattcccag gcgttggatc cag | 113 |

<210> SEQ ID NO 3
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Synthetic

<400> SEQUENCE: 3

| tagggtacc gggtcgtggt gactctccgg gcg | 33 |

<210> SEQ ID NO 4
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: Synthetic

<400> SEQUENCE: 4

| cgcatcccca tggcccagca ccactgagag gcc | 33 |

<210> SEQ ID NO 5
<211> LENGTH: 111
<212> TYPE: DNA
<213> ORGANISM: Artificial Sequence
<220> FEATURE:
<221> NAME/KEY: misc_feature
<222> LOCATION: (1)..(111)
<223> OTHER INFORMATION: Synthetic

<400> SEQUENCE: 5

| gaggatccag gcgttggggt accgggtgtt ggcgtaccgg gtgttggtgt cccgggcaaa | 60 |
| ggtgtgccgg gtgtaggcgt tccgggtgtg ggagtcccag gcgttggatc c | 111 |

<210> SEQ ID NO 6
<211> LENGTH: 345
<212> TYPE: DNA
<213> ORGANISM: Artificial Sequence
<220> FEATURE:
<221> NAME/KEY: misc_feature
<222> LOCATION: (1)..(345)
<223> OTHER INFORMATION: Synthetic

<400> SEQUENCE: 6

| ggcgttggtg taccgggtgt tggtgtgccg ggtgttggtg ttccgggcgt aggcgtaccg | 60 |
| ggcgtaggcg tgccgggcgt aggcgttccg ggcgtgggcg taccgggcgt gggcgtgccg | 120 |
| ggtgtgggcg tccgggtgt aggtgttcca ggcgtagggg taccgggtcg tggtgactct | 180 |
| ccgggcgttg gtgtaccggg tgttggtgtg ccgggtgttg gtgttccggg cgtaggcgta | 240 |
| ccgggcgtag gcgtgccggg cgtaggcgtt ccgggcgtgg gcgtaccggg cgtgggcgtg | 300 |
| ccgggtgtgg gcgtcccggg tgtaggtgtt ccaggcgttg gatcc | 345 |

<210> SEQ ID NO 7
<211> LENGTH: 463
<212> TYPE: DNA

-continued

<213> ORGANISM: Artificial Sequence
<220> FEATURE:
<221> NAME/KEY: misc_feature
<222> LOCATION: (1)..(463)
<223> OTHER INFORMATION: Synthetic

<400> SEQUENCE: 7
ggatccaggc gttggtgtac cgggtgttgg tgtgccgggt gttggtgttc cgggcgtagg    60
cgtaccgggc gtaggcgtgc cgggcgtagg cgttccgggc gtgggcgtac cgggcgtggg   120
cgtgccgggt gtgggcgtcc caggtgtagg cgttccgggt gtgggtgtag ctccgggtgt   180
tggcgttgca ccgggcgtag gtgttgctcc gggcgttggc gtggcgccgg gtgttggtgt   240
tgctccgggt gtaggcgttg ctccgggcgt tggtgttgcc ccaggtgtag gtgtggcacc   300
gggcgttggt gtaccgggtg ttggtgtgcc gggtgttggt gttccgggcg taggcgtacc   360
gggcgtaggc gtgccgggcg taggcgttcc gggcgtgggc gtaccgggcg tgggcgtgcc   420
gggtgtgggc gtcccgggtg taggtgttcc aggcgttgga tcc                     463

<210> SEQ ID NO 8
<211> LENGTH: 111
<212> TYPE: DNA
<213> ORGANISM: Artificial Sequence
<220> FEATURE:
<221> NAME/KEY: misc_feature
<222> LOCATION: (1)..(111)
<223> OTHER INFORMATION: Synthetic

<400> SEQUENCE: 8
gaggatccag gcgttggggt accgggtgtt ggcgtaccgg gtgaaggtgt cccgggcgtt    60
ggtgtgccgg gtgtaggcgt tccgggtgtg ggagtcccag gcgttggatc c            111

<210> SEQ ID NO 9
<211> LENGTH: 48
<212> TYPE: PRT
<213> ORGANISM: Artificial Sequence
<220> FEATURE:
<221> NAME/KEY: PEPTIDE
<222> LOCATION: (1)..(48)
<223> OTHER INFORMATION: Synthetic

<400> SEQUENCE: 9

Gly Gly Val Pro Gly Gly Val Pro Gly Gly Val Pro Gly Gly Phe Pro
1               5                  10                  15

Gly Gly Val Pro Gly Gly Val Pro Gly Gly Val Pro Gly Gly Phe Pro
            20                  25                  30

Gly Gly Val Pro Gly Gly Val Pro Gly Gly Val Pro Gly Gly Phe Pro
        35                  40                  45

<210> SEQ ID NO 10
<211> LENGTH: 30
<212> TYPE: PRT
<213> ORGANISM: Artificial Sequence
<220> FEATURE:
<221> NAME/KEY: PEPTIDE
<222> LOCATION: (1)..(30)
<223> OTHER INFORMATION: Synthetic

<400> SEQUENCE: 10

Gly Val Gly Val Pro Gly Val Gly Val Pro Gly Lys Gly Val Pro Gly
1               5                  10                  15

Val Gly Val Pro Gly Val Gly Phe Pro Gly Phe Gly Phe Pro
            20                  25                  30

```
<210> SEQ ID NO 11
<211> LENGTH: 11
<212> TYPE: PRT
<213> ORGANISM: Artificial Sequence
<220> FEATURE:
<221> NAME/KEY: PEPTIDE
<222> LOCATION: (1)..(11)
<223> OTHER INFORMATION: Synthetic

<400> SEQUENCE: 11

Val Gly Val Pro Gly Arg Gly Asp Ser Pro Gly
1               5                   10

<210> SEQ ID NO 12
<211> LENGTH: 30
<212> TYPE: PRT
<213> ORGANISM: Artificial Sequence
<220> FEATURE:
<221> NAME/KEY: PEPTIDE
<222> LOCATION: (1)..(30)
<223> OTHER INFORMATION: Synthetic

<400> SEQUENCE: 12

Gly Val Gly Val Pro Gly Val Gly Val Pro Gly Lys Gly Val Pro Gly
1               5                   10                  15

Val Gly Val Pro Gly Val Gly Val Pro Gly Val Gly Val Pro
            20                  25                  30

<210> SEQ ID NO 13
<211> LENGTH: 111
<212> TYPE: PRT
<213> ORGANISM: Artificial Sequence
<220> FEATURE:
<221> NAME/KEY: PEPTIDE
<222> LOCATION: (1)..(111)
<223> OTHER INFORMATION: Synthetic

<400> SEQUENCE: 13

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
            35                  40                  45

Val Pro Gly Val Gly Val Pro Gly Arg Gly Asp Ser Pro Gly Val Gly
        50                  55                  60

Val Pro Gly Val Gly Val Pro Gly Val Gly Val Pro Gly Val Gly Val
    65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro
                100                 105                 110

<210> SEQ ID NO 14
<211> LENGTH: 148
<212> TYPE: PRT
<213> ORGANISM: Artificial Sequence
<220> FEATURE:
<221> NAME/KEY: PEPTIDE
<222> LOCATION: (1)..(148)
<223> OTHER INFORMATION: Synthetic

<400> SEQUENCE: 14

Gly Val Gly Val Pro Gly Val Gly Val Pro Gly Val Gly Val Pro Gly
```

```
                1               5                    10                   15
Val Gly Val Pro Gly Val Gly Val Pro Gly Val Gly Val Pro Gly Val
                        20                  25                  30
Gly Val Pro Gly Val Gly Val Pro Gly Val Gly Val Pro Gly Val Gly
                35                  40                  45
Val Pro Gly Val Gly Val Ala Pro Gly Val Gly Val Ala Pro Gly Val
        50                  55                  60
Gly Val Ala Pro Gly Val Gly Val Ala Pro Gly Val Gly Val Ala Pro
65                  70                  75                  80
Gly Val Gly Val Ala Pro Gly Val Gly Val Ala Pro Gly Val Gly Val
                    85                  90                  95
Ala Pro Gly Val Gly Val Pro Gly Val Gly Val Pro Gly Val Gly Val
                100                 105                 110
Pro Gly Val Gly Val Pro Gly Val Gly Val Pro Gly Val Gly Val Pro
            115                 120                 125
Gly Val Gly Val Pro Gly Val Gly Val Pro Gly Val Gly Val Pro Gly
    130                 135                 140
Val Gly Val Pro
145
```

<210> SEQ ID NO 15
<211> LENGTH: 30
<212> TYPE: PRT
<213> ORGANISM: Artificial Sequence
<220> FEATURE:
<221> NAME/KEY: PEPTIDE
<222> LOCATION: (1)..(30)
<223> OTHER INFORMATION: Synthetic

<400> SEQUENCE: 15

```
Gly Val Gly Val Pro Gly Val Gly Val Pro Gly Glu Gly Val Pro Gly
1               5                   10                  15
Val Gly Val Pro Gly Val Gly Val Pro Gly Val Gly Val Pro
            20                  25                  30
```

<210> SEQ ID NO 16
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Synthetic

<400> SEQUENCE: 16

```
Val Pro Gly Gly
1
```

<210> SEQ ID NO 17
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 17

```
Val Pro Gly Val Gly
1               5
```

<210> SEQ ID NO 18

-continued

```
<211> LENGTH: 1255
<212> TYPE: PRT
<213> ORGANISM: Artificial Sequence
<220> FEATURE:
<221> NAME/KEY: PEPTIDE
<222> LOCATION: (1)..(1255)
<223> OTHER INFORMATION: Synthetic

<400> SEQUENCE: 18
```

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285

Val Pro Gly Val Gly Val Pro Gly Val Gly Val Pro Gly Val Gly Val
    290                 295                 300

Pro Gly Val Gly Val Pro Gly Val Gly Val Pro Gly Val Gly Val Pro
305                 310                 315                 320

Gly Val Gly Val Pro Gly Val Gly Val Pro Gly Val Gly Val Pro Gly
                325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
        355                 360                 365

-continued

Val Pro Gly Val Gly Val Pro Gly Val Gly Val Pro Gly Val Gly Val
        370                 375                 380

Pro Gly Val Gly Val Pro Gly Val Gly Val Pro Gly Val Gly Val Pro
385                 390                 395                 400

Gly Val Gly Val Pro Gly Val Gly Val Pro Gly Val Gly Val Pro Gly
                405                 410                 415

Val Gly Val Pro Gly Val Gly Val Pro Gly Val Gly Val Pro Gly Val
        420                 425                 430

Gly Val Pro Gly Val Gly Val Pro Gly Val Gly Val Pro Gly Val Gly
            435                 440                 445

Val Pro Gly Val Gly Val Pro Gly Val Gly Val Pro Gly Val Gly Val
        450                 455                 460

Pro Gly Val Gly Val Pro Gly Val Gly Val Pro Gly Val Gly Val Pro
465                 470                 475                 480

Gly Val Gly Val Pro Gly Val Gly Val Pro Gly Val Gly Val Pro Gly
                485                 490                 495

Val Gly Val Pro Gly Val Gly Val Pro Gly Val Gly Val Pro Gly Val
        500                 505                 510

Gly Val Pro Gly Val Gly Val Pro Gly Val Gly Val Pro Gly Val Gly
            515                 520                 525

Val Pro Gly Val Gly Val Pro Gly Val Gly Val Pro Gly Val Gly Val
        530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
                565                 570                 575

Val Gly Val Pro Gly Val Gly Val Pro Gly Val Gly Val Pro Gly Val
        580                 585                 590

Gly Val Pro Gly Val Gly Val Pro Gly Val Gly Val Pro Gly Val Gly
            595                 600                 605

Val Pro Gly Val Gly Val Pro Gly Val Gly Val Pro Gly Val Gly Val
        610                 615                 620

Pro Gly Val Gly Val Pro Gly Val Gly Val Pro Gly Val Gly Val Pro
625                 630                 635                 640

Gly Val Gly Val Pro Gly Val Gly Val Pro Gly Val Gly Val Pro Gly
                645                 650                 655

Val Gly Val Pro Gly Val Gly Val Pro Gly Val Gly Val Pro Gly Val
        660                 665                 670

Gly Val Pro Gly Val Gly Val Pro Gly Val Gly Val Pro Gly Val Gly
            675                 680                 685

Val Pro Gly Val Gly Val Pro Gly Val Gly Val Pro Gly Val Gly Val
        690                 695                 700

Pro Gly Val Gly Val Pro Gly Val Gly Val Pro Gly Val Gly Val Pro
705                 710                 715                 720

Gly Val Gly Val Pro Gly Val Gly Val Pro Gly Val Gly Val Pro Gly
                725                 730                 735

Val Gly Val Pro Gly Val Gly Val Pro Gly Val Gly Val Pro Gly Val
        740                 745                 750

Gly Val Pro Gly Val Gly Val Pro Gly Val Gly Val Pro Gly Val Gly
            755                 760                 765

Val Pro Gly Val Gly Val Pro Gly Val Gly Val Pro Gly Val Gly Val
        770                 775                 780

Pro Gly Val Gly Val Pro Gly Val Gly Val Pro Gly Val Gly Val Pro

-continued

```
            785                 790                 795                 800
Gly Val Gly Val Pro Gly Val Gly Val Pro Gly Val Gly Val Pro Gly
                805                 810                 815
Val Gly Val Pro Gly Val Gly Val Pro Gly Val Gly Val Pro Gly Val
                820                 825                 830
Gly Val Pro Gly Val Gly Val Pro Gly Val Gly Val Pro Gly Val Gly
                835                 840                 845
Val Pro Gly Val Gly Val Pro Gly Val Gly Val Pro Gly Val Gly Val
                850                 855                 860
Pro Gly Val Gly Val Pro Gly Val Gly Val Pro Gly Val Gly Val Pro
865                 870                 875                 880
Gly Val Gly Val Pro Gly Val Gly Val Pro Gly Val Gly Val Pro Gly
                885                 890                 895
Val Gly Val Pro Gly Val Gly Val Pro Gly Val Gly Val Pro Gly Val
                900                 905                 910
Gly Val Pro Gly Val Gly Val Pro Gly Val Gly Val Pro Gly Val Gly
                915                 920                 925
Val Pro Gly Val Gly Val Pro Gly Val Gly Val Pro Gly Val Gly Val
                930                 935                 940
Pro Gly Val Gly Val Pro Gly Val Gly Val Pro Gly Val Gly Val Pro
945                 950                 955                 960
Gly Val Gly Val Pro Gly Val Gly Val Pro Gly Val Gly Val Pro Gly
                965                 970                 975
Val Gly Val Pro Gly Val Gly Val Pro Gly Val Gly Val Pro Gly Val
                980                 985                 990
Gly Val Pro Gly Val Gly Val Pro  Gly Val Gly Val Pro  Gly Val Gly
                995                 1000                1005
Val Pro  Gly Val Gly Val Pro  Gly Val Gly Val Pro  Gly Val Gly
    1010                1015                1020
Val Pro  Gly Val Gly Val Pro  Gly Val Gly Val Pro  Gly Val Gly
    1025                1030                1035
Val Pro  Gly Val Gly Val Pro  Gly Val Gly Val Pro  Gly Val Gly
    1040                1045                1050
Val Pro  Gly Val Gly Val Pro  Gly Val Gly Val Pro  Gly Val Gly
    1055                1060                1065
Val Pro  Gly Val Gly Val Pro  Gly Val Gly Val Pro  Gly Val Gly
    1070                1075                1080
Val Pro  Gly Val Gly Val Pro  Gly Val Gly Val Pro  Gly Val Gly
    1085                1090                1095
Val Pro  Gly Val Gly Val Pro  Gly Val Gly Val Pro  Gly Val Gly
    1100                1105                1110
Val Pro  Gly Val Gly Val Pro  Gly Val Gly Val Pro  Gly Val Gly
    1115                1120                1125
Val Pro  Gly Val Gly Val Pro  Gly Val Gly Val Pro  Gly Val Gly
    1130                1135                1140
Val Pro  Gly Val Gly Val Pro  Gly Val Gly Val Pro  Gly Val Gly
    1145                1150                1155
Val Pro  Gly Val Gly Val Pro  Gly Val Gly Val Pro  Gly Val Gly
    1160                1165                1170
Val Pro  Gly Val Gly Val Pro  Gly Val Gly Val Pro  Gly Val Gly
    1175                1180                1185
Val Pro  Gly Val Gly Val Pro  Gly Val Gly Val Pro  Gly Val Gly
    1190                1195                1200
```

```
Val Pro  Gly Val Gly Val Pro  Gly Val Gly Val Pro  Gly Val Gly
    1205                1210                1215

Val Pro  Gly Val Gly Val Pro  Gly Val Gly Val Pro  Gly Val Gly
    1220                1225                1230

Val Pro  Gly Val Gly Val Pro  Gly Val Gly Val Pro  Gly Val Gly
    1235                1240                1245

Val Pro  Gly Val Gly Val Pro
    1250                1255

<210> SEQ ID NO 19
<211> LENGTH: 5
<212> TYPE: PRT
<213> ORGANISM: Artificial Sequence
<220> FEATURE:
<221> NAME/KEY: VARIANT
<222> LOCATION: (4)..(4)
<223> OTHER INFORMATION: the amino acid residue at position 4 is any
      amino acid that is modified to have an
      electroresponsive side chain
<221> NAME/KEY: PEPTIDE
<222> LOCATION: (1)..(5)
<223> OTHER INFORMATION: Synthetic

<400> SEQUENCE: 19

Val Pro Gly Xaa Gly
1               5

<210> SEQ ID NO 20
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 20

Gly Val Gly Val Pro
1               5

<210> SEQ ID NO 21
<211> LENGTH: 166
<212> TYPE: PRT
<213> ORGANISM: Artificial Sequence
<220> FEATURE:
<221> NAME/KEY: PEPTIDE
<222> LOCATION: (1)..(166)
<223> OTHER INFORMATION: Synthetic

<400> SEQUENCE: 21

Gly Gly Ala Pro Gly Gly Ala Pro Gly Gly Ala Pro Gly Gly Ala Pro
1               5                   10                  15

Gly Gly Ala Pro Gly Gly Ala Pro Gly Gly Ala Pro Gly Gly Ala Pro
            20                  25                  30

Gly Gly Ala Pro Gly Gly Ala Pro Gly Gly Ala Pro Gly Gly Ala Pro
        35                  40                  45

Gly Gly Ala Pro Gly Gly Ala Pro Gly Gly Ala Pro Gly Gly Ala Pro
    50                  55                  60

Gly Gly Ala Pro Gly Gly Ala Pro Gly Gly Ala Pro Gly Gly Ala Pro
65                  70                  75                  80

Gly Gly Ala Pro Gly Gly Ala Pro Gly Gly Ala Pro Gly Gly Ala Pro
                85                  90                  95

Gly Gly Ala Pro Gly Gly Ala Pro Gly Gly Ala Pro Gly Gly Ala Pro
```

```
                100             105             110
Gly Gly Ala Pro Gly Gly Ala Pro Gly Gly Ala Pro
        115             120             125

Gly Gly Ala Pro Gly Gly Ala Pro Gly Gly Ala Pro
    130             135             140

Gly Gly Ala Pro Gly Gly Ala Pro Gly Gly Ala Pro
145             150             155             160

Gly Arg Gly Asp Ser Pro
                165

<210> SEQ ID NO 22
<211> LENGTH: 25
<212> TYPE: PRT
<213> ORGANISM: Artificial Sequence
<220> FEATURE:
<221> NAME/KEY: PEPTIDE
<222> LOCATION: (1)..(25)
<223> OTHER INFORMATION: Synthetic

<400> SEQUENCE: 22

Gly Val Gly Val Pro Gly Val Gly Val Pro Gly Val Gly Val Pro Gly
1               5                   10                  15

Val Gly Val Pro Gly Glu Gly Val Pro
            20                  25

<210> SEQ ID NO 23
<211> LENGTH: 100
<212> TYPE: PRT
<213> ORGANISM: Artificial Sequence
<220> FEATURE:
<221> NAME/KEY: PEPTIDE
<222> LOCATION: (1)..(100)
<223> OTHER INFORMATION: Synthetic

<400> SEQUENCE: 23

Gly Ala Gly Gly Ala Thr Cys Cys Gly Ala Ala Gly Ala Cys Ala Ala
1               5                   10                  15

Cys Ala Gly Gly Thr Gly Gly Thr Thr Thr Cys Cys Gly Gly Gly Gly
            20                  25                  30

Cys Gly Gly Cys Gly Thr Ala Cys Cys Gly Gly Thr Gly Gly Cys
        35                  40                  45

Gly Thr Ala Cys Cys Gly Gly Cys Gly Thr Thr Thr Cys Cys
    50                  55                  60

Cys Gly Gly Gly Ala Gly Gly Thr Gly Thr Cys Cys Gly Gly Gly
65                  70                  75                  80

Thr Gly Gly Gly Thr Thr Cys Cys Ala Gly Gly Cys Gly Gly Thr
            85                  90                  95

Gly Thr Ala Cys
        100

<210> SEQ ID NO 24
<211> LENGTH: 100
<212> TYPE: DNA
<213> ORGANISM: Artificial Sequence
<220> FEATURE:
<221> NAME/KEY: misc_feature
<222> LOCATION: (1)..(100)
<223> OTHER INFORMATION: Synthetic

<400> SEQUENCE: 24
ctggatccga agacttcctg gaaaaccgcc cggcacgcca cccggaactc cacccggaac        60
```

-continued accgcccgga aacccacccg gtacaccgcc tggaacccca          100

<210> SEQ ID NO 25
<211> LENGTH: 635
<212> TYPE: PRT
<213> ORGANISM: Artificial Sequence
<220> FEATURE:
<221> NAME/KEY: PEPTIDE
<222> LOCATION: (1)..(635)
<223> OTHER INFORMATION: Synthetic

<400> SEQUENCE: 25

Gly Val Gly Val Pro Gly Val Gly Val Pro Gly Lys Gly Val Pro Gly
1               5                   10                  15

Val Gly Val Pro Gly Val Gly Phe Pro Gly Phe Gly Phe Pro Gly Val
            20                  25                  30

Gly Val Pro Gly Val Gly Val Pro Gly Lys Gly Val Pro Gly Val Gly
        35                  40                  45

Val Pro Gly Val Gly Phe Pro Gly Phe Gly Phe Pro Gly Val Gly Val
    50                  55                  60

Pro Gly Val Gly Val Pro Gly Lys Gly Val Pro Gly Val Gly Val Pro
65                  70                  75                  80

Gly Val Gly Phe Pro Gly Phe Gly Phe Pro Gly Val Gly Val Pro Gly
                85                  90                  95

Val Gly Val Pro Gly Lys Gly Val Pro Gly Val Gly Val Pro Gly Val
            100                 105                 110

Gly Phe Pro Gly Phe Gly Phe Pro Gly Val Gly Val Pro Gly Val Gly
        115                 120                 125

Val Pro Gly Lys Gly Val Pro Gly Val Gly Val Pro Gly Val Gly Phe
    130                 135                 140

Pro Gly Phe Gly Phe Pro Gly Val Gly Val Pro Gly Val Gly Val Pro
145                 150                 155                 160

Gly Lys Gly Val Pro Gly Val Gly Val Pro Gly Val Gly Phe Pro Gly
                165                 170                 175

Phe Gly Phe Pro Gly Val Gly Val Pro Gly Val Gly Val Pro Gly Lys
            180                 185                 190

Gly Val Pro Gly Val Gly Val Pro Gly Val Gly Phe Pro Gly Phe Gly
        195                 200                 205

Phe Pro Gly Val Gly Val Pro Gly Val Gly Val Pro Gly Lys Gly Val
    210                 215                 220

Pro Gly Val Gly Val Pro Gly Val Gly Phe Pro Gly Phe Gly Phe Pro
225                 230                 235                 240

Gly Val Gly Val Pro Gly Val Gly Val Pro Gly Lys Gly Val Pro Gly
                245                 250                 255

Val Gly Val Pro Gly Val Gly Phe Pro Gly Phe Gly Phe Pro Gly Val
            260                 265                 270

Gly Val Pro Gly Val Gly Val Pro Gly Lys Gly Val Pro Gly Val Gly
        275                 280                 285

Val Pro Gly Val Gly Phe Pro Gly Phe Gly Phe Pro Gly Val Gly Val
    290                 295                 300

Pro Gly Val Gly Val Pro Gly Lys Gly Val Pro Gly Val Gly Val Pro
305                 310                 315                 320

Gly Val Gly Phe Pro Gly Phe Gly Phe Pro Gly Val Gly Val Pro Gly
                325                 330                 335

Val Gly Val Pro Gly Lys Gly Val Pro Gly Val Gly Val Pro Gly Val
            340                 345                 350

```
Gly Phe Pro Gly Phe Phe Pro Gly Val Gly Val Pro Gly Val Gly
            355                 360                 365

Val Pro Gly Lys Gly Val Pro Gly Val Gly Val Pro Gly Val Gly Phe
    370                 375                 380

Pro Gly Phe Gly Phe Pro Gly Val Gly Val Pro Gly Val Gly Val Pro
385                 390                 395                 400

Gly Lys Gly Val Pro Gly Val Gly Val Pro Gly Val Gly Phe Pro Gly
                405                 410                 415

Phe Gly Phe Pro Gly Val Gly Val Pro Gly Val Gly Val Pro Gly Lys
            420                 425                 430

Gly Val Pro Gly Val Gly Val Pro Gly Val Gly Phe Pro Gly Phe Gly
        435                 440                 445

Phe Pro Gly Val Gly Val Pro Gly Val Gly Val Pro Gly Lys Gly Val
    450                 455                 460

Pro Gly Val Gly Val Pro Gly Val Gly Phe Pro Gly Phe Gly Phe Pro
465                 470                 475                 480

Gly Val Gly Val Pro Gly Val Gly Val Pro Gly Lys Gly Val Pro Gly
                485                 490                 495

Val Gly Val Pro Gly Val Gly Phe Pro Gly Phe Gly Phe Pro Gly Val
            500                 505                 510

Gly Val Pro Gly Val Gly Val Pro Gly Lys Gly Val Pro Gly Val Gly
        515                 520                 525

Val Pro Gly Val Gly Phe Pro Gly Phe Gly Phe Pro Gly Val Gly Val
    530                 535                 540

Pro Gly Val Gly Val Pro Gly Lys Gly Val Pro Gly Val Gly Val Pro
545                 550                 555                 560

Gly Val Gly Phe Pro Gly Phe Gly Phe Pro Gly Val Gly Val Pro Gly
                565                 570                 575

Val Gly Val Pro Gly Lys Gly Val Pro Gly Val Gly Val Pro Gly Val
            580                 585                 590

Gly Phe Pro Gly Phe Gly Phe Pro Gly Val Gly Val Pro Gly Val Gly
        595                 600                 605

Val Pro Gly Lys Gly Val Pro Gly Val Gly Val Pro Gly Val Gly Phe
    610                 615                 620

Pro Gly Phe Gly Phe Pro Gly Val Gly Val Pro
625                 630                 635

<210> SEQ ID NO 26
<211> LENGTH: 66
<212> TYPE: DNA
<213> ORGANISM: Artificial Sequence
<220> FEATURE:
<221> NAME/KEY: misc_feature
<222> LOCATION: (1)..(66)
<223> OTHER INFORMATION: Synthetic

<400> SEQUENCE: 26
gaggatccag gcgttggggt accgggtgtt ggcgatccgg gtaaaggtgt cccggggttg     60
gtgtgc                                                               66

<210> SEQ ID NO 27
<211> LENGTH: 66
<212> TYPE: DNA
<213> ORGANISM: Artificial Sequence
<220> FEATURE:
<221> NAME/KEY: misc_feature
<222> LOCATION: (1)..(66)
```

<223> OTHER INFORMATION: Synthetic

<400> SEQUENCE: 27
ctggatccaa cgcctgggaa tccgaaaccc ggaaagccta cacccggcac accaacgccc    60
gggaca    66

<210> SEQ ID NO 28
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Synthetic

<400> SEQUENCE: 28

Gly Arg Gly Asp Ser Pro
1               5

<210> SEQ ID NO 29
<211> LENGTH: 50
<212> TYPE: PRT
<213> ORGANISM: Artificial Sequence
<220> FEATURE:
<221> NAME/KEY: PEPTIDE
<222> LOCATION: (1)..(50)
<223> OTHER INFORMATION: Synthetic

<400> SEQUENCE: 29

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro
    50

<210> SEQ ID NO 30
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic

<400> SEQUENCE: 30
ctggatccag accatgggcg tt    22

<210> SEQ ID NO 31
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic

<400> SEQUENCE: 31
ggcgttggtg taccgtaagc ttgaattcgg atccag    36

<210> SEQ ID NO 32
<211> LENGTH: 22
<212> TYPE: DNA

```
<213> ORGANISM: Artificial Sequence
<220> FEATURE:
<221> NAME/KEY: misc_feature
<222> LOCATION: (1)..(22)
<223> OTHER INFORMATION: Synthetic

<400> SEQUENCE: 32
gacctaggtc tggtacccgc aa                                              22

<210> SEQ ID NO 33
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic

<400> SEQUENCE: 33
ccgcaaccac atggcattcg aacttaagcc taggtc                                36

<210> SEQ ID NO 34
<211> LENGTH: 2003
<212> TYPE: PRT
<213> ORGANISM: Artificial Sequence
<220> FEATURE:
<221> NAME/KEY: PEPTIDE
<222> LOCATION: (1)..(2003)
<223> OTHER INFORMATION: Synthetic

<400> SEQUENCE: 34
```

Gly Val Gly Val Pro Gly Val Gly Val Pro Gly Val Gly Val Pro Gly
1               5                  10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Arg Gly Asp Ser Pro Gly Val Gly
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro Gly
            100                 105                 110

Val Gly Val Pro Gly Val Gly Val Pro Gly Val Gly Val Pro Gly Val
        115                 120                 125

Gly Val Pro Gly Val Gly Val Pro Gly Val Gly Val Pro Gly Val Gly
    130                 135                 140

Val Pro Gly Val Gly Val Pro Gly Val Gly Val Pro Gly Val Gly Val
145                 150                 155                 160

Pro Gly Val Gly Val Pro Gly Arg Gly Asp Ser Pro Gly Val Gly Val
                165                 170                 175

Pro Gly Val Gly Val Pro Gly Val Gly Val Pro Gly Val Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly

-continued

```
                225                 230                 235                 240
Val Pro Gly Val Gly Val Pro Gly Val Gly Val Pro Gly Val Gly Val
                245                 250                 255
Pro Gly Val Gly Val Pro Gly Val Gly Val Pro Gly Val Gly Val Pro
                260                 265                 270
Gly Val Gly Val Pro Gly Arg Gly Asp Ser Pro Gly Val Gly Val Pro
                275                 280                 285
Gly Val Gly Val Pro Gly Val Gly Val Pro Gly Val Gly Val Pro Gly
                290                 295                 300
Val Gly Val Pro Gly Val Gly Val Pro Gly Val Gly Val Pro Gly Val
305                 310                 315                 320
Gly Val Pro Gly Val Gly Val Pro Gly Val Gly Val Pro Gly Val Gly
                325                 330                 335
Val Pro Gly Val Gly Val Pro Gly Val Gly Val Pro Gly Val Gly Val
                340                 345                 350
Pro Gly Val Gly Val Pro Gly Val Gly Val Pro Gly Val Gly Val Pro
                355                 360                 365
Gly Val Gly Val Pro Gly Val Gly Val Pro Gly Val Gly Val Pro Gly
                370                 375                 380
Val Gly Val Pro Gly Arg Gly Asp Ser Pro Gly Val Gly Val Pro Gly
385                 390                 395                 400
Val Gly Val Pro Gly Val Gly Val Pro Gly Val Gly Val Pro Gly Val
                405                 410                 415
Gly Val Pro Gly Val Gly Val Pro Gly Val Gly Val Pro Gly Val Gly
                420                 425                 430
Val Pro Gly Val Gly Val Pro Gly Val Gly Val Pro Gly Val Gly Val
                435                 440                 445
Pro Gly Val Gly Val Pro Gly Val Gly Val Pro Gly Val Gly Val Pro
                450                 455                 460
Gly Val Gly Val Pro Gly Val Gly Val Pro Gly Val Gly Val Pro Gly
465                 470                 475                 480
Val Gly Val Pro Gly Val Gly Val Pro Gly Val Gly Val Pro Gly Val
                485                 490                 495
Gly Val Pro Gly Arg Gly Asp Ser Pro Gly Val Gly Val Pro Gly Val
                500                 505                 510
Gly Val Pro Gly Val Gly Val Pro Gly Val Gly Val Pro Gly Val Gly
                515                 520                 525
Val Pro Gly Val Gly Val Pro Gly Val Gly Val Pro Gly Val Gly Val
                530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
                580                 585                 590
Gly Val Pro Gly Val Gly Val Pro Gly Val Gly Val Pro Gly Val Gly
                595                 600                 605
Val Pro Gly Arg Gly Asp Ser Pro Gly Val Gly Val Pro Gly Val Gly
                610                 615                 620
Val Pro Gly Val Gly Val Pro Gly Val Gly Val Pro Gly Val Gly Val
625                 630                 635                 640
Pro Gly Val Gly Val Pro Gly Val Gly Val Pro Gly Val Gly Val Pro
                645                 650                 655
```

-continued

Gly Val Gly Val Pro Gly Val Gly Val Pro Gly Val Gly
            660                 665                 670
Val Gly Val Pro Gly Val Gly Val Pro Gly Val Gly Val
            675                 680                 685
Gly Val Pro Gly Val Gly Val Pro Gly Val Gly Val Gly
            690                 695                 700
Val Pro Gly Val Gly Val Pro Gly Val Gly Val Gly Val
705                 710                 715                 720
Pro Gly Arg Gly Asp Ser Pro Gly Val Gly Val Gly Val
            725                 730                 735
Pro Gly Val Gly Val Pro Gly Val Gly Val Pro Gly Val Pro
            740                 745                 750
Gly Val Gly Val Pro Gly Val Gly Val Pro Gly Val Gly
            755                 760                 765
Val Gly Val Pro Gly Val Gly Val Pro Gly Val Gly Val
            770                 775                 780
Gly Val Pro Gly Val Gly Val Pro Gly Val Gly Val Gly
785                 790                 795                 800
Val Pro Gly Val Gly Val Pro Gly Val Gly Val Gly Val
            805                 810                 815
Pro Gly Val Gly Val Pro Gly Val Gly Val Pro Gly Val Pro
            820                 825                 830
Gly Arg Gly Asp Ser Pro Gly Val Gly Val Pro Gly Val Pro
            835                 840                 845
Gly Val Gly Val Pro Gly Val Gly Val Pro Gly Val Gly
            850                 855                 860
Val Gly Val Pro Gly Val Gly Val Pro Gly Val Gly Val
865                 870                 875                 880
Gly Val Pro Gly Val Gly Val Pro Gly Val Gly Val Gly
            885                 890                 895
Val Pro Gly Val Gly Val Pro Gly Val Gly Val Gly Val
            900                 905                 910
Pro Gly Val Gly Val Pro Gly Val Gly Val Pro Gly Val Pro
            915                 920                 925
Gly Val Gly Val Pro Gly Val Gly Val Pro Gly Val Gly
            930                 935                 940
Arg Gly Asp Ser Pro Gly Val Gly Val Pro Gly Val Gly
945                 950                 955                 960
Val Gly Val Pro Gly Val Gly Val Pro Gly Val Gly Val
            965                 970                 975
Gly Val Pro Gly Val Gly Val Pro Gly Val Gly Val Gly
            980                 985                 990
Val Pro Gly Val Gly Val Pro Gly Val Gly Val Pro Gly Val Gly Val
            995                 1000                1005
Pro Gly Val Gly Val Pro Gly Val Gly Val Pro Gly Val Gly Val
            1010                1015                1020
Pro Gly Val Gly Val Pro Gly Val Gly Val Pro Gly Val Gly Val
            1025                1030                1035
Pro Gly Val Gly Val Pro Gly Val Gly Val Pro Gly Val Gly Val
            1040                1045                1050
Pro Gly Arg Gly Asp Ser Pro Gly Val Gly Val Pro Gly Val Gly
            1055                1060                1065

-continued

Val Pro Gly Val Gly Val Pro Gly Val Gly Val Pro Gly Val Gly
    1070                1075                1080
Val Pro Gly Val Gly Val Pro Gly Val Gly Val Pro Gly Val Gly
    1085                1090                1095
Val Pro Gly Val Gly Val Pro Gly Val Gly Val Pro Gly Val Gly
    1100                1105                1110
Val Pro Gly Val Gly Val Pro Gly Val Gly Val Pro Gly Val Gly
    1115                1120                1125
Val Pro Gly Val Gly Val Pro Gly Val Gly Val Pro Gly Val Gly
    1130                1135                1140
Val Pro Gly Val Gly Val Pro Gly Val Gly Val Pro Gly Val Gly
    1145                1150                1155
Val Pro Gly Val Gly Val Pro Gly Arg Gly Asp Ser Pro Gly Val
    1160                1165                1170
Gly Val Pro Gly Val Gly Val Pro Gly Val Gly Val Pro Gly Val
    1175                1180                1185
Gly Val Pro Gly Val Gly Val Pro Gly Val Gly Val Pro Gly Val
    1190                1195                1200
Gly Val Pro Gly Val Gly Val Pro Gly Val Gly Val Pro Gly Val
    1205                1210                1215
Gly Val Pro Gly Val Gly Val Pro Gly Val Gly Val Pro Gly Val
    1220                1225                1230
Gly Val Pro Gly Val Gly Val Pro Gly Val Gly Val Pro Gly Val
    1235                1240                1245
Gly Val Pro Gly Val Gly Val Pro Gly Val Gly Val Pro Gly Val
    1250                1255                1260
Gly Val Pro Gly Val Gly Val Pro Gly Val Gly Val Pro Gly Arg
    1265                1270                1275
Gly Asp Ser Pro Gly Val Gly Val Pro Gly Val Gly Val Pro Gly
    1280                1285                1290
Val Gly Val Pro Gly Val Gly Val Pro Gly Val Gly Val Pro Gly
    1295                1300                1305
Val Gly Val Pro Gly Val Gly Val Pro Gly Val Gly Val Pro Gly
    1310                1315                1320
Val Gly Val Pro Gly Val Gly Val Pro Gly Val Gly Val Pro Gly
    1325                1330                1335
Val Gly Val Pro Gly Val Gly Val Pro Gly Val Gly Val Pro Gly
    1340                1345                1350
Val Gly Val Pro Gly Val Gly Val Pro Gly Val Gly Val Pro Gly
    1355                1360                1365
Val Gly Val Pro Gly Val Gly Val Pro Gly Val Gly Val Pro Gly
    1370                1375                1380
Val Gly Val Pro Gly Arg Gly Asp Ser Pro Gly Val Gly Val Pro
    1385                1390                1395
Gly Val Gly Val Pro Gly Val Gly Val Pro Gly Val Gly Val Pro
    1400                1405                1410
Gly Val Gly Val Pro Gly Val Gly Val Pro Gly Val Gly Val Pro
    1415                1420                1425
Gly Val Gly Val Pro Gly Val Gly Val Pro Gly Val Gly Val Pro
    1430                1435                1440
Gly Val Gly Val Pro Gly Val Gly Val Pro Gly Val Gly Val Pro
    1445                1450                1455
Gly Val Gly Val Pro Gly Val Gly Val Pro Gly Val Gly Val Pro

-continued

```
                    1460                 1465                 1470
Gly Val  Gly Val Pro Gly Val  Gly Val Pro Gly Val Pro
    1475                 1480                 1485
Gly Val  Gly Val Pro Gly Val  Gly Val Pro Gly Arg  Gly Asp Ser
    1490                 1495                 1500
Pro Gly  Val Gly Val Pro Gly  Val Gly Val Pro Gly  Val Gly Val
    1505                 1510                 1515
Pro Gly  Val Gly Val Pro Gly  Val Gly Val Pro Gly  Val Gly Val
    1520                 1525                 1530
Pro Gly  Val Gly Val Pro Gly  Val Gly Val Pro Gly  Val Gly Val
    1535                 1540                 1545
Pro Gly  Val Gly Val Pro Gly  Val Gly Val Pro Gly  Val Gly Val
    1550                 1555                 1560
Pro Gly  Val Gly Val Pro Gly  Val Gly Val Pro Gly  Val Gly Val
    1565                 1570                 1575
Pro Gly  Val Gly Val Pro Gly  Val Gly Val Pro Gly  Val Gly Val
    1580                 1585                 1590
Pro Gly  Val Gly Val Pro Gly  Val Gly Val Pro Gly  Val Gly Val
    1595                 1600                 1605
Pro Gly  Arg Gly Asp Ser Pro  Gly Val Gly Val Pro  Gly Val Gly
    1610                 1615                 1620
Val Pro  Gly Val Gly Val Pro  Gly Val Gly Val Pro  Gly Val Gly
    1625                 1630                 1635
Val Pro  Gly Val Gly Val Pro  Gly Val Gly Val Pro  Gly Val Gly
    1640                 1645                 1650
Val Pro  Gly Val Gly Val Pro  Gly Val Gly Val Pro  Gly Val Gly
    1655                 1660                 1665
Val Pro  Gly Val Gly Val Pro  Gly Val Gly Val Pro  Gly Val Gly
    1670                 1675                 1680
Val Pro  Gly Val Gly Val Pro  Gly Val Gly Val Pro  Gly Val Gly
    1685                 1690                 1695
Val Pro  Gly Val Gly Val Pro  Gly Val Gly Val Pro  Gly Val Gly
    1700                 1705                 1710
Val Pro  Gly Val Gly Val Pro  Gly Arg Gly Asp Ser  Pro Gly Val
    1715                 1720                 1725
Gly Val  Pro Gly Val Gly Val  Pro Gly Val Gly Val  Pro Gly Val
    1730                 1735                 1740
Gly Val  Pro Gly Val Gly Val  Pro Gly Val Gly Val  Pro Gly Val
    1745                 1750                 1755
Gly Val  Pro Gly Val Gly Val  Pro Gly Val Gly Val  Pro Gly Val
    1760                 1765                 1770
Gly Val  Pro Gly Val Gly Val  Pro Gly Val Gly Val  Pro Gly Val
    1775                 1780                 1785
Gly Val  Pro Gly Val Gly Val  Pro Gly Val Gly Val  Pro Gly Val
    1790                 1795                 1800
Gly Val  Pro Gly Val Gly Val  Pro Gly Val Gly Val  Pro Gly Val
    1805                 1810                 1815
Gly Val  Pro Gly Val Gly Val  Pro Gly Val Gly Val  Pro Gly Arg
    1820                 1825                 1830
Gly Asp  Ser Pro Gly Val Gly  Val Pro Gly Val Gly  Val Pro Gly
    1835                 1840                 1845
Val Gly  Val Pro Gly Val Gly  Val Pro Gly Val Gly  Val Pro Gly
    1850                 1855                 1860
```

```
Val Gly Val Pro Gly Val Gly Val Pro Gly Val Gly Val Pro Gly
    1865                1870                1875

Val Gly Val Pro Gly Val Gly Val Pro Gly Val Gly Val Pro Gly
    1880                1885                1890

Val Gly Val Pro Gly Val Gly Val Pro Gly Val Gly Val Pro Gly
    1895                1900                1905

Val Gly Val Pro Gly Val Gly Val Pro Gly Val Gly Val Pro Gly
    1910                1915                1920

Val Gly Val Pro Gly Val Gly Val Pro Gly Val Gly Val Pro Gly
    1925                1930                1935

Val Gly Val Pro Gly Arg Gly Asp Ser Pro Gly Val Gly Val Pro
    1940                1945                1950

Gly Val Gly Val Pro Gly Val Gly Val Pro Gly Val Gly Val Pro
    1955                1960                1965

Gly Val Gly Val Pro Gly Val Gly Val Pro Gly Val Gly Val Pro
    1970                1975                1980

Gly Val Gly Val Pro Gly Val Gly Val Pro Gly Val Gly Val Pro
    1985                1990                1995

Gly Val Gly Val Pro
    2000

<210> SEQ ID NO 35
<211> LENGTH: 1085
<212> TYPE: PRT
<213> ORGANISM: Artificial Sequence
<220> FEATURE:
<221> NAME/KEY: PEPTIDE
<222> LOCATION: (1)..(1085)
<223> OTHER INFORMATION: Synthetic

<400> SEQUENCE: 35

Gly Val Gly Val Pro Gly Val Gly Val Pro Gly Val Gly Val Pro Gly
1               5                   10                  15

Lys Gly Val Pro Gly Val Gly Val Pro Gly Val Gly Val Pro Gly Val
                20                  25                  30

Gly Val Pro Gly Val Gly Val Pro Gly Val Gly Val Pro Gly Lys Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Lys Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Lys Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Lys Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Lys Gly Val Pro Gly Val Gly Val Pro Gly
                165                 170                 175

Val Gly Val Pro Gly Val Gly Val Pro Gly Val Gly Val Pro Gly Val
            180                 185                 190
```

-continued

Gly Val Pro Gly Lys Gly Val Pro Gly Val Pro Gly Val Gly
        195                 200                 205

Val Pro Gly Val Gly Val Pro Gly Val Gly Val Pro Gly Val Gly Val
        210                 215                 220

Pro Gly Lys Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Lys Gly Val Pro Gly Val Gly Val Pro Gly Val Gly Val Pro Gly Val
                260                 265                 270

Gly Val Pro Gly Val Gly Val Pro Gly Val Gly Val Pro Gly Lys Gly
            275                 280                 285

Val Pro Gly Val Gly Val Pro Gly Val Gly Val Pro Gly Val Gly Val
        290                 295                 300

Pro Gly Val Gly Val Pro Gly Val Gly Val Pro Gly Lys Gly Val Pro
305                 310                 315                 320

Gly Val Gly Val Pro Gly Val Gly Val Pro Gly Val Gly Val Pro Gly
                325                 330                 335

Val Gly Val Pro Gly Val Gly Val Pro Gly Lys Gly Val Pro Gly Val
            340                 345                 350

Gly Val Pro Gly Val Gly Val Pro Gly Val Gly Val Pro Gly Val Gly
            355                 360                 365

Val Pro Gly Val Gly Val Pro Gly Lys Gly Val Pro Gly Val Gly Val
        370                 375                 380

Pro Gly Val Gly Val Pro Gly Val Gly Val Pro Gly Val Gly Val Pro
385                 390                 395                 400

Gly Val Gly Val Pro Gly Lys Gly Val Pro Gly Val Gly Val Pro Gly
                405                 410                 415

Val Gly Val Pro Gly Val Gly Val Pro Gly Val Gly Val Pro Gly Val
            420                 425                 430

Gly Val Pro Gly Lys Gly Val Pro Gly Val Gly Val Pro Gly Val Gly
            435                 440                 445

Val Pro Gly Val Gly Val Pro Gly Val Gly Val Pro Gly Val Gly Val
        450                 455                 460

Pro Gly Lys Gly Val Pro Gly Val Gly Val Pro Gly Val Gly Val Pro
465                 470                 475                 480

Gly Val Gly Val Pro Gly Val Gly Val Pro Gly Val Gly Val Pro Gly
                485                 490                 495

Lys Gly Val Pro Gly Val Gly Val Pro Gly Val Gly Val Pro Gly Val
                500                 505                 510

Gly Val Pro Gly Val Gly Val Pro Gly Val Gly Val Pro Gly Lys Gly
            515                 520                 525

Val Pro Gly Val Gly Val Pro Gly Val Gly Val Pro Gly Val Gly Val
        530                 535                 540

Pro Gly Val Gly Val Pro Gly Val Gly Val Pro Gly Lys Gly Val Pro
545                 550                 555                 560

Gly Val Gly Val Pro Gly Val Gly Val Pro Gly Val Gly Val Pro Gly
                565                 570                 575

Val Gly Val Pro Gly Val Gly Val Pro Gly Lys Gly Val Pro Gly Val
            580                 585                 590

Gly Val Pro Gly Val Gly Val Pro Gly Val Gly Val Pro Gly Val Gly
            595                 600                 605

Val Pro Gly Val Gly Val Pro Gly Lys Gly Val Pro Gly Val Gly Val

-continued

```
            610             615             620
Pro Gly Val Gly Val Pro Gly Val Gly Val Pro Gly Val Pro
625             630             635             640
Gly Val Gly Val Pro Gly Lys Gly Val Pro Gly Val Gly Val Pro Gly
            645             650             655
Val Gly Val Pro Gly Val Gly Val Pro Gly Val Gly Val Pro Gly Val
            660             665             670
Gly Val Pro Gly Lys Gly Val Pro Gly Val Gly Val Pro Gly Val Gly
            675             680             685
Val Pro Gly Val Gly Val Pro Gly Val Gly Val Pro Gly Val Gly Val
            690             695             700
Pro Gly Lys Gly Val Pro Gly Val Gly Val Pro Gly Val Gly Val Pro
705             710             715             720
Gly Val Gly Val Pro Gly Val Gly Val Pro Gly Val Gly Val Pro Gly
            725             730             735
Lys Gly Val Pro Gly Val Gly Val Pro Gly Val Gly Val Pro Gly Val
            740             745             750
Gly Val Pro Gly Val Gly Val Pro Gly Val Gly Val Pro Gly Lys Gly
            755             760             765
Val Pro Gly Val Gly Val Pro Gly Val Gly Val Pro Gly Val Gly Val
            770             775             780
Pro Gly Val Gly Val Pro Gly Val Gly Val Pro Gly Lys Gly Val Pro
785             790             795             800
Gly Val Gly Val Pro Gly Val Gly Val Pro Gly Val Gly Val Pro Gly
            805             810             815
Val Gly Val Pro Gly Val Gly Val Pro Gly Lys Gly Val Pro Gly Val
            820             825             830
Gly Val Pro Gly Val Gly Val Pro Gly Val Gly Val Pro Gly Val Gly
            835             840             845
Val Pro Gly Val Gly Val Pro Gly Lys Gly Val Pro Gly Val Gly Val
            850             855             860
Pro Gly Val Gly Val Pro Gly Val Gly Val Pro Gly Val Gly Val Pro
865             870             875             880
Gly Val Gly Val Pro Gly Lys Gly Val Pro Gly Val Gly Val Pro Gly
            885             890             895
Val Gly Val Pro Gly Val Gly Val Pro Gly Val Gly Val Pro Gly Val
            900             905             910
Gly Val Pro Gly Lys Gly Val Pro Gly Val Gly Val Pro Gly Val Gly
            915             920             925
Val Pro Gly Val Gly Val Pro Gly Val Gly Val Pro Gly Val Gly Val
            930             935             940
Pro Gly Lys Gly Val Pro Gly Val Gly Val Pro Gly Val Gly Val Pro
945             950             955             960
Gly Val Gly Val Pro Gly Val Gly Val Pro Gly Val Gly Val Pro Gly
            965             970             975
Lys Gly Val Pro Gly Val Gly Val Pro Gly Val Gly Val Pro Gly Val
            980             985             990
Gly Val Pro Gly Val Gly Val Pro  Gly Val Gly Val Pro  Gly Lys Gly
            995             1000            1005
Val Pro  Gly Val Gly Val Pro  Gly Val Gly Val Pro  Gly Val Gly
            1010            1015            1020
Val Pro  Gly Val Gly Val Pro  Gly Val Gly Val Pro  Gly Lys Gly
            1025            1030            1035
```

```
Val Pro Gly Val Gly Val Pro Gly Val Gly Val Pro Gly Val Gly
    1040                1045                1050

Val Pro Gly Val Gly Val Pro Gly Val Gly Val Pro Gly Lys Gly
    1055                1060                1065

Val Pro Gly Val Gly Val Pro Gly Val Gly Val Pro Gly Val Gly
    1070                1075                1080

Val Pro
    1085

<210> SEQ ID NO 36
<211> LENGTH: 635
<212> TYPE: PRT
<213> ORGANISM: Artificial Sequence
<220> FEATURE:
<221> NAME/KEY: PEPTIDE
<222> LOCATION: (1)..(635)
<223> OTHER INFORMATION: Synthetic

<400> SEQUENCE: 36

Gly Val Gly Val Pro Gly Val Gly Val Pro Gly Lys Gly Val Pro Gly
1               5                   10                  15

Val Gly Val Pro Gly Val Gly Phe Pro Gly Phe Gly Phe Pro Gly Val
            20                  25                  30

Gly Val Pro Gly Val Gly Val Pro Gly Lys Gly Val Pro Gly Val Gly
        35                  40                  45

Val Pro Gly Val Gly Phe Pro Gly Phe Gly Phe Pro Gly Val Gly Val
    50                  55                  60

Pro Gly Val Gly Val Pro Gly Lys Gly Val Pro Gly Val Gly Val Pro
65                  70                  75                  80

Gly Val Gly Phe Pro Gly Phe Gly Phe Pro Gly Val Gly Val Pro Gly
                85                  90                  95

Val Gly Val Pro Gly Lys Gly Val Pro Gly Val Gly Val Pro Gly Val
            100                 105                 110

Gly Phe Pro Gly Phe Gly Phe Pro Gly Val Gly Val Pro Gly Val Gly
        115                 120                 125

Val Pro Gly Lys Gly Val Pro Gly Val Gly Val Pro Gly Val Gly Phe
    130                 135                 140

Pro Gly Phe Gly Phe Pro Gly Val Gly Val Pro Gly Val Gly Val Pro
145                 150                 155                 160

Gly Lys Gly Val Pro Gly Val Gly Val Pro Gly Val Gly Phe Pro Gly
                165                 170                 175

Phe Gly Phe Pro Gly Val Gly Val Pro Gly Val Gly Val Pro Gly Lys
            180                 185                 190

Gly Val Pro Gly Val Gly Val Pro Gly Val Gly Phe Pro Gly Phe Gly
        195                 200                 205

Phe Pro Gly Val Gly Val Pro Gly Val Gly Val Pro Gly Lys Gly Val
    210                 215                 220

Pro Gly Val Gly Val Pro Gly Val Gly Phe Pro Gly Phe Gly Phe Pro
225                 230                 235                 240

Gly Val Gly Val Pro Gly Val Gly Val Pro Gly Lys Gly Val Pro Gly
                245                 250                 255

Val Gly Val Pro Gly Val Gly Phe Pro Gly Phe Gly Phe Pro Gly Val
            260                 265                 270

Gly Val Pro Gly Val Gly Val Pro Gly Lys Gly Val Pro Gly Val Gly
        275                 280                 285
```

Val Pro Gly Val Gly Phe Pro Gly Phe Gly Phe Pro Gly Val Gly Val
    290                 295                 300

Pro Gly Val Gly Val Pro Gly Lys Gly Val Pro Gly Val Gly Val Pro
305                 310                 315                 320

Gly Val Gly Phe Pro Gly Phe Gly Phe Pro Gly Val Gly Val Pro Gly
                325                 330                 335

Val Gly Val Pro Gly Lys Gly Val Pro Gly Val Gly Val Pro Gly Val
            340                 345                 350

Gly Phe Pro Gly Phe Gly Phe Pro Gly Val Gly Val Pro Gly Val Gly
        355                 360                 365

Val Pro Gly Lys Gly Val Pro Gly Val Gly Val Pro Gly Val Gly Phe
    370                 375                 380

Pro Gly Phe Gly Phe Pro Gly Val Gly Val Pro Gly Val Gly Val Pro
385                 390                 395                 400

Gly Lys Gly Val Pro Gly Val Gly Val Pro Gly Val Gly Phe Pro Gly
                405                 410                 415

Phe Gly Phe Pro Gly Val Gly Val Pro Gly Val Gly Val Pro Gly Lys
            420                 425                 430

Gly Val Pro Gly Val Gly Val Pro Gly Val Gly Phe Pro Gly Phe Gly
        435                 440                 445

Phe Pro Gly Val Gly Val Pro Gly Val Gly Val Pro Gly Lys Gly Val
    450                 455                 460

Pro Gly Val Gly Val Pro Gly Val Gly Phe Pro Gly Phe Gly Phe Pro
465                 470                 475                 480

Gly Val Gly Val Pro Gly Val Gly Val Pro Gly Lys Gly Val Pro Gly
                485                 490                 495

Val Gly Val Pro Gly Val Gly Phe Pro Gly Phe Gly Phe Pro Gly Val
            500                 505                 510

Gly Val Pro Gly Val Gly Val Pro Gly Lys Gly Val Pro Gly Val Gly
        515                 520                 525

Val Pro Gly Val Gly Phe Pro Gly Phe Gly Phe Pro Gly Val Gly Val
    530                 535                 540

Pro Gly Val Gly Val Pro Gly Lys Gly Val Pro Gly Val Gly Val Pro
545                 550                 555                 560

Gly Val Gly Phe Pro Gly Phe Gly Phe Pro Gly Val Gly Val Pro Gly
                565                 570                 575

Val Gly Val Pro Gly Lys Gly Val Pro Gly Val Gly Val Pro Gly Val
            580                 585                 590

Gly Phe Pro Gly Phe Gly Phe Pro Gly Val Gly Val Pro Gly Val Gly
        595                 600                 605

Val Pro Gly Lys Gly Val Pro Gly Val Gly Val Pro Gly Val Gly Phe
    610                 615                 620

Pro Gly Phe Gly Phe Pro Gly Val Gly Val Pro
625                 630                 635

<210> SEQ ID NO 37
<211> LENGTH: 782
<212> TYPE: PRT
<213> ORGANISM: Artificial Sequence
<220> FEATURE:
<221> NAME/KEY: PEPTIDE
<222> LOCATION: (1)..(782)
<223> OTHER INFORMATION: Synthetic

<400> SEQUENCE: 37

Gly Val Gly Val Pro Gly Val Gly Val Pro Gly Val Gly Val Pro Gly

-continued

```
1               5                  10                 15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
                35                  40                  45
Val Pro Gly Val Gly Val Pro Gly Arg Gly Asp Ser Pro Gly Val Gly
        50                  55                  60
Val Pro Gly Val Gly Val Pro Gly Val Gly Val Pro Gly Val Gly Val
65                  70                  75                  80
Pro Gly Val Gly Val Pro Gly Val Gly Val Pro Gly Val Gly Val Pro
                85                  90                  95
Gly Val Gly Val Pro Gly Val Gly Val Pro Gly Val Gly Val Pro Gly
                100                 105                 110
Val Gly Val Pro Gly Val Gly Val Pro Gly Val Gly Val Pro Gly Val
                115                 120                 125
Gly Val Pro Gly Val Gly Val Pro Gly Val Gly Val Pro Gly Val Gly
        130                 135                 140
Val Pro Gly Val Gly Val Pro Gly Val Gly Val Pro Gly Val Gly Val
145                 150                 155                 160
Pro Gly Val Gly Val Pro Gly Arg Gly Asp Ser Pro Gly Val Gly Val
                165                 170                 175
Pro Gly Val Gly Val Pro Gly Val Gly Val Pro Gly Val Gly Val Pro
                180                 185                 190
Gly Val Gly Val Pro Gly Val Gly Val Pro Gly Val Gly Val Pro Gly
            195                 200                 205
Val Gly Val Pro Gly Val Gly Val Pro Gly Val Gly Val Pro Gly Val
        210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Val Gly Val Pro Gly Val Gly Val Pro Gly Val Gly Val Pro
                260                 265                 270
Gly Val Gly Val Pro Gly Arg Gly Asp Ser Pro Gly Val Gly Val Pro
            275                 280                 285
Gly Val Gly Val Pro Gly Val Gly Val Pro Gly Val Gly Val Pro Gly
        290                 295                 300
Val Gly Val Pro Gly Val Gly Val Pro Gly Val Gly Val Pro Gly Val
305                 310                 315                 320
Gly Val Pro Gly Val Gly Val Pro Gly Val Gly Val Pro Gly Val Gly
                325                 330                 335
Val Pro Gly Val Gly Val Pro Gly Val Gly Val Pro Gly Val Gly Val
                340                 345                 350
Pro Gly Val Gly Val Pro Gly Val Gly Val Pro Gly Val Gly Val Pro
            355                 360                 365
Gly Val Gly Val Pro Gly Val Gly Val Pro Gly Val Gly Val Pro Gly
        370                 375                 380
Val Gly Val Pro Gly Arg Gly Asp Ser Pro Gly Val Gly Val Pro Gly
385                 390                 395                 400
Val Gly Val Pro Gly Val Gly Val Pro Gly Val Gly Val Pro Gly Val
                405                 410                 415
Gly Val Pro Gly Val Gly Val Pro Gly Val Gly Val Pro Gly Val Gly
            420                 425                 430
```

Val Pro Gly Val Gly Val Pro Gly Val Gly Val Pro Gly Val Gly Val
            435                 440                 445

Pro Gly Val Gly Val Pro Gly Val Gly Val Pro Gly Val Gly Val Pro
450                 455                 460

Gly Val Gly Val Pro Gly Val Gly Val Pro Gly Val Gly Val Pro Gly
465                 470                 475                 480

Val Gly Val Pro Gly Val Gly Val Pro Gly Val Gly Val Pro Gly Val
                485                 490                 495

Gly Val Pro Gly Arg Gly Asp Ser Pro Gly Val Gly Val Pro Gly Val
            500                 505                 510

Gly Val Pro Gly Val Gly Val Pro Gly Val Gly Val Pro Gly Val Gly
            515                 520                 525

Val Pro Gly Val Gly Val Pro Gly Val Gly Val Pro Gly Val Gly Val
530                 535                 540

Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
                565                 570                 575

Val Gly Val Pro Gly Val Gly Val Pro Gly Val Gly Val Pro Gly Val
            580                 585                 590

Gly Val Pro Gly Val Gly Val Pro Gly Val Gly Val Pro Gly Val Gly
            595                 600                 605

Val Pro Gly Arg Gly Asp Ser Pro Gly Val Gly Val Pro Gly Val Gly
            610                 615                 620

Val Pro Gly Val Gly Val Pro Gly Val Gly Val Pro Gly Val Gly Val
625                 630                 635                 640

Pro Gly Val Gly Val Pro Gly Val Gly Val Pro Gly Val Gly Val Pro
                645                 650                 655

Gly Val Gly Val Pro Gly Val Gly Val Pro Gly Val Gly Val Pro Gly
            660                 665                 670

Val Gly Val Pro Gly Val Gly Val Pro Gly Val Gly Val Pro Gly Val
            675                 680                 685

Gly Val Pro Gly Val Gly Val Pro Gly Val Gly Val Pro Gly Val Gly
            690                 695                 700

Val Pro Gly Val Gly Val Pro Gly Val Gly Val Pro Gly Val Gly Val
705                 710                 715                 720

Pro Gly Arg Gly Asp Ser Pro Gly Val Gly Val Pro Gly Val Gly Val
                725                 730                 735

Pro Gly Val Gly Val Pro Gly Val Gly Val Pro Gly Val Gly Val Pro
            740                 745                 750

Gly Val Gly Val Pro Gly Val Gly Val Pro Gly Val Gly Val Pro Gly
            755                 760                 765

Val Gly Val Pro Gly Val Gly Val Pro Gly Val Gly Val Pro
            770                 775                 780

<210> SEQ ID NO 38
<211> LENGTH: 745
<212> TYPE: PRT
<213> ORGANISM: Artificial Sequence
<220> FEATURE:
<221> NAME/KEY: PEPTIDE
<222> LOCATION: (1)..(745)
<223> OTHER INFORMATION: Synthetic

<400> SEQUENCE: 38

-continued

```
Gly Val Gly Val Pro Gly Val Gly Val Pro Gly Val Gly Val Pro Gly
1               5                  10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Ala Pro Gly Val Gly Val Ala Pro Gly Val
    50                  55                  60

Gly Val Ala Pro Gly Val Gly Val Ala Pro Gly Val Gly Val Ala Pro
65                  70                  75                  80

Gly Val Gly Val Ala Pro Gly Val Gly Val Ala Pro Gly Val Gly Val
            85                  90                  95

Ala Pro Gly Val Gly Val Pro Gly Val Gly Val Pro Gly Val Gly Val
            100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
        165                 170                 175

Val Pro Gly Val Gly Val Pro Gly Val Gly Val Pro Gly Val Gly Val
        180                 185                 190

Pro Gly Val Gly Val Pro Gly Val Gly Val Ala Pro Gly Val Gly Val
    195                 200                 205

Ala Pro Gly Val Gly Val Ala Pro Gly Val Gly Val Ala Pro Gly Val
    210                 215                 220

Gly Val Ala Pro Gly Val Gly Val Ala Pro Gly Val Gly Val Ala Pro
225                 230                 235                 240

Gly Val Gly Val Ala Pro Gly Val Gly Val Pro Gly Val Gly Val Pro
            245                 250                 255

Gly Val Gly Val Pro Gly Val Gly Val Pro Gly Val Gly Val Pro Gly
        260                 265                 270

Val Gly Val Pro Gly Val Gly Val Pro Gly Val Gly Val Pro Gly Val
    275                 280                 285

Gly Val Pro Gly Val Gly Val Pro Gly Val Gly Val Pro Gly Val Gly
290                 295                 300

Val Pro Gly Val Gly Val Pro Gly Val Gly Val Pro Gly Val Gly Val
305                 310                 315                 320

Pro Gly Val Gly Val Pro Gly Val Gly Val Pro Gly Val Gly Val Pro
            325                 330                 335

Gly Val Gly Val Pro Gly Val Gly Val Pro Gly Val Gly Val Ala Pro
        340                 345                 350

Gly Val Gly Val Ala Pro Gly Val Gly Val Ala Pro Gly Val Gly Val
        355                 360                 365

Ala Pro Gly Val Gly Val Ala Pro Gly Val Gly Val Ala Pro Gly Val
    370                 375                 380

Gly Val Ala Pro Gly Val Gly Val Ala Pro Gly Val Gly Val Pro Gly
385                 390                 395                 400

Val Gly Val Pro Gly Val Gly Val Pro Gly Val Gly Val Pro Gly Val
            405                 410                 415

Gly Val Pro Gly Val Gly Val Pro Gly Val Gly Val Pro Gly Val Gly
```

```
                420             425             430
Val Pro Gly Val Gly Val Pro Gly Val Gly Val Pro Gly Val Gly Val
            435             440             445
Pro Gly Val Gly Val Pro Gly Val Gly Val Pro Gly Val Gly Val Pro
        450             455             460
Gly Val Gly Val Pro Gly Val Gly Val Pro Gly Val Gly Val Pro Gly
465             470             475             480
Val Gly Val Pro Gly Val Gly Val Pro Gly Val Gly Val Pro Gly Val
                485             490             495
Gly Val Ala Pro Gly Val Gly Val Ala Pro Gly Val Gly Val Ala Pro
            500             505             510
Gly Val Gly Val Ala Pro Gly Val Gly Val Ala Pro Gly Val Gly Val
        515             520             525
Ala Pro Gly Val Gly Val Ala Pro Gly Val Gly Val Ala Pro Gly Val
    530             535             540
Gly Val Pro Gly Val Gly Val Pro Gly Val Gly Val Pro Gly Val Gly
545             550             555             560
Val Pro Gly Val Gly Val Pro Gly Val Gly Val Pro Gly Val Gly Val
                565             570             575
Pro Gly Val Gly Val Pro Gly Val Gly Val Pro Gly Val Gly Val Pro
            580             585             590
Gly Val Gly Val Pro Gly Val Gly Val Pro Gly Val Gly Val Pro Gly
        595             600             605
Val Gly Val Pro Gly Val Gly Val Pro Gly Val Gly Val Pro Gly Val
    610             615             620
Gly Val Pro Gly Val Gly Val Pro Gly Val Gly Val Pro Gly Val Gly
625             630             635             640
Val Pro Gly Val Gly Val Ala Pro Gly Val Gly Val Ala Pro Gly Val
                645             650             655
Gly Val Ala Pro Gly Val Gly Val Ala Pro Gly Val Gly Val Ala Pro
            660             665             670
Gly Val Gly Val Ala Pro Gly Val Gly Val Ala Pro Gly Val Gly Val
        675             680             685
Ala Pro Gly Val Gly Val Pro Gly Val Gly Val Pro Gly Val Gly Val
    690             695             700
Pro Gly Val Gly Val Pro Gly Val Gly Val Pro Gly Val Gly Val Pro
705             710             715             720
Gly Val Gly Val Pro Gly Val Gly Val Pro Gly Val Gly Val Pro Gly
                725             730             735
Val Gly Val Pro Gly Val Gly Val Pro
            740             745

<210> SEQ ID NO 39
<211> LENGTH: 1085
<212> TYPE: PRT
<213> ORGANISM: Artificial Sequence
<220> FEATURE:
<221> NAME/KEY: PEPTIDE
<222> LOCATION: (1)..(1085)
<223> OTHER INFORMATION: Synthetic

<400> SEQUENCE: 39

Gly Val Gly Val Pro Gly Val Gly Val Pro Gly Val Gly Val Pro Gly
1               5                   10                  15
Glu Gly Val Pro Gly Val Gly Val Pro Gly Val Gly Val Pro Gly Val
                20                  25                  30
```

-continued

```
Gly Val Pro Gly Val Gly Val Pro Gly Val Gly Val Pro Gly Glu Gly
         35                  40                  45
Val Pro Gly Val Gly Val Pro Gly Val Gly Val Pro Gly Val Gly Val
     50                  55                  60
Pro Gly Val Gly Val Pro Gly Val Gly Val Pro Gly Glu Gly Val Pro
 65                  70                  75                  80
Gly Val Gly Val Pro Gly Val Gly Val Pro Gly Val Gly Val Pro Gly
                 85                  90                  95
Val Gly Val Pro Gly Val Gly Val Pro Gly Glu Gly Val Pro Gly Val
            100                 105                 110
Gly Val Pro Gly Val Gly Val Pro Gly Val Gly Val Pro Gly Val Gly
        115                 120                 125
Val Pro Gly Val Gly Val Pro Gly Glu Gly Val Pro Gly Val Gly Val
    130                 135                 140
Pro Gly Val Gly Val Pro Gly Val Gly Val Pro Gly Val Gly Val Pro
145                 150                 155                 160
Gly Val Gly Val Pro Gly Glu Gly Val Pro Gly Val Gly Val Pro Gly
                165                 170                 175
Val Gly Val Pro Gly Val Gly Val Pro Gly Val Gly Val Pro Gly Val
            180                 185                 190
Gly Val Pro Gly Glu Gly Val Pro Gly Val Gly Val Pro Gly Val Gly
        195                 200                 205
Val Pro Gly Val Gly Val Pro Gly Val Gly Val Pro Gly Val Gly Val
    210                 215                 220
Pro Gly Glu Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Glu Gly Val Pro Gly Val Gly Val Pro Gly Val Gly Val Pro Gly Val
            260                 265                 270
Gly Val Pro Gly Val Gly Val Pro Gly Val Gly Val Pro Gly Glu Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Glu Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Glu Gly Val Pro Gly Val
            340                 345                 350
Gly Val Pro Gly Val Gly Val Pro Gly Val Gly Val Pro Gly Val Gly
        355                 360                 365
Val Pro Gly Val Gly Val Pro Gly Glu Gly Val Pro Gly Val Gly Val
    370                 375                 380
Pro Gly Val Gly Val Pro Gly Val Gly Val Pro Gly Val Gly Val Pro
385                 390                 395                 400
Gly Val Gly Val Pro Gly Glu Gly Val Pro Gly Val Gly Val Pro Gly
                405                 410                 415
Val Gly Val Pro Gly Val Gly Val Pro Gly Val Gly Val Pro Gly Val
            420                 425                 430
Gly Val Pro Gly Glu Gly Val Pro Gly Val Gly Val Pro Gly Val Gly
        435                 440                 445
```

-continued

```
Val Pro Gly Val Gly Val Pro Gly Val Gly Val Pro Gly Val Gly Val
    450                 455                 460
Pro Gly Glu Gly Val Pro Gly Val Gly Val Pro Gly Val Gly Val Pro
465                 470                 475                 480
Gly Val Gly Val Pro Gly Val Gly Val Pro Gly Val Gly Val Pro Gly
                485                 490                 495
Glu Gly Val Pro Gly Val Gly Val Pro Gly Val Gly Val Pro Gly Val
            500                 505                 510
Gly Val Pro Gly Val Gly Val Pro Gly Val Gly Val Pro Gly Glu Gly
        515                 520                 525
Val Pro Gly Val Gly Val Pro Gly Val Gly Val Pro Gly Val Gly Val
    530                 535                 540
Pro Gly Val Gly Val Pro Gly Val Gly Val Pro Gly Glu Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Glu Gly Val Pro Gly Val
            580                 585                 590
Gly Val Pro Gly Val Gly Val Pro Gly Val Gly Val Pro Gly Val Gly
        595                 600                 605
Val Pro Gly Val Gly Val Pro Gly Glu Gly Val Pro Gly Val Gly Val
    610                 615                 620
Pro Gly Val Gly Val Pro Gly Val Gly Val Pro Gly Val Gly Val Pro
625                 630                 635                 640
Gly Val Gly Val Pro Gly Glu Gly Val Pro Gly Val Gly Val Pro Gly
                645                 650                 655
Val Gly Val Pro Gly Val Gly Val Pro Gly Val Gly Val Pro Gly Val
            660                 665                 670
Gly Val Pro Gly Glu Gly Val Pro Gly Val Gly Val Pro Gly Val Gly
        675                 680                 685
Val Pro Gly Val Gly Val Pro Gly Val Gly Val Pro Gly Val Gly Val
    690                 695                 700
Pro Gly Glu Gly Val Pro Gly Val Gly Val Pro Gly Val Gly Val Pro
705                 710                 715                 720
Gly Val Gly Val Pro Gly Val Gly Val Pro Gly Val Gly Val Pro Gly
                725                 730                 735
Glu Gly Val Pro Gly Val Gly Val Pro Gly Val Gly Val Pro Gly Val
            740                 745                 750
Gly Val Pro Gly Val Gly Val Pro Gly Val Gly Val Pro Gly Glu Gly
        755                 760                 765
Val Pro Gly Val Gly Val Pro Gly Val Gly Val Pro Gly Val Gly Val
    770                 775                 780
Pro Gly Val Gly Val Pro Gly Val Gly Val Pro Gly Glu Gly Val Pro
785                 790                 795                 800
Gly Val Gly Val Pro Gly Val Gly Val Pro Gly Val Gly Val Pro Gly
                805                 810                 815
Val Gly Val Pro Gly Val Gly Val Pro Gly Glu Gly Val Pro Gly Val
            820                 825                 830
Gly Val Pro Gly Val Gly Val Pro Gly Val Gly Val Pro Gly Val Gly
        835                 840                 845
Val Pro Gly Val Gly Val Pro Gly Glu Gly Val Pro Gly Val Gly Val
    850                 855                 860
Pro Gly Val Gly Val Pro Gly Val Gly Val Pro Gly Val Gly Val Pro
```

-continued

```
                865                 870                 875                 880
Gly Val Gly Val Pro Gly Glu Gly Val Pro Gly Val Gly Val Pro Gly
                    885                 890                 895

Val Gly Val Pro Gly Val Gly Val Pro Gly Val Gly Val Pro Gly Val
                900                 905                 910

Gly Val Pro Gly Glu Gly Val Pro Gly Val Gly Val Pro Gly Val Gly
            915                 920                 925

Val Pro Gly Val Gly Val Pro Gly Val Gly Val Pro Gly Val Gly Val
        930                 935                 940

Pro Gly Glu Gly Val Pro Gly Val Gly Val Pro Gly Val Gly Val Pro
945                 950                 955                 960

Gly Val Gly Val Pro Gly Val Gly Val Pro Gly Val Gly Val Pro Gly
                    965                 970                 975

Glu Gly Val Pro Gly Val Gly Val Pro Gly Val Gly Val Pro Gly Val
                980                 985                 990

Gly Val Pro Gly Val Gly Val Pro  Gly Val Gly Val Pro  Gly Glu Gly
            995                 1000                1005

Val Pro  Gly Val Gly Val Pro  Gly Val Gly Val Pro  Gly Val Gly
    1010                1015                1020

Val Pro  Gly Val Gly Val Pro  Gly Val Gly Val Pro  Gly Glu Gly
    1025                1030                1035

Val Pro  Gly Val Gly Val Pro  Gly Val Gly Val Pro  Gly Val Gly
    1040                1045                1050

Val Pro  Gly Val Gly Val Pro  Gly Val Gly Val Pro  Gly Glu Gly
    1055                1060                1065

Val Pro  Gly Val Gly Val Pro  Gly Val Gly Val Pro  Gly Val Gly
    1070                1075                1080

Val Pro
    1085

<210> SEQ ID NO 40
<211> LENGTH: 605
<212> TYPE: PRT
<213> ORGANISM: Artificial Sequence
<220> FEATURE:
<221> NAME/KEY: PEPTIDE
<222> LOCATION: (1)..(605)
<223> OTHER INFORMATION: Synthetic

<400> SEQUENCE: 40

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                    85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
            115                 120                 125
```

-continued

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
            245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285

Val Pro Gly Val Gly Val Pro Gly Val Gly Val Pro Gly Val Gly Val
    290                 295                 300

Pro Gly Val Gly Val Pro Gly Val Gly Val Pro Gly Val Gly Val Pro
305                 310                 315                 320

Gly Val Gly Val Pro Gly Val Gly Val Pro Gly Val Gly Val Pro Gly
            325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
        355                 360                 365

Val Pro Gly Val Gly Val Pro Gly Val Gly Val Pro Gly Val Gly Val
    370                 375                 380

Pro Gly Val Gly Val Pro Gly Val Gly Val Pro Gly Val Gly Val Pro
385                 390                 395                 400

Gly Val Gly Val Pro Gly Val Gly Val Pro Gly Val Gly Val Pro Gly
            405                 410                 415

Val Gly Val Pro Gly Val Gly Val Pro Gly Val Gly Val Pro Gly Val
            420                 425                 430

Gly Val Pro Gly Val Gly Val Pro Gly Val Gly Val Pro Gly Val Gly
        435                 440                 445

Val Pro Gly Val Gly Val Pro Gly Val Gly Val Pro Gly Val Gly Val
    450                 455                 460

Pro Gly Val Gly Val Pro Gly Val Gly Val Pro Gly Val Gly Val Pro
465                 470                 475                 480

Gly Val Gly Val Pro Gly Val Gly Val Pro Gly Val Gly Val Pro Gly
            485                 490                 495

Val Gly Val Pro Gly Val Gly Val Pro Gly Val Gly Val Pro Gly Val
            500                 505                 510

Gly Val Pro Gly Val Gly Val Pro Gly Val Gly Val Pro Gly Val Gly
        515                 520                 525

Val Pro Gly Val Gly Val Pro Gly Val Gly Val Pro Gly Val Gly Val
    530                 535                 540

```
Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
                565                 570                 575

Val Gly Val Pro Gly Val Gly Val Pro Gly Val Gly Val Pro Gly Val
            580                 585                 590

Gly Val Pro Gly Val Gly Val Pro Gly Val Gly Val Pro
        595                 600                 605
```

<210> SEQ ID NO 41
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Synthetic

<400> SEQUENCE: 41

Gly Gly Val Pro
1

<210> SEQ ID NO 42
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Synthetic

<400> SEQUENCE: 42

Gly Gly Phe Pro
1

<210> SEQ ID NO 43
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 43

Gly Lys Gly Val Pro
1               5

<210> SEQ ID NO 44
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 44

Gly Val Gly Phe Pro
1               5

<210> SEQ ID NO 45
<211> LENGTH: 5
<212> TYPE: PRT
<213> ORGANISM: Artificial Sequence
<220> FEATURE:
<221> NAME/KEY: PEPTIDE

```
<222> LOCATION: (1)..(5)
<223> OTHER INFORMATION: Synthetic

<400> SEQUENCE: 45

Gly Phe Gly Phe Pro
1               5

<210> SEQ ID NO 46
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Synthetic

<400> SEQUENCE: 46

Gly Arg Gly Asp Ser Pro
1               5

<210> SEQ ID NO 47
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Synthetic

<400> SEQUENCE: 47

Gly Val Gly Val Ala Pro
1               5

<210> SEQ ID NO 48
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 48

Gly Glu Gly Val Pro
1               5

<210> SEQ ID NO 49
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 49

Gly Phe Gly Val Pro
1               5

<210> SEQ ID NO 50
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Synthetic

<400> SEQUENCE: 50
```

Gly Gly Ala Pro
1

<210> SEQ ID NO 51
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Synthetic

<400> SEQUENCE: 51

Gly Val Gly Ile Pro
1               5

<210> SEQ ID NO 52
<211> LENGTH: 6
<212> TYPE: PRT
<213> ORGANISM: Artificial Sequence
<220> FEATURE:
<221> NAME/KEY: PEPTIDE
<222> LOCATION: (1)..(6)
<223> OTHER INFORMATION: Synthetic

<400> SEQUENCE: 52

Val Gly Val Ala Pro Gly
1               5

<210> SEQ ID NO 53
<211> LENGTH: 106
<212> TYPE: PRT
<213> ORGANISM: Artificial Sequence
<220> FEATURE:
<221> NAME/KEY: PEPTIDE
<222> LOCATION: (1)..(106)
<223> OTHER INFORMATION: Synthetic

<400> SEQUENCE: 53

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Arg Gly Asp Ser Pro
            100                 105

<210> SEQ ID NO 54
<211> LENGTH: 25
<212> TYPE: PRT
<213> ORGANISM: Artificial Sequence
<220> FEATURE:
<221> NAME/KEY: PEPTIDE
<222> LOCATION: (1)..(25)
<223> OTHER INFORMATION: Synthetic

<400> SEQUENCE: 54

```
Gly Val Gly Val Pro Gly Val Gly Val Pro Gly Lys Gly Val Pro Gly
1               5                  10                 15

Val Gly Phe Pro Gly Phe Gly Phe Pro
            20              25
```

<210> SEQ ID NO 55
<211> LENGTH: 1300
<212> TYPE: PRT
<213> ORGANISM: Artificial Sequence
<220> FEATURE:
<221> NAME/KEY: PEPTIDE
<222> LOCATION: (1)..(1300)
<223> OTHER INFORMATION: Synthetic

<400> SEQUENCE: 55

```
Gly Val Gly Ile Pro Gly Val Gly Ile Pro Gly Val Gly Ile Pro Gly
1               5                  10                 15

Val Gly Ile Pro Gly Val Gly Ile Pro Gly Val Gly Ile Pro Gly Val
            20                  25                 30

Gly Ile Pro Gly Val Gly Ile Pro Gly Val Gly Ile Pro Gly Val Gly
        35                  40                 45

Ile Pro Gly Val Gly Ile Pro Gly Val Gly Ile Pro Gly Val Gly Ile
    50                  55                 60

Pro Gly Val Gly Ile Pro Gly Val Gly Ile Pro Gly Val Gly Ile Pro
65                  70                 75                  80

Gly Val Gly Ile Pro Gly Val Gly Ile Pro Gly Val Gly Ile Pro Gly
                85                  90                 95

Val Gly Ile Pro Gly Val Gly Ile Pro Gly Val Gly Ile Pro Gly Val
            100                 105                110

Gly Ile Pro Gly Val Gly Ile Pro Gly Val Gly Ile Pro Gly Val Gly
        115                 120                125

Ile Pro Gly Val Gly Ile Pro Gly Val Gly Ile Pro Gly Val Gly Ile
    130                 135                140

Pro Gly Val Gly Ile Pro Gly Val Gly Ile Pro Gly Val Gly Ile Pro
145                 150                 155                160

Gly Val Gly Ile Pro Gly Val Gly Ile Pro Gly Val Gly Ile Pro Gly
                165                 170                175

Val Gly Ile Pro Gly Val Gly Ile Pro Gly Val Gly Ile Pro Gly Val
            180                 185                190

Gly Ile Pro Gly Val Gly Ile Pro Gly Val Gly Ile Pro Gly Val Gly
        195                 200                205

Ile Pro Gly Val Gly Ile Pro Gly Val Gly Ile Pro Gly Val Gly Ile
    210                 215                220

Pro Gly Val Gly Ile Pro Gly Val Gly Ile Pro Gly Val Gly Ile Pro
225                 230                 235                240

Gly Val Gly Ile Pro Gly Val Gly Ile Pro Gly Val Gly Ile Pro Gly
                245                 250                255

Val Gly Ile Pro Gly Val Gly Ile Pro Gly Val Gly Ile Pro Gly Val
            260                 265                270

Gly Ile Pro Gly Val Gly Ile Pro Gly Val Gly Ile Pro Gly Val Gly
        275                 280                285

Ile Pro Gly Val Gly Ile Pro Gly Val Gly Ile Pro Gly Val Gly Ile
    290                 295                300

Pro Gly Val Gly Ile Pro Gly Val Gly Ile Pro Gly Val Gly Ile Pro
305                 310                 315                320

Gly Val Gly Ile Pro Gly Val Gly Ile Pro Gly Val Gly Ile Pro Gly
```

-continued

```
                325                 330                 335

Val Gly Ile Pro Gly Val Gly Ile Pro Gly Val Gly Ile Pro Gly Val
                340                 345                 350

Gly Ile Pro Gly Val Gly Ile Pro Gly Val Gly Ile Pro Gly Val Gly
                355                 360                 365

Ile Pro Gly Val Gly Ile Pro Gly Val Gly Ile Pro Gly Val Gly Ile
    370                 375                 380

Pro Gly Val Gly Ile Pro Gly Val Gly Ile Pro Gly Val Gly Ile Pro
385                 390                 395                 400

Gly Val Gly Ile Pro Gly Val Gly Ile Pro Gly Val Gly Ile Pro Gly
                405                 410                 415

Val Gly Ile Pro Gly Val Gly Ile Pro Gly Val Gly Ile Pro Gly Val
                420                 425                 430

Gly Ile Pro Gly Val Gly Ile Pro Gly Val Gly Ile Pro Gly Val Gly
                435                 440                 445

Ile Pro Gly Val Gly Ile Pro Gly Val Gly Ile Pro Gly Val Gly Ile
    450                 455                 460

Pro Gly Val Gly Ile Pro Gly Val Gly Ile Pro Gly Val Gly Ile Pro
465                 470                 475                 480

Gly Val Gly Ile Pro Gly Val Gly Ile Pro Gly Val Gly Ile Pro Gly
                485                 490                 495

Val Gly Ile Pro Gly Val Gly Ile Pro Gly Val Gly Ile Pro Gly Val
                500                 505                 510

Gly Ile Pro Gly Val Gly Ile Pro Gly Val Gly Ile Pro Gly Val Gly
                515                 520                 525

Ile Pro Gly Val Gly Ile Pro Gly Val Gly Ile Pro Gly Val Gly Ile
    530                 535                 540

Pro Gly Val Gly Ile Pro Gly Val Gly Ile Pro Gly Val Gly Ile Pro
545                 550                 555                 560

Gly Val Gly Ile Pro Gly Val Gly Ile Pro Gly Val Gly Ile Pro Gly
                565                 570                 575

Val Gly Ile Pro Gly Val Gly Ile Pro Gly Val Gly Ile Pro Gly Val
                580                 585                 590

Gly Ile Pro Gly Val Gly Ile Pro Gly Val Gly Ile Pro Gly Val Gly
                595                 600                 605

Ile Pro Gly Val Gly Ile Pro Gly Val Gly Ile Pro Gly Val Gly Ile
    610                 615                 620

Pro Gly Val Gly Ile Pro Gly Val Gly Ile Pro Gly Val Gly Ile Pro
625                 630                 635                 640

Gly Val Gly Ile Pro Gly Val Gly Ile Pro Gly Val Gly Ile Pro Gly
                645                 650                 655

Val Gly Ile Pro Gly Val Gly Ile Pro Gly Val Gly Ile Pro Gly Val
                660                 665                 670

Gly Ile Pro Gly Val Gly Ile Pro Gly Val Gly Ile Pro Gly Val Gly
                675                 680                 685

Ile Pro Gly Val Gly Ile Pro Gly Val Gly Ile Pro Gly Val Gly Ile
    690                 695                 700

Pro Gly Val Gly Ile Pro Gly Val Gly Ile Pro Gly Val Gly Ile Pro
705                 710                 715                 720

Gly Val Gly Ile Pro Gly Val Gly Ile Pro Gly Val Gly Ile Pro Gly
                725                 730                 735

Val Gly Ile Pro Gly Val Gly Ile Pro Gly Val Gly Ile Pro Gly Val
                740                 745                 750
```

```
Gly Ile Pro Gly Val Gly Ile Pro Gly Val Gly Ile Pro Gly Val Gly
            755                 760                 765
Ile Pro Gly Val Gly Ile Pro Gly Val Gly Ile Pro Gly Val Gly Ile
    770                 775                 780
Pro Gly Val Gly Ile Pro Gly Val Gly Ile Pro Gly Val Gly Ile Pro
785                 790                 795                 800
Gly Val Gly Ile Pro Gly Val Gly Ile Pro Gly Val Gly Ile Pro Gly
                805                 810                 815
Val Gly Ile Pro Gly Val Gly Ile Pro Gly Val Gly Ile Pro Gly Val
            820                 825                 830
Gly Ile Pro Gly Val Gly Ile Pro Gly Val Gly Ile Pro Gly Val Gly
            835                 840                 845
Ile Pro Gly Val Gly Ile Pro Gly Val Gly Ile Pro Gly Val Gly Ile
    850                 855                 860
Pro Gly Val Gly Ile Pro Gly Val Gly Ile Pro Gly Val Gly Ile Pro
865                 870                 875                 880
Gly Val Gly Ile Pro Gly Val Gly Ile Pro Gly Val Gly Ile Pro Gly
                885                 890                 895
Val Gly Ile Pro Gly Val Gly Ile Pro Gly Val Gly Ile Pro Gly Val
            900                 905                 910
Gly Ile Pro Gly Val Gly Ile Pro Gly Val Gly Ile Pro Gly Val Gly
            915                 920                 925
Ile Pro Gly Val Gly Ile Pro Gly Val Gly Ile Pro Gly Val Gly Ile
    930                 935                 940
Pro Gly Val Gly Ile Pro Gly Val Gly Ile Pro Gly Val Gly Ile Pro
945                 950                 955                 960
Gly Val Gly Ile Pro Gly Val Gly Ile Pro Gly Val Gly Ile Pro Gly
                965                 970                 975
Val Gly Ile Pro Gly Val Gly Ile Pro Gly Val Gly Ile Pro Gly Val
            980                 985                 990
Gly Ile Pro Gly Val Gly Ile Pro  Gly Val Gly Ile Pro  Gly Val Gly
            995                 1000                1005
Ile Pro  Gly Val Gly Ile Pro  Gly Val Gly Ile Pro  Gly Val Gly
    1010                1015                1020
Ile Pro  Gly Val Gly Ile Pro  Gly Val Gly Ile Pro  Gly Val Gly
    1025                1030                1035
Ile Pro  Gly Val Gly Ile Pro  Gly Val Gly Ile Pro  Gly Val Gly
    1040                1045                1050
Ile Pro  Gly Val Gly Ile Pro  Gly Val Gly Ile Pro  Gly Val Gly
    1055                1060                1065
Ile Pro  Gly Val Gly Ile Pro  Gly Val Gly Ile Pro  Gly Val Gly
    1070                1075                1080
Ile Pro  Gly Val Gly Ile Pro  Gly Val Gly Ile Pro  Gly Val Gly
    1085                1090                1095
Ile Pro  Gly Val Gly Ile Pro  Gly Val Gly Ile Pro  Gly Val Gly
    1100                1105                1110
Ile Pro  Gly Val Gly Ile Pro  Gly Val Gly Ile Pro  Gly Val Gly
    1115                1120                1125
Ile Pro  Gly Val Gly Ile Pro  Gly Val Gly Ile Pro  Gly Val Gly
    1130                1135                1140
Ile Pro  Gly Val Gly Ile Pro  Gly Val Gly Ile Pro  Gly Val Gly
    1145                1150                1155
```

```
Ile Pro Gly Val Gly Ile Pro  Gly Val Gly Ile Pro  Gly Val Gly
    1160                1165                 1170

Ile Pro Gly Val Gly Ile Pro  Gly Val Gly Ile Pro  Gly Val Gly
    1175                1180                 1185

Ile Pro Gly Val Gly Ile Pro  Gly Val Gly Ile Pro  Gly Val Gly
    1190                1195                 1200

Ile Pro Gly Val Gly Ile Pro  Gly Val Gly Ile Pro  Gly Val Gly
    1205                1210                 1215

Ile Pro Gly Val Gly Ile Pro  Gly Val Gly Ile Pro  Gly Val Gly
    1220                1225                 1230

Ile Pro Gly Val Gly Ile Pro  Gly Val Gly Ile Pro  Gly Val Gly
    1235                1240                 1245

Ile Pro Gly Val Gly Ile Pro  Gly Val Gly Ile Pro  Gly Val Gly
    1250                1255                 1260

Ile Pro Gly Val Gly Ile Pro  Gly Val Gly Ile Pro  Gly Val Gly
    1265                1270                 1275

Ile Pro Gly Val Gly Ile Pro  Gly Val Gly Ile Pro  Gly Val Gly
    1280                1285                 1290

Ile Pro Gly Val Gly Ile Pro
    1295                1300
```

<210> SEQ ID NO 56
<211> LENGTH: 50
<212> TYPE: PRT
<213> ORGANISM: Artificial Sequence
<220> FEATURE:
<221> NAME/KEY: PEPTIDE
<222> LOCATION: (1)..(50)
<223> OTHER INFORMATION: Synthetic

<400> SEQUENCE: 56

```
Gly Val Gly Ile Pro Gly Val Gly Ile Pro Gly Val Gly Ile Pro Gly
1               5                   10                  15

Val Gly Ile Pro Gly Val Gly Ile Pro Gly Val Gly Ile Pro Gly Val
            20                  25                  30

Gly Ile Pro Gly Val Gly Ile Pro Gly Val Gly Ile Pro Gly Val Gly
        35                  40                  45

Ile Pro
    50
```

<210> SEQ ID NO 57
<211> LENGTH: 111
<212> TYPE: PRT
<213> ORGANISM: Artificial Sequence
<220> FEATURE:
<221> NAME/KEY: PEPTIDE
<222> LOCATION: (1)..(111)
<223> OTHER INFORMATION: Synthetic

<400> SEQUENCE: 57

```
Gly Val Gly Ile Pro Gly Val Gly Ile Pro Gly Val Gly Ile Pro Gly
1               5                   10                  15

Val Gly Ile Pro Gly Val Gly Ile Pro Gly Val Gly Ile Pro Gly Val
            20                  25                  30

Gly Ile Pro Gly Val Gly Ile Pro Gly Val Gly Ile Pro Gly Val Gly
        35                  40                  45

Ile Pro Gly Val Gly Val Pro Gly Arg Gly Asp Ser Pro Gly Val Gly
    50                  55                  60

Ile Pro Gly Val Gly Ile Pro Gly Val Gly Ile Pro Gly Val Gly Ile
```

```
                 65                  70                  75                  80
Pro Gly Val Gly Ile Pro Gly Val Gly Ile Pro Gly Val Gly Ile Pro
                         85                  90                  95
Gly Val Gly Ile Pro Gly Val Gly Ile Pro Gly Val Gly Ile Pro
                100                 105                 110
```

<210> SEQ ID NO 58
<211> LENGTH: 111
<212> TYPE: PRT
<213> ORGANISM: Artificial Sequence
<220> FEATURE:
<221> NAME/KEY: PEPTIDE
<222> LOCATION: (1)..(111)
<223> OTHER INFORMATION: Synthetic

<400> SEQUENCE: 58

```
Gly Val Gly Ile Pro Gly Val Gly Ile Pro Gly Val Gly Ile Pro Gly
1               5                   10                  15

Val Gly Ile Pro Gly Val Gly Ile Pro Gly Val Gly Ile Pro Gly Val
            20                  25                  30

Gly Ile Pro Gly Val Gly Ile Pro Gly Val Gly Ile Pro Gly Val Gly
        35                  40                  45

Ile Pro Gly Val Gly Val Pro Gly Arg Gly Asp Ser Pro Gly Val Gly
    50                  55                  60

Val Pro Gly Val Gly Val Pro Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro
                100                 105                 110
```

<210> SEQ ID NO 59
<211> LENGTH: 45
<212> TYPE: PRT
<213> ORGANISM: Artificial Sequence
<220> FEATURE:
<221> NAME/KEY: PEPTIDE
<222> LOCATION: (1)..(45)
<223> OTHER INFORMATION: Synthetic

<400> SEQUENCE: 59

```
Gly Val Gly Val Pro Gly Val Gly Val Pro Gly Phe Gly Val Pro Gly
1               5                   10                  15

Val Gly Val Pro Gly Val Gly Val Pro Gly Phe Gly Val Pro Gly Val
            20                  25                  30

Gly Val Pro Gly Val Gly Val Pro Gly Phe Gly Val Pro
        35                  40                  45
```

<210> SEQ ID NO 60
<211> LENGTH: 111
<212> TYPE: PRT
<213> ORGANISM: Artificial Sequence
<220> FEATURE:
<221> NAME/KEY: PEPTIDE
<222> LOCATION: (1)..(111)
<223> OTHER INFORMATION: Synthetic

<400> SEQUENCE: 60

```
Gly Val Gly Ile Pro Gly Val Gly Ile Pro Gly Val Gly Ile Pro Gly
1               5                   10                  15

Val Gly Ile Pro Gly Val Gly Ile Pro Gly Val Gly Ile Pro Gly Val
            20                  25                  30
```

Gly Ile Pro Gly Val Gly Ile Pro Gly Val Gly Ile Pro Gly Val Gly
            35                  40                  45

Ile Pro Gly Val Gly Val Pro Gly Arg Gly Asp Ser Pro Gly Val Gly
 50                  55                  60

Val Pro Gly Val Gly Val Pro Gly Lys Gly Val Pro Gly Val Gly Phe
 65                  70                  75                  80

Pro Gly Phe Gly Phe Pro Gly Val Gly Pro Gly Val Gly Val Val Pro
                 85                  90                  95

Gly Lys Gly Val Pro Gly Val Gly Phe Pro Gly Phe Gly Phe Pro
            100                 105                 110

<210> SEQ ID NO 61
<211> LENGTH: 25
<212> TYPE: PRT
<213> ORGANISM: Artificial Sequence
<220> FEATURE:
<221> NAME/KEY: PEPTIDE
<222> LOCATION: (1)..(25)
<223> OTHER INFORMATION: Synthetic

<400> SEQUENCE: 61

Gly Val Gly Val Pro Gly Val Gly Val Pro Gly Val Gly Val Pro Gly
 1               5                  10                  15

Val Gly Val Pro Gly Lys Gly Val Pro
            20                  25

<210> SEQ ID NO 62
<211> LENGTH: 50
<212> TYPE: PRT
<213> ORGANISM: Artificial Sequence
<220> FEATURE:
<221> NAME/KEY: PEPTIDE
<222> LOCATION: (1)..(50)
<223> OTHER INFORMATION: Synthetic

<400> SEQUENCE: 62

Gly Val Gly Val Pro Gly Val Gly Val Pro Gly Lys Gly Val Pro Gly
 1               5                  10                  15

Val Gly Phe Pro Gly Phe Gly Phe Pro Gly Val Gly Val Pro Gly Val
            20                  25                  30

Gly Val Pro Gly Lys Gly Val Pro Gly Val Gly Phe Pro Gly Phe Gly
            35                  40                  45

Phe Pro
 50

<210> SEQ ID NO 63
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic

<400> SEQUENCE: 63
ttcggattcc cgggcgtagg cgtaccgggt                                      30

<210> SEQ ID NO 64
<211> LENGTH: 30
<212> TYPE: DNA
<213> ORGANISM: Artificial Sequence
<220> FEATURE:
<221> NAME/KEY: misc_feature -continued

```
<222> LOCATION: (1)..(30)
<223> OTHER INFORMATION: Synthetic

<400> SEQUENCE: 64
aagcctaagg gcccgcatcc gcatggccca                                    30

<210> SEQ ID NO 65
<211> LENGTH: 10
<212> TYPE: PRT
<213> ORGANISM: Artificial Sequence
<220> FEATURE:
<221> NAME/KEY: PEPTIDE
<222> LOCATION: (1)..(10)
<223> OTHER INFORMATION: Synthetic

<400> SEQUENCE: 65

Phe Gly Phe Pro Gly Val Gly Val Pro Gly
1               5                   10
```

INJECTABLE IMPLANTS FOR TISSUE AUGMENTATION AND RESTORATION

CROSS-REFERENCE TO RELATED APPLICATIONS

This application is continuation of U.S. Ser. No. 09/258,723, filed on Feb. 26, 1999 now abandoned; which claims the benefit of U.S. Provisional Application No. 60/076,297, filed on Feb. 27, 1998 and U.S. Provisional Application No. 60/087,155, filed on May 29, 1998.

ACKNOWLEDGEMENTS

This invention was made with government support under Grant No. R43 HD34659-01 and Grant No. 1R43 HD34999-01 awarded by the National Institutes of Health, National Institute of Child Health and Human Development. The U.S. Government has certain rights in the invention as a result of this support.

TECHNICAL FIELD

The present invention relates to the field of polymeric materials that can be used as implants (injectable or otherwise insertable) in mammals for hard and soft tissue augmentation.

BACKGROUND

A number of methods exist for plastic or reconstructive surgery using injectable implants. The implants have been used for cosmetic reasons, such as filling in dermal creases, and for medical reasons, such as in the treatment of urinary incontinence. Concerning urinary incontinence, this medical condition affects 10 million, mostly elderly, Americans at a cost conservatively estimated at more than $10 billion annually. Clearly, the commercial applications of a successful material or family of materials for tissue augmentation, including urinary incontinence, would be substantial.

An additional example of the potential for soft tissue is seen in the area of intervertebral disc repair. Each year in the U. S. low back pain results in productivity losses that are greater than for any other medical condition and results in health care costs of more than $33 billion. When disability and lost productivity are added, the economic losses exceed $100 billion per year. The common cause of low back pain is pathology of a soft tissue, the intervertebral disc. When disc degeneration occurs, a collapse of the disc space occurs, which leads to neuroforaminal narrowing and nerve impingement. Soft tissue restoration or repair of an injured intervertebral disc could theoretically occur at two levels. One level is to improve the outcome of a discectomy or laminectomy procedure by using materials to prevent the adhesions and fibrosis that result in failed back surgery syndrome. Another level is to use a material to regain the correct disc dimensions and viscoelastic properties and at the same time to provide for cellular attachment where cells can sense the forces that an approximately configured disc would sustain. To date, satisfactory materials for these purposes have not been developed.

Among the materials that have previously received serious consideration as periurethral bulking agents to combat urinary incontinence arising from such conditions as intrinsic sphincter deficiency (ISD) are a synthetic organic polymer, polytetrafluoroethylene (PTFE) (Blaivas and Jacobs, *J. Urol.* 145:1214–1218 (1991); Malizia, et al., *JAMA* 251:3277–3281 (1984)), autologous fat (Santarosa and Blaivas, *J. Urol.* 151:607–611 (1994)), sodium morrhuate (Murless, *J. Obstet. Gynaecol.* 45:67–73 (1938)), and paraffin (Quackels, *Acta. Urol. Belg.* 23:259–262 (1955)). While the initial use of PTFE indicated a 73% improvement rate for stress urinary incontinence (Blaivas and Jacobs (1991)), distant particle migration to the lungs, liver, spleen and brain was subsequently observed with formation of foreign body granulomas (Malizia, et al., supra). Other materials have been reviewed by Canning (*Dial. Ped. Urol.* 14 (1991)). Injectable bioglass has also been considered, but a 16- to 18-gauge needle appears to be required for injection, which results in tissue damage and leakage of the bioglass (Walker, et al., *J. Urol.* 148:645–647 (1992)).

Collagen, a natural component of connective tissue, has also been used for soft tissue augmentation (U.S. Pat. No. 5,428,022; Richardson, et al., *Adult Urology,* 46:378–381 (1995); Frank, et al., *Plastic and Reconstructive Surgery* 87:1080–1088 (1991); WO95/26761), as have polymer conjugates, such as polyethyleneglycol (U.S. Pat. No. 5,476,666). A glyceraldehyde cross-linked bovine dermal collagen with reduced antigenicity and increased resistance to fibroblast-secreted collagenases emerged as a promising material with about 80% of treated patients being either cured or improved after injection with this material (Richardson, et al. (1995); Stricker and Haylen, *The Medical Journal of Australia,* 158:89–91 (1993)). However, recent studies have shown that the cure rate is actually 25%, with 46% of the successful cases needing repeated injections within 3 years, i.e., a cure rate of 10–15% at the 3 year mark. Herschorn, et al., *J. Urol.* 156:1305–1309 (1996). In addition, up to 5% of patients exhibit a hypersensitivity reaction following the required intradermal skin test with this material (Siegle, et al., *Arch. Dermatol.* 120:183–187 (1984)), and are thus not suitable candidates for collagen therapy. The injection results in a mild inflammatory response in which the injected collagen attracts nearly equal amounts of host collagen over a period of about six months, resulting in permanent scarring (Stricker and Haylen (1993)). Such scarring can complicate further efforts at treatment. Furthermore, the material is completely degraded in 9 to 19 months, resulting in a need for repeated injections (Appell, *The Craft of Urological Surgery* 21(1):177–182 (1994)).

Artificial bioelastic polypeptides are a relatively new development that arose in the laboratories of the present inventor and are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746; 4,187,852; 4,589,882; and 4,870,055. U.S. Pat. No. 5,064,430 describes polynonapeptide bioelastomers. Bioelastic polymers are also disclosed in related patents directed to polymers containing peptide repeating units that are prepared for other purposes but which can also contain bioelastic segments in the final polymer: U.S. Pat. Nos. 4,605,413; 4,976,734; and 4,693,718, entitled "Stimulation of Chemotaxis by Chemotactic Peptides"; U.S. Pat. No. 4,898,926, entitled "Bioelastomer Containing Tetra/Pentapeptide Units"; U.S. Pat. No. 4,783,523 entitled "Temperature Correlated Force and Structure Development of Elastin Polytetrapeptide"; U.S. Pat. No. 4,500,700, entitled "Elastomeric Composite Material Comprising a Polypeptide"; U.S. Pat. No. 5,250,516 entitled "Bioelastomeric Materials Suitable for the Protection of Wound Repair Sites"; U.S. Pat. No. 5,527,610 entitled "Elastomeric Polypeptide Matrices for Preventing Adhesion of Biological Materials"; and U.S. Pat. No. 5,336,256 entitled "Elastomeric Polypeptides as Vascular Prosthetic Materials".

A number of other bioelastic materials and methods for their use are described in pending U.S. patent applications, including: U.S. Ser. No. 08/316,802, filed Oct. 3, 1994, entitled "Bioelastomeric Drug Delivery System"; U.S. Ser. No. 08/187,441, filed Jan. 24, 1994, entitled "Photoresponsive Polymers"; U.S. Ser. No. 08/487,594, filed Jun. 7, 1995, entitled "Polymers Responsive to Electrical Energy" and published as PCT/US96/09776; U.S. Ser. No. 08/735,692, filed Oct. 16, 1995 entitled "Bioelastomers Suitable as Food Product Additives" and published as PCT/US96/05266; U.S. Ser. No. 08/542,051 filed Oct. 13, 1995, entitled "Hyperexpression of Bioelastic Polypeptides"; U.S. Ser. No. 08/543,020 filed Oct. 13, 1995, entitled "A Simple Method for the Purification of a Bioelastic Polymer" and published as PCT/US96/05186. All of the aforementioned patents and patent applications are herein incorporated by reference, as they describe in detail bioelastomers and/or components thereof and their preparation.

Artificial bioelastic materials are based on elastomeric and related polypeptides comprised of repeating peptide sequences (Urry, *Angew. Chem.* (German) 105:859–883 (1993); *Angew. Chem. Ont. Ed. Engl.* 32:819–841 (1993)). As a result of work conducted by the present inventor, the bioelastic polypeptides based on VPGVG have been found to be soluble in water below 25° C., but on raising the temperature they associate reversibly to form a dense, water-containing viscoelastic phase in the polypentapeptide ("PPP") and polytetrapeptide ("PTP") cases, whereas the polyhexapeptide ("PHP") associates irreversibly in water to form a granular precipitate, which usually requires the addition of trifluoroethanol to the aggregate for redissolution. The viscoelastic phase is called the coacervate, and the solution above the coacervate is referred to as the equilibrium solution. On cross-linking, the PPP and PTP polymers have been found to be elastomers, whereas the PHP polymer is not elastomeric and appears to provide a means for aligning and interlocking the chains during elastogenesis.

The process of raising the temperature to form the elastomeric state is an inverse temperature transition resulting in the development of a regular dynamic structure, unlike the random network structure of typical rubbers. The regular structure is a β-spiral, a loose water-containing helical structure with β-turns and spacers between turns of the helix which provides hydrophobic contacts between helical turns and has suspended peptide segments. These peptide segments are free to undergo large amplitude, low frequency rocking motions called librations. In addition, several of these β-spirals associate to form twisted filaments. The elastomeric force of these various bioelastomers increases as the regular dynamic structure thereof develops. By synthesizing bioelastic materials having varying mole fraction amounts of the constituent repeating units and by choosing a particular solvent to support the initial viscoelastic phase, it is possible to rigorously control the temperature at which the obtained bioelastomer develops elastomeric force. Maximum elastomeric force develops over a relatively narrow temperature range at temperatures spanning a range of up to about 75° C.

Bioelastic materials have been proposed for a number of uses and apparatuses, as indicated by the general subject matter of the applications and patents set forth above, and have been made available in different physical forms, such as sheets, gels, foams, or powders. For example, compositions can be used in medical applications ranging from the prevention of post-surgical adhesions (Urry, et al., "Biotechnological Polymers: Medical, Pharmaceutical and Industrial Applications", pp. 82–103 (1993)) to programmed drug delivery. See also Urry, "Bioelastic Materials as Matrices for Tissue Reconstruction," in *Tissue Engineering Current Perspectives*, (Eugene Bell. Ed.), Birkhauser Boston, Div. Springer-Verlag, New York, N.Y., pp. 199–206 (1993). Materials functioning as insulator materials for isolating wound repair sites from adhesions, for the protection of burn areas, and to facilitate repair of the damaged tissue have been described in U.S. Pat. Nos. 5,250,516 and 5,527,610.

Despite the numerous techniques that have existed in the past for tissue augmentation, all of the existing techniques have suffered from one deficiency or another that have resulted in less than optimal results for the patient. There remains a need for biocompatible implants, especially injectable implants, for tissue augmentation, and the present invention provides compositions and methods for meeting those needs that do not suffer from the deficiencies of prior techniques.

SUMMARY OF THE INVENTION

It is an object of the invention to provide long-lasting implants for tissue augmentation or restoration.

It is also an object to provide implants that are injectable under a variety of surgical conditions, including emplacement during endoscopic surgery and related techniques.

It is a further object to provide for implants that match the compliance of the tissue site of application and that can be selected to match different compliance values with a minimum of difficulty.

It is yet another object to provide an implant that has both a carrier polymer that is biologically inert or at least degradable to non-toxic products, and a biologically active component.

It is another object of the invention to provide an implant that is readily sterilizable as well as being biocompatible, eliciting insignificant immunogenic and antigenic responses in the host.

It is a further object of the invention to provide an implant that, in biological situations involving implantation of exogenous material into a tissue, as in tissue regeneration or restoration, can stimulate cell adhesion and resulting cell growth upon appropriate modification or additions to the basic structure of the composition.

It is yet another object of the invention to provide a method for tissue augmentation, such as in plastic surgery (e.g., wrinkle removal) or to correct medical conditions (e.g., urinary incontinence or back pain resulting from degenerative defects in intervertebral discs).

These and other objects of the invention are achieved by providing a method for tissue augmentation in a warm-blooded animal comprising injecting a polymer at the tissue site in need of augmentation, which site has a tissue temperature, said polymer comprising repeating peptide monomeric units selected from the group consisting of nonapeptide, pentapeptide and tetrapeptide monomeric units, wherein said monomeric units form a series of β-turns separated by dynamic bridging segments suspended between said β-turns, wherein said polymer has an inverse temperature transition $T_t$ less than said tissue temperature, and wherein said polymer is injected as a water solution at coacervate concentration in the substantial absence of additional water. The monomeric units can all be the same or they may be different. In specific embodiments, tissue reconstruction can be advantageously achieved using a polymer having the same elastic modulus of the natural tissue being augmented and, in some case, having the capability to induce natural cells of the tissue (or surrounding tissue) to enter and to function at the site of reconstruction.

Further objects of the invention are achieved by providing a method for tissue restoration of intervertebral discs in a mammal, said method comprising: injecting a polymer into the depleted nucleus pulposus site, which has a site temperature, said polymer comprising repeating peptide monomeric units selected from the group consisting of nonapeptide, pentapeptide and tetrapeptide monomeric units, wherein said monomeric units form a series of β-turns separated by dynamic bridging segments suspended between said β-turns, wherein said polymer has an inverse temperature transition $T_t$ less than said site temperature, and wherein said polymer is injected as a water solution at coacervate concentration in the substantial absence of additional water and swells to increase the pressure within the disc.

The injectable protein-based polymers as taught herein can be designed to have numerous advantages including biological stability, biological function, and defined polymer size. These advantages are achieved by providing polymers composed of easily obtained and coupled monomer units, e.g. amino acids, that are themselves diverse in structure and in chemical properties and are readily modified. Furthermore, recombinant peptide-engineering techniques can be advantageously used to produce specific peptide backbones, either in bioelastic units or non-elastic biofunctional segments. Thus, the polymer can be present as a copolymer containing a mixture of tetrameric, pentameric or other monomeric units.

The polymers can be prepared with widely different water compositions, with a wide range of hydrophobicities, with almost any desired elastic modulus, and with a variable degree of cross-linking by selecting different amino acids for the different positions of the monomeric units and by varying the cross-linking process (e.g. chemical, enzymatic, or radiation) used to form the final product. Preparation of a variety of polymers that can be used in the present invention has already been described, for example in the publications discussed above, and the preparation of the polymers themselves is now established and not a novel part of the present invention, although the preparation of these materials as injectable formulations for use in tissue augmentation is new. Additionally, there are some preferred embodiments of polymers that can be prepared as described herein that are themselves new. For the most part, however, the invention involves the application of existing polymers (as well as new polymers) to a new field where they have not been used before.

BRIEF DESCRIPTION OF THE DRAWINGS

The invention will be better understood by reference to the following detailed description of specific embodiments together with the figures that form part of this specification, wherein:

FIG. 1 illustrates an oligonucleotide sequence (SEQ ID NO:1) encoding the bioelastic polymer protein sequence made up of the repeating [(GGVP)$_3$ GGFP (GGVP)$_3$ GGFP (GGVP)$_3$ GGFP] (SEQ ID NO:9) unit, and shows the encoded protein sequence and restriction enzyme sites.

FIG. 2 illustrates an oligonucleotide sequence (SEQ ID NO:2) encoding the bioelastic polymer protein sequence (GVGVP)$_2$ GKGVP GVGVP GVGFP GFGFP (SEQ ID NO: 10) and restriction enzyme sites.

FIG. 3 illustrates an oligonucleotide sequence (SEQ ID NO:3 and 4) encoding the bioelastic polymer protein sequence VGVP GRGDSP G (SEQ ID NO:11).

FIG. 4 illustrates an oligonucleotide sequence (SEQ ID NO:5) encoding the bioelastic polymer protein sequence (GVGVP)$_3$ GKGVP (GVGVP)$_2$ (SEQ ID NO: 12).

FIG. 5 illustrates an oligonucleotide sequence (SEQ ID NO:6) encoding the bioelastic polymer protein sequence (GVGVP)$_{10}$ GVGVPGRGDSP (GVGVP)$_{10}$ (SEQ ID NO: 13).

FIG. 6 illustrates an oligonucleotide sequence (SEQ ID NO:7) encoding the bioelastic polymer protein sequence (GVGVP)$_{10}$ (GVGVAP)$_8$ (GVGVP)$_{10}$ (SEQ ID NO:14).

FIG. 7 illustrates an oligonucleotide sequence (SEQ ID NO:8) encoding the bioelastic polymer protein sequence (GVGVP)$_3$ GEGVP (GVGVP)$_2$ (SEQ ID NO:15).

FIG. 8 illustrates the sequence of oligonucleotide adapters useful in cloning bioelastic polymer genes and are identified as SEQ ID NOS:30, 31, 32 and 33.

DESCRIPTION OF SPECIFIC EMBODIMENTS

Figures 9, 10:
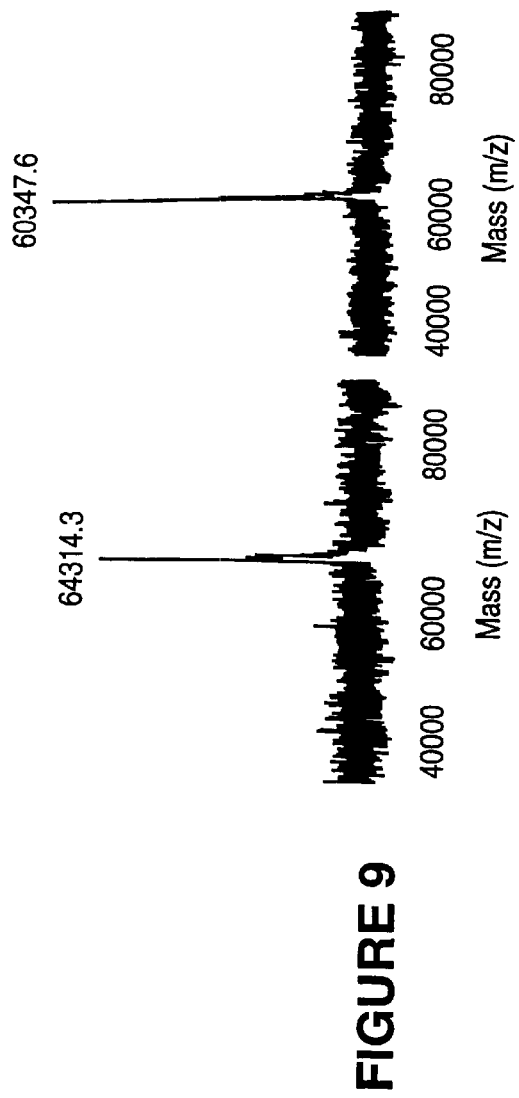
FIG. 9 is a mass spectra plot of polymers III and IV.
FIG. 10 illustrates the sequence of oligonucleotide adapters useful in cloning bioelastic polymer genes and are identified as SEQ ID NOS:63 and 64.

The process of soft tissue augmentation has typically been achieved in the past using synthetic polymers or collagen derivatives. The prior art methods involving synthetic polymers, such as PTFE (polytetrafluoroethylene), have distinct disadvantages in that synthetic polymers are recognized by the body as foreign material and PTFE promotes granuloma formation. Although collagen derivatives have been used with some success, they need to be injected with excess water, resulting in complications arising from the subsequent decrease in filling volume. In addition, collagen derivatives degrade and promote scar tissue formation over time. These and other disadvantages of the prior art materials used in tissue augmentation are overcome in the present invention by the use of injectable bioelastic polymers as implants. The methods of collagen injection, however, can in the most part be applied directly to methods of using the present compositions for tissue augmentation, subject to the variations described herein.

The defined structure of the artificial bioelastic polymers used in the invention allow polymers to be designed and synthesized with chosen physical properties, rather than having to rely on the less controllable properties of materials prepared from natural products. It should be noted that the terms "bioelastic polymers", "bioelastomeric polymers," and "bioelastomers" are used interchangeably herein and further that these terms encompass materials that may not be thought of as elastomers (such as certain polymers having the characteristics of plastics), since the term "bioelastomer" has come to be an art-recognized term describing polymers comprising repeating peptide monomeric units selected from the group consisting of nonapeptide, pentapeptide and tetrapeptide monomeric units, where the monomeric units form a series of β-turns separated by dynamic bridging segments suspended between the β-turns. Examples of these materials (in their prior embodiments) are described in the numerous publications, including patents, that are listed above and that are incorporated herein by reference.

The bioelastomers can be described either generically, as above, or with various degrees of specificity. The generic descriptions have been sufficient for the inclusion in claims of a number of issued U.S. and foreign patents. However, a number of subgeneric and specific descriptions will be provided for those less familiar with bioelastomers.

One is to describe a grouping of these materials that contain ionizable amino acid residues (used for purposes described below) as containing repeating units of the formula αPρΩG or VPθδ, wherein:

V is a peptide-forming residue of L-valine;

P is a peptide-forming residue of L-proline;

G is a peptide-forming residue of glycine;

α is a peptide-forming residue of L-valine, L-leucine, L-isoleucine, L-phenylalanine or an ionizable peptide-forming residue selected from the group consisting of the residues of L-Glu, L-Asp, L-His, L-Lys, L-Tyr, and other ionizable peptide-forming L-amino acids;

ρ is a peptide-forming residue of glycine or a peptide-forming residue of D-Glu, D-Asp, D-His, D-Lys, D-Tyr, or (optionally) other ionizable peptide-forming D-amino acids for the elastic polymeric repeats or any L-amino acid for the elastic forming repeats;

θ is a peptide-forming residue of L-valine, L-leucine, L-isoleucine, L-phenylalanine or (optionally) an ionizable peptide-forming L-amino acids;

Ω is a peptide-forming residue of glycine or a peptide-forming residue of D-Glu, D-Asp, D-His, D-Lys, D-Tyr, or (optionally) another ionizable peptide-forming D-amino acid; and δ is a peptide-forming residue of glycine or a peptide-forming residue of L-Glu, L-Asp, L-His, L-Lys, L-Tyr, or (optionally) another ionizable peptide-forming L-amino acid.

More generally, bioelastic polypeptide polymers generally comprise repeating elastomeric units selected from the group consisting of bioelastic pentapeptides and tetrapeptides, where the repeating units comprise amino acid residues selected from the group consisting of hydrophobic amino acid and glycine residues and where the repeating units exist in a conformation having a β-turn of the formula:

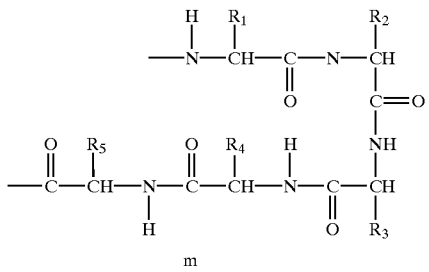

wherein $R_1$–$R_5$ represent side chains of amino acid residues 1–5, and m is 0 when the repeating unit is a tetrapeptide or 1 when the repeating unit is a pentapeptide. Nonapeptide repeating units generally consist of sequential tetra- and pentapeptides. Preferred hydrophobic amino acid residues are selected from the group consisting of alanine, valine, leucine, isoleucine, proline, phenylalanine, tryptophan, and methionine. In many cases, the first amino acid residue of the repeating unit is a residue of valine, leucine, isoleucine or phenylalanine; the second amino acid residue is a residue of proline; the third amino acid residue is a residue of glycine; and the fourth amino acid residue is glycine or a very hydrophobic residue such as tryptophan, phenylalanine or tyrosine.

A particularly useful tetrapeptide is Val-Pro-Gly-Gly (SEQ ID NO:16). Also useful are GGVP (SEQ ID NO:41), GGFP (SEQ ID NO:42) and GGAP (SEQ ID NO:50). A particularly useful pentapeptide is Val-Pro-Gly-Val-Gly (SEQ ID NO:17). Also useful are GVGVP (SEQ ID NO:20), GKGVP (SEQ ID NO:43), GVGFP (SEQ ID NO:44), GFGFP (SEQ ID NO:45), GEGVP (SEQ ID NO:48), GFGVP (SEQ ID NO:49) and GVGIP (SEQ ID NO:51). For other specifically preferred individual monomeric units and bioelastomers, see any of the patents that are herein incorporated by reference.

The bioelastomers of the invention can consist of only nonamers (a polynonapeptide), tetramers (a polytetrapedptide), only pentamers (a polypentapeptide) or a mixture of these units, but more typically a mixture of tetrapeptide and pentapeptide units (a copolymer). In addition, the bioelastomer can be a copolymer formed from one of the aforementioned monomeric units and a second peptide unit containing 1–100 amino acids, more typically 1–20 amino acids. On the smaller side, this second peptide can be for example, the fibronectin cell attachment sequence, GRGDSP (SEQ ID NO:46) or a monomer such as GVGVAP (SEQ ID NO:47) or VGVAPG (SEQ ID NO:52), which is a chemoattractant for fibroblasts and monocytes. On the larger side (90–100 amino acids), the second peptide can be a cell attachment sequence from the Type-III domains of fibronectin, vitronectin, tenascin, titin or other related cell attachment protein, which sequence provides more specific cell attachment than the somewhat non-specific GRGDSP cell attachment sequence.

In one aspect, the present invention provides injectable bioelastic polymers and methods for their preparation and use, where the polymers are selected for and exhibit specific desired properties for tissue augmentation. For example, the polymers preferably exhibit biocompatibility, extrusibility through a fine surgical needle (e.g., 22-gauge) at the temperature of use, as well as insignificant volume change after injection. The later characteristic is important, since the preferred coaptation (extent of filling) at the treated site can be assessed visually at the time of injection, for example, by cystoscopical examination, without the need to consider subsequent increases or decreases in filling volume and related complications. The bioelastic polymers can also be designed to remain at the site of injection, and to provide long-lasting tissue augmentation, as is described in more detail below.

In another aspect, the present invention provides injectable bioelastic polymers and methods for their preparation and use, where the polymers are selected for and exhibit specific desired properties for tissue restoration in the area of intervertebral disc repair. For example, as for tissue augmentation applications, the polymers preferably exhibit biocompatibility. However, for disc repair, the polymers are more viscous at the temperature of use and are injected through a larger bore such as is present in equipment used in endoscopic or percutaneous discectomy procedures, as well as exhibiting a significant volume change after injection by swelling. Certain polymers are preferred for this application, especially those polymers containing one or more pentapeptide units such as GVGIP (SEQ ID NO:51) or one or more monomers that contain one or more, typically one or two, aromatic residues such as phenylalanine, for example, GVGFP (SEQ ID NO:44), GFGFP (SEQ ID NO:45), and GFGVP (SEQ ID NO:49).

"Injectable" as used herein relates to materials having a texture and viscosity which permits their flow through a suitable surgical needle or other surgical instrument, such as a equipment used in endoscopic or percutaneous discectomy procedures, by employing typical injection pressures. For example, an injectable material of low viscosity can be forced through at least the diameter of a 22-gauge needle.

Injectable materials of high viscosity can be introduced, for example, by first making a hole in the annulus with a trocar, then forcing the bioelastomer through the bore of large syringe, i.e., a syringe of about 13 to 19-gauge, under normal pressure applicable by the hand and fingers of a surgeon. The mixture is injected directly into the site in need of augmentation, such as dermis (subdermal), intervertebral disc, periurethral, tendon or cartilage, and causes essentially no detectable inflammation or foreign body reaction.

"Augmentation" means the repair, prevention, or alleviation of defects, particularly defects due to loss or absence of tissue, by providing, augmenting, or replacing such tissue. While the invention is primarily designed for soft tissue augmentation, hard tissue augmentation is encompassed as well since the injectable compositions of the invention can be used in combination with, for example, materials to promote mineralization or bone formation, as described elsewhere.

In its broadest aspect, the present invention provides a method for tissue augmentation in a warm-blooded animal by injecting a bioelastic polymer at a tissue site in need of augmentation. The method will often be applied to humans, but one can also readily understand that the present method is applicable to agriculturally important animals, including mammals, such as cattle, horses, pigs, and sheep, and other animals such as chickens, turkeys, and geese (as for example in providing for repair of breeding stock that has suffered a traumatic injury), as well as domestic animals of interest, such as cats and dogs.

In another embodiment of the invention, the method for tissue augmentation or restoration in a mammal, comprises the steps of a) identifying a tissue site in need of tissue augmentation or restoration, such site having a site temperature ($T_s$); and b) injecting a polymer at the site, said polymer comprising repeating peptide monomeric units selected from the group consisting of pentapeptide and tetrapeptide monomeric units, alone or in combination, wherein the monomeric units form a series of β-turns separated by dynamic bridging segments suspended between the β-turns, and wherein (i) the polymer has an inverse temperature transition $T_t$ less than $T_s$, (ii) the polymer is injected as a water solution at coacervate concentration in the substantial absence of additional water, and (iii) the coacervate has a viscosity at $T_s$ of 1 to 100,000 millipoise.

Bioelastic polymers are high molecular weight polymers of repeating peptide sequences and are the subject of numerous patents and patent applications from the laboratories of the present inventor, as described in the Background Section. Bioelastomers exhibit inverse temperature transitions in the form of a phase separation in which folding and aggregation of water-soluble polymer chains into more-ordered states of the condensed (coacervate) phase occur on raising the temperature. Although the prior patents and applications have not been concerned with injectable compositions for tissue augmentation, they provide considerable guidance on biocompatibility and on manufacturing of bioelastomers to obtain useful structural features for the uses described herein.

Particularly preferred bioelastic materials are those based on elastomeric tetrapeptide, pentapeptide, and nonapeptide monomers or monomeric units, as these materials have already been demonstrated to be biocompatible. The elasticity of the monomeric units is believed to be due to a series of β-turns in the protein's secondary structure, i.e., the conformation of its peptide chain separated by dynamic (as opposed to rigid) bridging segments suspended between the β-turns. Typical polymers contain at least 5, preferably at least 10, more preferably at least 20 monomers, and because of limited solubility in aqueous solvents, which are desirable for biological uses, usually contain fewer than 1000, usually fewer than 500, of such units.

Injectable bioelastic polymers are soluble in water at all proportions at a sufficiently low temperature, but on raising the temperature above a critical value, designated as $T_t$, they fold, assemble and phase separate into a more ordered state of predetermined composition, such as on the order of 50% peptide/50% water by weight. However, this value does vary and a broad range is acceptable for use in the applications of the invention. For example, polymers containing the pentapeptide monomer, GVGVP, have been shown to have a resultant ordered state of 40 wt % peptide/60 wt % water, while polymers containing GVGIP have a resultant ordered state of 60 wt % peptide/40 wt % water. This phase separation is referred to as an inverse temperature transition and the more-dense phase is called a coacervate.

The transition temperature of the particular bioelastic polymer is preferably selected to be below the normal temperature of the tissue in which the composition will be injected, which will vary slightly with the location of the tissue, as is well known. Skin, for example, in humans has a slightly lower temperature than internal tissues. Thus, most of the time $T_t$ will be selected to be less than 37° C., preferably below 35° C., more preferably below 30° C., even more preferably below 25° C. and most preferably below 20° C. to provide a stable coacervate. Preparation of a bioelastomer with a pre-selected $T_t$ of 25° C. has been previously described on numerous occasions. Table I delineates the $T_t$-based hydrophobicity scale which may be used to change an otherwise non-functional residue to return the transition temperature where desired. Thus, Table 1 represents a scale for protein engineering.

TABLE 1

$T_t$-Based Hydrophobicity Scale for Protein Engineering
Using Poly[$f_v$(ValProGlyValGly),$f_x$(ValProGly-X-Gly)]

| Residue X | One Letter Code | $T_t$, linearly extrapolated to $f_x = 1$ |
|---|---|---|
| Lys(NMeN, reduced)[a] | | −130°C. |
| Trp | (W) | −90°C. |
| Tyr | (Y) | −55°C. |
| Phe | (F) | −30°C. |
| His(imidazole) | (H°) | −10°C. |
| Pro | (P)[b] | (−8°C.) |
| Leu | (L) | 5°C. |
| Ile | (I) | 10°C. |
| Met | (M) | 20°C. |
| Val | (V) | 24°C. |
| Glu(COOCH$_3$) | (Em) | 25°C. |
| Glu(COOH) | (E°) | 30°C. |
| Cys | (C) | 30°C. |
| His(imidazolium) | (H$^+$) | 30°C. |
| Lys(NH$_2$) | (K°) | 35°C. |
| Pro | (P)[c] | 40°C. |
| Asp(COOH) | (D°) | 45°C. |
| Ala | (A) | 45°C. |
| HyP | | 50°C. |
| Asn | (N) | 50°C. |
| Ser | (S) | 50°C. |
| Thr | (T) | 50°C. |
| Gly | (G) | 55°C. |
| Arg | (R) | 60°C. |
| Gln | (Q) | 60°C. |
| Lys(NH$^+_3$) | (K$^+$) | 120°C. |
| Tyr(φ-O$^-$) | (Y$^-$) | 120°C. |
| Lys(NMeN, oxidized)[a] | | 120°C. |

TABLE 1-continued $T_t$-Based Hydrophobicity Scale for Protein Engineering
Using Poly[$f_v$(ValProGlyValGly),$f_x$(ValProGly-X-Gly)]

| Residue X | One Letter Code | $T_t$, linearly extrapolated to $f_x = 1$ |
|---|---|---|
| Asp(COO⁻) | (D⁻) | 170°C. |
| Glu(COO⁻) | (E⁻) | 250°C. |
| Ser(PO⁻₄) | | 1000°C. |

[a]NMeN represents N-methyl nicotinamide pendant on a lysyl side chain, that is, N-methyl nicotinate attached by amide linkage to the -ω-NH₂ of Lys; the reduced state is N-methyl-1,6-dihydronicotinamide.
[b]The calculated $T_t$ value for Pro comes from poly(VPGVG) when the experimental values of Val and Gly are used. This hydrophobicity value of −8° C. is unique to the β-spiral structure in which there is hydrophobic contact between the Val¹—CH₃ and Pro²—CH₂ moieties.
[c]The experimental value determined from poly[$f_v$(VPGVG),$f_p$(PPGVG)]

Virtually every variable can, with the appropriate composition of the protein-based polymer, change the value of $T_t$. Such variables include, among other criteria, (1) polymer concentration, (2) polymer length, (3) amino acid composition, (4) presence of salts e.g. the Hofmeister (Lyotropic) Series, (5) organic solutes and solvents, (6) polymer side-chain ionization, (7) chemical modification of polymer side-chains e.g. phosphorylation or nitration, (8) pressure e.g., as effecting aromatic residues, (9) redox state of chemical groups attached to the polymer, (10) light absorption by chemical groups attached to the polymer, and (11) side chain neutralization by ion pairing e.g., cation neutralization of anionic side chains, anion neutralization of cationic side chains, and ion-pairing between side chains.

Bioelastomers for use in the practice of the invention can be readily prepared at an appropriate viscosity, although this has not previously been of interest in the preparation of these materials. Typically, the coacervate has a viscosity at the tissue site temperature of 1 to 100,000 millipoise. By selection of the monomers used, the length of the polymer chains, and the amount of crosslinking (as is well known in the polymer art), viscosity can be readily controlled. In fact, a wide range of viscosity can be used depending upon the particular application. For example, it is desirable to have the viscosity of the coacervate sufficiently low to allow reasonable control of syringe being used by a physician or other individual to inject the polymer into the desired tissue location for tissue augmentation. On the other hand, for tissue restoration such as in intervertebral disc restoration, a higher viscosity is desired when the polymer is to be injected through a larger syringe.

The injectability of the polymer is usually controlled by the viscosity of the coacervate concentration, which is the form in which injection usually takes place. Measurement of viscosity is not required, however, as suitability can be readily assessed by simply attempting to extrude any previously unused composition from the syringe to be used through a needle of the appropriate size. For example, the polypentapeptide (GVGVP)$_{251}$ (SEQ ID NO: 18) is extrusible through a 22 and even a 27 gauge needle at 37° C., after having been initially dissolved at 4° C. at a concentration of 500 mg/ml (and after expelling of excess water from the coacervate, as described below). Preferred bioelastic materials for use in the tissue augmentation and restoration aspects of the present invention include polytetrapeptides, such as poly[0.6(GGVP),0.4(GGFP)] (SEQ ID NOS:41 and 42), which are extrusible through both 22 and 27 gauge needles at 37° C. and remain extrusible for sufficient time (weeks to months) to allow storage of the polymer in ready-to-use form. Preferred bioelastic materials for use in the restoration of intervertebral discs will have thicker viscosities, typically exhibiting an elastic modulus within the range of $5 \times 10^4$ to $5 \times 10^6$ N/m² at the temperature at the disc site. It may be desirable to approximate the elastic modulus of the vascular wall of the femoral artery, which is about $5 \times 10^5$ N/m², and even more preferable to approximate the elastic modulus of the nucleus pulposus, which is less than $5 \times 10^5$ N/m². Although particular polymer systems are mentioned illustratively here and elsewhere, it will be recognized that such a description is not limiting of the invention, as these and other examples can be readily modified to provide numerous compositions that have the desired properties for tissue augmentation as discussed herein.

Polymers are injected in the method of the invention in a coacervate composition from which all, or substantially all, of the excess water has been excluded. As previously noted, the coacervate state of the polymers used in this method is essentially a viscoelastic state containing a fixed ratio of water and polymer. Excess water present from the initial dissolution of polymer into water at a temperature below $T_t$, usually 4° C., is readily removed from this solid phase by any of the techniques available for separating phase separated states from supernatant water. The coacervate therefore provides a stable volume under physiological conditions, allowing a polymer to be injected from a suitable surgical needle without being subject to volume changes at the injection site after injection, as occurs with injections of collagen, which require the presence of excess water. A plastic surgeon can therefore readily assess the amount of polymer to be injected by observation without having to estimate later shrinkage of the injection site caused by water leakage from the site.

It will of course be recognized that some amount of excess water can remain with the coacervate without detracting from the practice of the invention, as long as the amount is not sufficient to impair the injection of the coacervate. For example, as much as 30% (by volume) excess water can be present if the surgeon is willing to make adjustments in the injected volume to anticipate the final volume, although no more than 20% excess water is preferred, more preferably no more than 10%, and most preferably no more than 5.

As with all bioelastic polymers, transition to the coacervate state can occur without a change in temperature but under the control of other environmental factors. This is referred to as the $\Delta T_t$ mechanism of transition (U.S. Ser. No. 08/187,441; Urry et al., *Biopolymers* 24:2345–2346 (1985), herein incorporated by reference) and can be achieved by changing a number of intrinsic or extrinsic factors. Intrinsic to a class of model proteins of 50,000 Da molecular weight or greater are the following: (a) the concentration of polymer itself, (b) changes in the amino acid composition within the polymeric bioelastic unit, (c) changes in the degree of ionization of functional side chains controlled by changes in pH, (d) the phosphorylation of side chains such as serine by enzymes called kinases, (e) the oxidation or reduction electrically, chemically or enzymatically of a side chain attached to the polymer, and (f) chemical reactions of side chains, for example in response to electromagnetic radiation. Extrinsic chemical changes affecting $T_t$ include the effects of salts, organic solutes and solvents. In addition, there is a chain length dependence that becomes significant at lower molecular weights where a polymer having shorter peptide chain lengths exhibit higher values of $T_t$ relative to a polymer having longer peptide chain lengths.

Thus, bioelastomers can be rationally designed in order to achieve the desired properties appropriate for the methods of the invention. The choice of individual amino acids from which to synthesize the elastomeric units and resulting polypeptide is unrestricted so long as the resulting structure comprises elastomeric structures with features described, for example, in U.S. Pat. Nos. 4,474,851 and 5,064,430, herein incorporated by reference, particularly β-turn formation and the resulting polymer maintains attributes useful for purposes intended according to the embodiments of the invention including, among other things, extrusibility through fine gage needles.

In general, selection of the sequence of amino acids in a particular monomeric unit and selection of the required proportion of monomeric units can be accomplished by an empirical process that begins with determining (or looking up) the properties of known bioelastomers, making similar but different bioelastomers and measuring the transition temperature and physical properties as described herein and in the cited patents and patent applications. The effect of changing the amino acid composition on the value of $T_t$ can also be determined using a hydrophobicity scale described in detail in U.S. patent application Ser. No. 08/187,441. For example, a rough estimate of the likely transition temperature can be obtained by summing the mean hydrophobicities of the individual amino acid residues in the monomeric units of the polymer and comparing the result to the sum obtained for polymers having known transition temperatures. Typically, more hydrophobic residues (e.g., Ile, Phe) lower $T_t$, whereas less hydrophobic residues (e.g., Ala, Gly) and polar residues (e.g., Asp, Lys) raise $T_t$.

Any chemical means of changing the mean hydrophobicity of the polymer, such as dephosphorylation/phosphorylation, reduction/oxidation of a redox couple, ionization/deionization, protonation/deprotonation, cleavage/ligation, amidation/deamidation, a conformational or a configurational change (e.g., cis-trans isomerization), an electrochemical change (e.g., pKa shift), emission/absorbance, or other physical change (e.g., heat energy radiation/absorbance), or pressure, or combinations thereof can be used to bring about transition. U.S. Pat. No. 5,226,292 from the laboratory of the present inventor details pressure-related effects, U.S. Ser. No. 08/187,441, photoresponsive effects, and U.S. Ser. No. 08/487,594, electroresponsive effects, each of which can be used to effect transition.

A major advantage of the bioelastic polypeptides is the extent to which fine-tuning of the degree of hydrophobicity/polarity and resulting shift in the inverse temperature transition can be achieved. For example, the hydrophobicity of the overall polymer (and therefore the average hydrophobicity of functional groups present in the polymer) can be modified by changing the ratio of different types of monomeric unit. These can be monomeric units containing a functional group undergoing the transition or other monomeric units present in the polymer. For example, if the basic monomeric unit is VPGVG (SEQ ID NO:17) and the unit undergoing transition is VPGXG (SEQ ID NO:19); where X is an amino acid residue modified to have an electroresponsive side chain, either the ratio of VPGVG unit to VPGXG units can be varied or a different structural unit, such as IPGVG, can be included in varied amounts until the appropriate transitions temperature is achieved. Furthermore the regularity of structure of the protein and protein-based bioelastic polymers allows optimal arrangement of the structural components. For example, optimal spatial proximity can be achieved by placing coupled residues adjacent to each other in the backbone (i.e., based on primary sequence) and also by positioning to provide inter-turn proximity.

The bioelastic polymers are composed of peptide units that form a matrix which can be modified in a variety of ways to obtain additional properties. For example, one or more of the peptide bonds can be optionally replaced by substitute linkages such as those obtained by reduction or elimination. Thus, one or more of the —CONH— peptide linkages can be replaced with other types of linkages such as —CH$_2$NH—, —CH$_2$S—, CH$_2$CH—, —CH=CH— (cis and trans), —COCH$_2$—, —CH(OH)CH$_2$—, and —CH$_2$SO—, by methods known in the art, for example, see Spatola, A. F. (1983) in *Chemistry and Biochemistry of Amino Acids, Peptides and Proteins* (B. Weinstein, ed.) Marcel Dekker, New York, p. 267 for a general review. Amino acid residues are preferred constituents of these polymer backbones. Of course, if backbone modification is made in the elastomeric units, then suitable backbone modifications are those in which the elasticity and inverse temperature transition of the polymer is maintained.

As is apparent to one of ordinary skill in the art, the physical properties of the bioelastic polymer can be adjusted as described above, to exhibit desired characteristics, for example, viscosity, consistency, modulus of elasticity, stability, and the like. For example, the parent elastic protein-based polymer (GVGVP)$_n$ (SEQ ID NO:20), when prepared with n on the order of 200 and when cross-linked with 20 Mrads of γ-irradiation (described below), forms an elastic matrix with an elastic modulus approximating that of natural vascular wall, in the range of $10^5$ N/m$^2$. By variations in composition and conditions, the elastic modulus can be varied from $10^4$ to $10^8$ N/m$^2$. This provides the capacity to match compliance over the wide range of biological soft tissues. In other embodiments, the primary sequence of the polypeptide can be designed to elicit fibrous capsule formation thus maintaining the polymer at the site of injection. A particular polymer can be assessed for its ability to promote fibrous capsule formation by methods known in the art, e.g., visually after a period of implantation in a test subject. In a preferred embodiment, an illustrative polymer that does not elicit fibrous capsule formation is X$^{20}$-poly(GVGVP) (Urry, et al., *J. Bioactive Compatible Polym.* 6:263–282 (1991)). Polymers described in this specification that are prepared by irradiation cross-linking are identified as, for example, "X$^{20}$-polyVPGVP," which refers to a polymer prepared from VPGVG pentapeptide units which has been irradiated with a 20 Mrad dose of cobalt-60 radiation to form the cross-links, thus resulting in an insoluble matrix. Injectable, cross-linked coacervates would be obtained by much lower radiation dosages, usually less than 20 Mrad, often less than 10 Mrad, and even less than 5 Mrad.

In another preferred embodiment, a polymer that comprises phenylalanine (Phe, F) residues, such as X$^{20}$-poly [0.75(GVGVP), 0.25(GFGVP)] (SEQ ID NOS:20 and 49) promotes fibrous capsule formation after implantation without the development of inflammation. Similarly, in another preferred embodiment subcutaneous injections of poly[0.6 (GGVP), 0.4(GGFP)] (SEQ ID NOS:41 and 42) elicit fibrous capsule formation. Example 1 below illustrates such a polymer with (GGVP)$_3$ GGFP (GGVP)$_3$ GGFP (GGVP)$_3$ GGFP (SEQ ID NO:9).

Polymer characteristics can also be affected by cross-linking. Thus, the polymers used in the present invention can be cross-linked prior to, during, or after injection, if desired, using any of various cross-linking processes, e.g., chemical, enzymatic, or irradiative. Cross-linking provides mechanical strength and rigidity to the polymer, and increasing amounts of cross-linking are appropriate for increasing demands of rigidity. Although the most preferred polymers have little or no crosslinking prior to injection, cross-linking to provide one cross-link for every 200–500 repeating units is generally acceptable, with more cross-linking being permitted in less viscous polymers and vice versa. Methods for cross-linking bioelastomeric polypeptides are known in the art. For example, U.S. Pat. No. 4,589,882, incorporated herein by reference, teaches enzymatic cross-linking by synthesizing block polymers having enzymatically cross-linkable units. Additionally, cross-linking by irradiation is described in detail in nearly all of the prior patents arising from the laboratories of the present inventor.

In situ cross-linking can also be used after injection to maintain the polymer at the site of injection (Kagan, et al., *J. Biol. Chem.* 255:3656–3659 (1980)). In this aspect of the invention, cross-linking occurs at the site in need of augmentation and cross-linking of the polymer can occur intermolecularly and/or to the surrounding tissues, anchoring the composition in place. For example, cysteine can be introduced into the polymer to allow for linkage via disulfide bridges to a surface, or lysine can be introduced for enzymatic linkage to a surface, using a natural extracellular enzyme that cross-links for example, collagens and elastins. Example 2, below, illustrates such a polymer, $(GVGVP)_2$ GKGVP GVGVP GVGFP GFGFP (SEQ ID NO:10), which contains a Lys(K) residue in a sequence that is a demonstrated substrate for the cross-linking enzyme lysyl oxidase.

Another approach for maintaining the polymer at the injection site involves the inclusion of cell attachment sequences (Nicol, et al., *J. Biomed. Mat. Res.* 26:393–413 (1992)).

The bioelastic polymers can also optionally have insertions of, for example, single amino acids between monomeric units, substitutions of one amino acid for another in an occasional monomer, or inclusion of different polypentapeptide, polyhexapeptide or polytetrapeptide sequences which can be added either in parallel or in sequence to increase strength in elastic modulus or provide some other desired characteristic. See U.S. Pat. Nos. 4,474,851 and 5,064,430. The resulting polymers are thus properly known as copolymers, as they are formed from different monomeric units.

Considerable variations in the amino acids that are present at various locations in the resulting polymer is also possible as long as the multiple β-turns with intervening suspended bridging segments are retained in order to preserve elasticity. For this reason, it is preferred that at least 50% of the polypeptide is formed from the repeating monomeric units, more preferably at least 70%, even more preferably at least 90%. Nevertheless, it is possible to prepare polypeptides in which these monomeric units are interspersed throughout a larger polypeptide that contains peptide segments designed for other purposes. For example, the bioelastomer can contain naturally occurring sequences which are components of connective tissue or impart functions such as biological activity, chemotaxis, cell targeting and/or adhesion, drug attachment, or protease or nuclease susceptibility. The sequences can be added covalently and sequentially or as side chains to provide for the desired function. The ratio of these other sequences to the monomer residue can range from 1:2 to 1:5000. Preferably the ratio is 1:10 to 1:100. The upper limit on the number and kind of substituents is also influenced by the ability of the elastic polymer to fold/assemble properly to attain a beta-spiral in the relaxed state.

For instance, Example 3 illustrates a protein-based polymer containing a cell attachment sequence, Arg-Gly-Asp, from fibronectin to result in the elastic matrix $(GVGVP)_{10}$ GVGVPGRGDSP $(GVGVP)_{10}$ (SEQ ID NO:13). Further examples of matrices that promote cell adhesion, cell spreading and growth are $X^{20}$-poly[40(GGAP),(GRGDSP)] (SEQ ID NO:21) and poly[20(GVGVP),(GRGDSP)] (SEQ ID NO:53) (Nicol, et al., "Cell Adhesive Properties of Bioelastic Materials Containing Cell Attachment Sequences," In Biotechnol. Bioactive Polym, (Charles G. Gebelein and Charles E. Carraher, Jr., Eds.), Plenum Press, New York, pp. 95–113 (1994)). Such polymers allow cells (e.g., fibroblasts) to migrate into and attach to the matrix and to sense the tensional forces to which the matrix is subjected in its functional role, thus allowing the natural cells to regenerate the tissue to sustain the forces required for the tissue to function appropriately. Thus, numerous methods exist, which can be used in combination, to maintain the polymer at the site in need of augmentation and resulting in long term augmentation.

In order to obtain high molecular weight polymers in good yields, a number of approaches are available. Synthesis of the bioelastic repeating units is straightforward and easily accomplished by a peptide chemist or by standard methods in microbial fermentation. For example, organic synthesis of the polymers has been described in the patents listed in the Background Section. In particular, the synthesis and cross-linking of poly(GVGVP) have been described in U.S. Pat. No. 4,783,523. The synthesis of poly(IPGG) has been described in U.S. Pat. No. 5,250,516 and that of poly (GGAP) in U.S. Pat. No. 5,527,610. Accordingly, the teachings of these patents can be applied to the synthesis of bioelastic polymers having different monomer units. When producing polymers by chemical synthesis, care should be taken to avoid impurities, because small levels of impurities can result in termination of the polymerization process or in racemerization that can alter the physical properties of the resulting polymer, but there are otherwise no particular problems of synthesis. Peptide unit purity is important in obtaining a material with suitable physical properties, since small changes in the preparation of the pentamers can result in a transition temperature that varies as much as 15° C. This variance is important to consider since a polymer that has a 25° C. transition temperature will be injectable at 37° C., whereas a preparation having a 40° C. transition temperature may not have the desired properties for tissue augmentation. The solution of this potential problem is simply to purify the components used to prepare the peptide.

Pure or substantially pure bioelastomers of the invention have been found to be biologically inert. However, it has been found that even a less than pure bioelastomer will find utility in the methods of the invention. For example, less then pure $(GVGVP)_{251}$ (SEQ ID NO:18) was found to induce a tissue reaction sufficient to form a fibrous capsule, thus maintaining the volume, i.e., insignificant volume change after injection, as is required for the tissue augmentation method of the invention.

The polymer can be prepared as a homopolymer or a copolymer. Either random or block copolymers prepared from at least two of the monomeric units are useful in the methods of the present invention but are less preferred when an equivalent homopolymer has the desired physical properties, simply because of the greater complexity of synthesis. Irrespective of how the bioelastic polymers are synthesized, these can further be derivatized, if desired. For example, photoresponsive or electroresponsive side chains can be incorporated into the polymer as described in U.S. patent application Ser. Nos. 08/187,441 and 08/487,594.

The protein-based polymers can also be prepared using genetic engineering techniques. Using this approach, a gene encoding the desired peptide sequence is constructed, artificially inserted into, and then translated in a host organism. The organism can be prokaryotic, e.g., bacterial, or eukaryotic, e.g., yeast or plants. Techniques are known in the art of molecular biology to manipulate genetic information (i.e., DNA sequences) for effective gene expression in an appropriate host organism (see, for example, Sambrook et al., Molecular Cloning: A Laboratory Manual, Second Edition, Cold Spring Harbor, N.Y. (1989)) and include the use of enzymes capable of cleaving, joining, copying or otherwise modifying polynucleotides. In addition, vectors allowing the introduction of this information into the host organism in a suitable manner for expression are known in the art. A detailed example of the production of poly-VPGVG is set out in McPherson, et al., Biotechnol. Prog. 8:347–352 (1992), a publication arising from the laboratory of the present inventor. This publication can be used as guidance for genetic-based production of any of the materials used in the present invention. Polymers with as many as 2000 amino acid residues have been expressed in good quantity by appropriate E. coli strains. For example, expression of $(GVGVP)_{121}$ (SEQ ID NO:40) has occurred at levels of 80% of E. coli cell volume. Thus, the cost of production of these protein-based polymers can be competitive with synthetic, organic polymers and with natural materials that need extensive purification. Producers of industrial proteins have demonstrated that costs can be reduced significantly for biologically produced proteins. Of course, medical applications requiring high purity can accept higher costs for medically important applications. For example, costs for the collagen-containing product Contigen®, intended to alleviate urinary incontinence, are understood to be in the range of $1000 (U.S.) per gram.

The bioelastic polypeptide can be purified, for example, from cultures grown in fermentation reactors or from organic syntheses, by its ability to undergo an inverse temperature transition. Purification using the inverse temperature transitional properties of the protein-based polymers is preferred with genetically engineered polymers expressed in microbial systems as endotoxin levels have been demonstrated to be particularly reduced using this method.

The bioelastic polypeptide compositions are biocompatible as a tissue implant and are readily sterilizable. "Biological compatible" as used herein, relates to materials that in final form will not harm the organism or cell into which it is implanted to such a degree that implantation is as harmful or more harmful than the defect being corrected. Biocompatibility can be ascertained by numerous methods known to one of ordinary skill in the art (Picciolo, et al., "A Biotechnology-derived Biomaterials Modulate Host Cell Reactive Oxygen Production as Measured by Chemiluminescence" 19th Annual Meeting, Society for Biomaterials, Birmingham, Ala. (1 993); Urry, et al., Mat. Res. Soc. Symp. Proc. 292:253–264 (1993); and Hoban, et al., J. Surgical Res. 56:179–183 (1984)). For example, it can be determined whether the bioelastic material is capable of eliciting an immune response. Preferably, the bioelastic compositions are non-immunogenic. "Non-immunogenic" as used herein relates to materials which provoke no substantial immune response, inflammation or foreign body reaction when administered. The material can also be tested for biocompatibility by implanting the material in an intended host or substitute test animal and observing the implant at numerous time points after implantation for any adverse reactions.

The bioelastic polypeptide compositions can be selected to be biodegradable. "Biodegradable" as used herein relates to the potential for a material to be degraded by the action of enzymes (including, for example, proteases), or other biological processes, to yield non-toxic substances or byproducts which are compatible with normal body processes. The degree to which a material is biodegradable can vary depending on the particular indication. The propensity of such biopolymers to act innocuously in the body allows these polymers to be injected at sites in need of tissue augmentation where they can reside in the body for days, weeks or longer. Polymer stability can be controlled by appropriate design of the polymer, as it is apparent to one of ordinary skill in the art. For example, protease cleavage sites can be included in the polymer's primary sequence to increase the polymer's susceptibility to protease, or "chemical clocks" as described in European Patent No. 0449592 or its corresponding U.S. application.

Injectable compositions of the invention are useful in plastic surgery, for example, for tissue reconstruction or dermal augmentation (for example, for filling in dermal creases and providing support for skin surfaces), sphincter augmentation (for example, for restoration of urinary continence), delivery of cells, tumor blood vessel blockage, tumor therapy, and contraception/infertility treatments. For example, the problem of stress urinary incontinence can be overcome by adding a periurethral bulking capacity at the base of the bladder. Simply by replacing a Glu (E) residue of a $(GVGVP_4, GEGVP_1)$ (SEQ ID NO:22) polymer by an occasional ArgGlyGlu sequence (from the GRGDSP cell attachment sequence (SEQ ID NO:46)), subcutaneous injection of polymer causes generation or restoration of a natural tissue with the normal distribution of elastic and collagen fibers, rather than simply disappearing. Using the same polymer composition, but cross-linking it to form a matrix with an elastic modulus matching that of the natural bladder and placing on it a human urethral explant containing uroepithelial cells, the cells grow out onto the matrix, but the growth is stimulated toward a greater density of cells and extraceliular matrix by simulating the tensional force changes of bladder filling and emptying.

A particularly useful technique is the replacement of degraded or injured nucleus pulposus in intervertebral discs. The bioelastic polymers described herein can be used in the restoration of diseased intervertebral discs by means of arthroscopic implantation of pressure-responsive and cell stimulation bioelastic materials directly into the depleted nucleus pulposus. In this approach, the prosthesis should match the mechanical properties of the tissue being restored, and, in preferred embodiments, it should contain cell attachment sites to which the normal cells of the tissue attach.

In this embodiment of the invention, the method for tissue restoration of intervertebral discs in a mammal, comprises the step of injecting a polymer into the depleted nucleus pulposus site, which has a site temperature, said polymer comprising repeating peptide monomeric units selected from the group consisting of nonapeptide, pentapeptide and tetrapeptide monomeric units, wherein said monomeric units form a series of β-turns separated by dynamic bridging segments suspended between said β-turns, wherein said polymer has an inverse temperature transition $T_t$ less than said site temperature, and wherein said polymer is injected as a water solution at coacervate concentration in the substantial absence of additional water and swells to increase the pressure within the disc.

Typically, during an endoscopic discectomy or other percutaneous procedure, the degraded or injured nucleus pulposus is removed from the intervertebral discs by commercially available endoscopic discectomy equipment. First, a trocar is used to make a hole in the annulus. The endoscopic discectomy equipment is then inserted through the hole and the nucleus pulposus removed. Injection of the bioelastomers of the invention can be injected into the site through the pre-formed hole, either by a large syringe or by modification of the discectomy equipment to provide for loading and delivery of the bioelastomer into the space vacated by the nucleus pulposus.

In another embodiment of the invention, the method for tissue restoration of intervertebral discs in a mammal, comprises the step of injecting a polymer into the depleted nucleus pulposus site, which has a site temperature ($T_s$), said polymer comprising repeating peptide monomeric units selected from the group consisting of pentapeptide and tetrapeptide monomeric units, alone or in combination, wherein the monomeric units form a series of β-turns separated by dynamic bridging segments suspended between the β-turns, and wherein (i) the polymer has an inverse temperature transition $T_t$ less than $T_s$, (ii) the polymer is injected as a water solution at coacervate concentration in the substantial absence of additional water and swells to increase the pressure within the disc, and (iii) the coacervate has an elastic modulus at $T_s$ within the range of $5 \times 10^4$ to $5 \times 10^6$ N/m$^2$.

First, the selected bioelastic materials (which are pressure responsive, viscoelastic protein-based polymers) are designed to restore proper dimensions by arthroscopic emplacement in the depleted nucleus pulposus in a state that results in the correct swelling pressure, i.e., they are designed so as to be capable of effecting turgor pressure development on implantation for the purpose of mechanical restoration of the compressed disc to its correct dimensions and internal pressure. Second, biologically active sequences can optionally (and preferably) be included in the sequence to induce tissue regeneration or restoration while the disc is in an improved structural/functional state, i.e., they are designed so as to be capable of stimulating tissue restoration of the intervertebral disc to its more natural state. By multiple attachments of cell to the mechanically correct matrix, which acts as a temporary functional scaffolding, the mechanical stresses sustained by the functional artificial matrix would be appropriately transmitted to the cells. Since it is believed that cells are mechano-chemical transducers that respond to the force changes that they sense, this mechanical sensing by the cells would result in the chemical remodeling of the matrix into a natural tissue sufficient to sustain those forces (that is, in the elaboration of the required extracellular matrix). Polymers of particular interest for this application include, by way of illustration and not limitation, $(GVGIP)_n$ (SEQ ID NO:51) and $[(GVGIP)_{10}]_n$ (SEQ ID NO:56), along with $[(GVGVP)_2 \text{ GKGVP GVGFP GFGFP}]_n$ (SEQ ID NO:54), $[(GVGIP)_{10} \text{ GVGVPGRGDSP} (GVGIP)_{10}]_n$ (SEQ ID NO:57), $[(GVGIP)_{10} \text{ GVGVPGRGDSP}(GVGVP)_{10}]_n$ (SEQ ID NO:58), $[\{(GVGVP)_2 \text{ GFGVP}\}_3]_n$ (SEQ ID NO:59) and $[(GVGIP)_{10} \text{ GVGVPGRGDSP (GVGVP GVGVP KGVP GVGFP GFGFP})_2]_n$ (SEQ ID NO:60).

As noted earlier, the value of $T_t$ depends upon numerous factors and, accordingly, the value of $T_t$ can be shifted to carry out a wide variety of energy conversions, including the energy required to maintain an internal pressure for an intervertebral disc.

As relates to tensional force changes, this mechanochemical transductional property of cells has been referred to as "cellular tensegrity". (Ingber, *Int. Rev. Cytol.* 150:173–224 (1994) and Ingber, *J. Cell Sci.* 104:613–627 (1993)). It is a more general concept, however, that includes both compressional and tensional forces. Recent studies have shown that the cells of the intervertebral disc are mechano-chemical transducers and the proper mechanical energy input in terms of applied pressures and the time course of fluctuation in pressure dictate chemical output of the cells of the intervertebral disc (Ishihara, et al., *J. Appl. Physiol.* 80(3):839–846 (1996)).

Another key aspect is the ability of diseased discs to maintain hydrostatic pressures developed on emplacement of the hygroscopic viscoelastic protein based polymers. Studies on autopsy specimens indicate that the nucleus pulposus behaves hydrostatically as long as the disc has not undergone extensive degeneration. (Nachemson, et al., *J. Bone Jt. Surg. Am.* 46A:1077–1092 (1964) and Nachemson, *Acta Orthop. Scandinavica*, Suppl. 43:1–104 (1960)). The outer tendinous bands of the annulus fibrosis come under increased tension on increasing hydrostatic pressure whereas those of the inner annulus come under compression. Further, examination of the compressive stress has shown that intervertebral discs behave as fluid filled pressure vessels (Nachemson, et al., *J. Bone Jt. Surg. Am.* 46A:1077–1092 (1964)). These two observations factor into the approach taken to design protein-based polymers for intervertebral disc restoration.

There are two pressure sensitive aspects of the viscoelastic proteins based polymers described herein that are important in the design and/or selection of polymers useful for the restoration of intervertebral discs. One is demonstrated by $(GVGIP)_{260}$ (SEQ ID NO:55) and the other by the introduction of pressure sensitivity by $T_t$ by the presence of aromatic residues. This is explained in greater detail in the examples.

Additional biologically important factors may be added for repair of hard tissue (for example, mineral additives for correction of bone defects or osteogenic factors including bone morphogenic proteins to promote mineralization or bone formation) or to enhance cell growth in the vicinity of the injection (for example, cell-growth or cell-attraction agents, host-compatible cells or growth factors). The appropriate amount of material to be added to the composition to achieve the desired effect will be apparent to the medical practitioner and is not a requirement of the present invention, as such selection is usually made by the physician (aided, if necessary, by analytical analysis of biopsied tissue) to achieve the result desired by the physician and/or required by the injury or defect. Such factors are supplemental to the invention itself and are optional, not being required or desirable in many cases.

The bioelastic material to be injected can be dissolved or suspended in a pharmaceutically acceptable liquid carrier prior to injection. Examples of an appropriate liquid include physiologically buffered salt solutions, water, glycerol and the like, and may be supplemented with, for example, serum, growth factors, hormones, sugars, amino acids, vitamins, metalloproteins, lipoproteins, and the like. Most of the carrier will be removed prior to injection, as discussed above, but some may remain in the final injectable composition. Thus, compositions used in the invention may additionally include one or more biologically active factors to aid in the healing or regrowth of natural tissue. For example, one may incorporate factors such as heparin, epidermal growth factor (EGF), transforming growth factor alpha (TGF-α), TGF-β, platelet-derived growth factor, fibroblast growth factor, connective tissue activating peptides, β-thromboglobulin, insulin-like growth factors, tumor necrosis factors, interleukins, colony stimulating factors, erythropoietin, nerve growth factors, interferons, osteogenic factors including bone morphogenic proteins, and the like. Incorporation of such factors, and appropriate combinations of factors, can facilitate the tissue treatment. Decisions to use such factors are typically made by the attending physician based on judgments about the injury or defect being repaired.

Similarly, one can inject a mixture comprising cells and the bioelastic polymer at the site in need of augmentation. The cells are living cells, preferably from the host receiving the injection or from a cell source sufficiently related to avoid graft/host interactions leading to rejection, including human cells. Cells can be autogeneic, isogeneic, allogeneic or xenogeneic, more preferably autogeneic or allogeneic. Included are cells which have been genetically engineered. The bioelastic compositions can contain different cell types, which may be chosen to act synergistically, for example, in the formation of tissue. Examples of types of cells include muscle cells, nerve cells, epithelial cells, connective tissue cells, and organ cells. Specific examples of cells include fibroblast cells, smooth muscle cells, striated muscle cells, heart muscle cells, nerve cells, epithelial cells, endothelial cells, bone cells, bone progenitor cells, bone marrow cells, blood cells, brain cells, kidney cells, liver cells, lung cells, pancreatic cells, spleen cells, breast cells, foreskin cells, ovary cells, testes cells and prostate cells. Other mammalian cells are useful in the practice of the invention and are not excluded from consideration here. Alternatively, the injectable bioelastic compositions can include non-mammalian eukaryotic cells, prokaryotic cells or viruses.

The present invention also provides kits for performing the method of the invention. Such kits can be prepared from readily available materials and reagents and can come in a variety of embodiments. For example, such kits can comprise, in an amount sufficient for at least one treatment, any one or more of the following materials: bioelastic polymer, vessels, sterilized buffers (e.g., phosphate buffered saline) or water, other reagents necessary or helpful to perform the method, and instructions. Typically, instructions include a tangible expression describing reagent concentration or at least one method parameter, such as the amount of reagent to be used, maintenance time periods for reagents, and the like, to allow the user to carry out the methods described above. In a preferred embodiment of the invention, a kit comprises a means for delivery in which is placed the bioelastic polymer, both of which are often pre-sterilized. Such means can include, by way of illustration and not limitation, a small syringe (22 to 27-gauge), a large syringe (13 to 19-gauge) and equipment used in endoscopic or percutaneous discectomy procedures. The reagents can be provided in solution, as suspensions, or as a substantially dry powder, e.g., in lyophilized form, either independently or in a mixture of components to improve ease of use. Where a degradable reagent is provided, conditions are chosen so as to stabilize the reagent, e.g., storage at lower temperature, addition of stabilizing agents (e.g., glycerol or a reducing agent). Unstable reagents can be provided together with or separately from the more stable components of the kit.

A particularly preferred embodiment of a kit is a kit for augmentation of a tissue, the tissue having a normal tissue temperature, comprising a syringe (either small or large), a sterile wrapper surrounding the syringe and providing a sterile environment for the syringe, and a polymer contained in the syringe, wherein the polymer comprises repeating peptide monomeric units selected from the group consisting of nonapeptide, pentapeptide and tetrapeptide monomeric units, wherein the monomeric units form a series of β-turns separated by dynamic bridging segments suspended between the β-turns, and wherein the polymer has an inverse temperature transition $T_t$ less than the tissue temperature. The polymer can be present in the syringe either in solution or as a water solution at coacervate concentration in the substantial absence of additional water. Where the polymer is present in solution, the syringe and the polymer it contains are maintained at low temperatures to stabilize the polymer, since the polymer is usually in solution rather than in the form of a coacervate at low temperatures (depending, as discussed above, on the value of $T_t$). In such cases the coacervate is formed by raising the temperature of the syringe and polymer to above $T_t$, after which the excess water (now in a separate phase from the coacervate) can be expelled from the syringe prior to injection of the coacervate. An example of such use is described below.

The following examples describe specific aspects of the invention to illustrate the invention and provide a description of the present method for those of skill in the art. The examples should not be construed as limiting the invention, as the examples merely provide specific methodology useful in understanding and practice of the invention.

EXAMPLES

The preparation of the elastic protein-based polymers utilizes gene construction, development of an expression system, fermentation and purification as described for the particular examples given below. As for gene construction, the basic monomer genes were designed to have appropriate cohesive ends comprising an appropriate restriction site sequence (selected using standard techniques, such as consideration of the restriction sites present in the vector to be used for expression). Polymerization of the basic gene was carried out through the compatible sticky ends generated by restriction endonuclease digestion, followed by subsequent ligation using DNA ligase to form multimers of the basic gene. This protocol was used successfully to produce each of the monomer gene sequences. The monomers were then concatamerized (polymerized) to form multimer genes with many different numbers of repeats, and many of the multimer genes have been expressed at high levels as will be briefly reported below.

Example 1

Phenylalanine-Containing Tetrameric Bioelastic Materials

This example illustrates a phenylalanine-containing bioelastic material that can elicit fibrous capsule formation without a significant inflammatory response. Generally, the protocols used for this particular construct is applicable to other protein elastomers described herein. Standard amino acid abbreviations are used here and elsewhere in this specification (phenylalanine is abbreviated Phe or F).

Fibrous capsule formation prevents polymer migration, thus providing long term tissue augmentation. The polymer of this Example 1 is $(GGVP)_3$ GGFP $(GGVP)_3$ GGFP $(GGVP)_3$ GGFP (SEQ ID NO:9), where n is generally from 1 to 60, usually 10 to 50 and preferably from 20 to 40. The polymer has a $T_t$ of about 20° C., thus ensuring coacervate formation at 37° C. The polymer is stable and extrusible at 37° C.

a. Gene Construction

The basic monomer gene for $(GGVP)_3$ GGFP $(GGVP)_3$ GGFP $(GGVP)_3$ GGFP (SEQ ID NO:9) is constructed using the following oligonucleotides:

5'-GAGGATCCGAAGACAACAGGTGGTGTTC-
CGGGCGGCGTACCGG GTGGCGTACCGGGCGGTTC-
CCGGGAGGTGTGCCGGGTGGGGTTC CAGGCGGTGTAC-
3' (SEQ ID NO:23)

and

5'-CTGGATCCGAAGACTTCCTGGAAAAC-
CGCCCGGCACGCCACCCG GAACTCCACCCGGAACAC-
CGCCCGGAAACCCACCCGGTACACCGC CTGGAAC-
CCCA-3' (SEQ ID NO:24)

The oligos are annealed through the 20-base-pair complementary regions at their 3' ends and extended with a thermostable DNA polymerase and free deoxy-nucleotides to give the double-stranded monomer gene illustrated in FIG. 1 (SEQ ID NO:1). This gene is flanked on each end by both of the restriction endonuclease sites BamH1 and Bsp1. The basic monomer gene is cloned into pUC 118 via the BamH1 restriction site. After cloning and characterization of the monomer gene, it can be digested out of pUC 118 with Bsp1 and purified in adequate amounts for polymerization. Polymerization is achieved by ligation using DNA ligase to join the gene fragments in a head-to-tail fashion through the non-palindromic Bsp1 ends and in the presence of cloning adaptors, thus forming multimers of the basic gene (similar to the description in FIG. 3).

The gene sequences chosen allow concatamerization of the basic gene sequence such that the gene segments remain in proper reading frame. Ligation conditions are that typically understood by one of ordinary skill in the art of gene cloning. The sequence of the basic concatamer gene is verified using routine procedures, such as with SequenaseT™ from Amersham Life Science, Inc. Genes encoding bioelastic polymers as large as 2000 residues have been expressed using this technique.

b. Gene Expression

Similar to described for FIG. 3, the concatamer gene can be expressed using pET plasmids (Novagen, Inc., Madison, Wis.), such as pET-lld. These plasmids are part of the $T_7$ expression system that utilizes the $T_7$ phage RNA polymerase in conjunction with a $T_7$ promoter to drive recombinant gene expression (Studier, et al., *Meth. Enzymol.* 185:60–89 (1990)). The gene fragment is released from the plasmid, pUC118, by cleavage with Nco1 and BamH1 and purified. The fragment is then cloned into the pET plasmid at the Nco1 and BamH1 sites placing the initiator ATG codon of the concatamer gene adjacent to the $T_7$ promoter and ribosome binding sequences.

*Escherichia coli* is transformed with the plasmid by methods known in the art and the cells cultured. Expression of the concatamer genes is analyzed by growing a bench-scale culture of the transformed *E. coli*. Expression can be induced with or without isopropylthio-β-galactosidase. Crude cell lysates of the cultures, taken pre- and post-induction, are analyzed by sodium dodecylsulfate-polyacrylamide gel electrophoresis (SDS-PAGE) and the products visualized by $CuCl_2$ staining of the gels.

c. Fermentation

The protein-based polymers are produced by growing host cells transformed with the polymer-expressing PET-lld derivative in either Luria broth (LB) or Terrific Broth (TB) media. The production of the protein-based polymers may be induced with the addition of the inducing agent IPTG. After an appropriate number of hours of growth, the culture is harvested by centrifugation and cells are disrupted by means of a French press to release the cell contents. (Daniell et al., Methods in Molecular Biology Series Entitled Expression and Detection of Recombinant Genes (1995)). The phenylalanine-containing polypeptide (or other such elastomer as the case may be) is then characterized for use as an injectable implant.

d. Purification

The protein-based polymers can be conveniently purified from culture lysates using their inverse temperature transitional properties. (Urry, et al., Handbook of Biomaterials and Applications, Marcel Dekker, Inc., New York, pp.2645–2699 (1995); Urry, *Angew. Chem.* (German) 105:859–883 (1993); *Angew. Chem. Int. Ed. Engl.* 32:819–841 (1993); and McPherson, et al., Protein Expression and Purification (1995)). The cell lysate is cooled to 4° C. and centrifuged at high speed to remove insoluble material. The protein-based polymers form large aggregates and undergo phase separation (coacervation) when the supernatant fraction is either warmed to 37° C., or exposed to a high concentration of salt (NaCl) or subjected to a pH change, depending upon their composition. The protein-based polymer is then removed by centrifugation and solubilized under the appropriate conditions, (e.g., cooling or lowering salt concentration). Repeating this process several times results in a protein-based polymer with essentially all other proteins removed. After centrifugation, the sample is dialyzed to remove any residual salts and then lyophilized to determine initial yield. At this stage, a temperature profile for aggregation can be obtained as described below.

The solution is then to lower the temperature below its $T_t$ so as to resolubilize the coacervate followed by passing under pressure through a 0.2 micron membrane as a prefiltration step and then through a sterile bench-top Amicon ProFlux M12 tangential flow ultrafiltration apparatus employing a 100 kDa spiral wound cartridge. The solution is then lyophilized, and the protein-based polymer is tested at a concentration of 1 mg/ml for endotoxin levels using the Associates of Cape Cod, Inc. Pyrotell Limulus Amebocyte Lysate (LAL) test. The endotoxin levels are found at this stage to be within the recommended guidelines, e.g., Guideline on Validation of the Limulus Amebocyte Lysate as an End Product Endotoxin Test for Human and Animal Parenteral Drugs, Biological Products, and Medical Devices prepared by the Centers for Drug Evaluation & Research, Biological Evaluation & Research, Devices & Radiological Health and Veterinary Medicine d. Characterization of the Bioelastic Polymer i. Determination of $T_t$ and the Concentration to Obtain No Change in Volume Under Physiological Conditions To determine $T_t$, the polymer is dissolved at 40 mg/ml at 4° C.; the cold solution is placed in a spectrophotometer, and the temperature is raised to observe the onset and development of turbidity. The temperature at which 50% turbidity is obtained is defined as $T_t$.

To obtain the concentration at which there will be no volume change on injection into a mammal, approximately 1200 mg of the test sample is weighed into 5 ml syringes (B/D[R]) and dissolved in phosphate buffered saline at 4° C. to a volume of 1 ml for each 400 mg of bioelastic polymer. Once dissolved, the sample is equilibrated at 37° C. to form the coacervate phase and the excess water extruded. Once the water has been removed, no significant volume change occurs on injection. The sealed syringe containing coacervate can be gamma-irradiated at 2.5 Mrads for sterilization.

ii. Determination of Extrusibility

The sample prepared in (a) immediately above is tested for extrusibility in vitro by extruding through a 22-gauge or a 27-gauge surgical needle after equilibration at 37° C.

iii. In vivo Studies

After determining extrusibility, the bioelastic polymer is injected subcutaneously into rats. At intervals of three and five weeks after injection, the animals are sacrificed and examined (i) macroscopically to determine the approximate volume of the retained material, and (ii) histologically to characterize the extent of fibrous capsule formation, to determine the occurrence of any cellular migration into the injected material, and to assess the presence of any inflammatory response or adverse tissue reaction.

Typically, 5 rats are dosed with test or control, by subcutaneous injection with 0.2 ml sample coacervate by means of a fine (22-gauge) hypodermic needle. One group of animals are tested for three weeks and another group for five weeks. At the end of three weeks or five weeks, the animals are sacrificed and the tissue examined. The test material is located, extent of material retention recorded, as well as any volume changes of the material. The tissue with implant in place is fixed in 10% neutral buffered formalin. The tissue sample for each test and control for each animal is embedded, cut and stained with hematoxylin and eosin. Stained slides are evaluated to observe the formation of a fibrous capsule and any other tissue response. Microscopic evaluation of each implant assesses the occurrence of any cellular migration into the material. Animal results are discussed below.

Example 2

Bioelastic Material Effective in In Situ Cross-Linking

In addition to Phe (F) residues that can elicit fibrous capsule formation, the polymer illustrated in this Example also contains a Lysine (Lys, K) residue repeating every 30 residues. The natural extracellular enzyme, lysyl oxidase, very effectively oxidizes lysine in this sequence to an aldehyde, thus allowing in situ cross-linking (Kagan, et al., supra). The resulting allysine, α-aminoadipic γ-semialdehyde, residue spontaneously forms a Schiff base cross-link under physiological conditions with any other proximal lysine residue in the polymer or in the surrounding tissue (e.g., to collagens and elastins of the extracellular matrix) or spontaneously forms an aldol condensation product with a second allysine or other aldehyde, such as glutaraldehyde, for cross-linking. The polymer has the sequence $[(GVGVP)_2\ GKGVP\ GVGVP\ GVGFP\ GFGFP)]_n$ GVGVP where n is 21 (SEQ ID NO:25).

The expression and testing of the base polymer sequence $(GVGVP)_2$ GKGVP GVGVP GVGFP GFGFP) (SEQ ID NO:10) can be achieved essentially as described in Example 1 but using the following oligonucleotides to construct the monomer gene:

5'-GAGGATCCAGGCGTTGGGGTACCGGGT-
GTTGGCGATCCGGGTAA AGGTGTCCCGGGGTTGGT-
GTGC-3' (SEQ ID NO:26)

and

5'-CTGGATCCAACGCCTGGGAATCCGAAAC-
CCGGAAAGCCTACACC CGGCACACC AACGCCCGG-
GACA-3' (SEQ ID NO:27)

The differential phase separation during the purification process can be achieved by varying the pH of the solution containing the Lys(K) polymer described here.

In addition to the characterization described in Example 1, in situ crosslinking is assessed for this polymer. The polymer is recovered from the injection site of the animals and compared to recovered control polymers (such as that described in Example 1). The polymers are assayed for cross-linking by hydrolysis and chromatography as described by Kagan, et al., supra. The observation of chromatography peaks for a-amino-adipic-γ-semialdehyde and the aldol condensation product indicates cross-linking of the polymer.

Example 3

Bioelastic Material Containing Cell Attachment Sites

This Example illustrates a polypentapeptide with a $T_t$ of approximately 26° C. which is designed with a recurring fibronectin cell attachment site, GRGDSP (SEQ ID NO:28), to which fibroblasts and other cells can attach, spread and grow to confluence (Nicol et al., supra (1992); Nicol, et al., supra (1994); and Urry et al., Biotechnological Polymers: Medical, Pharmaceutical and Industrial Applications, 82–103 (1993)). The sequence encourages stabilization of the implant by cell invasion and is useful in preparing bioelastic polymers for generation of the natural tissue with the appropriate distribution of elastic and collagen fibers. The polymer has the sequence $(GVGVP)_{10}$ GVGVP GRGDSP $(GVGVP)_{10}$ (SEQ ID NO:13).

Construction of the basic monomer gene for this gene, $(GVGVP)_{10}$ GVGVP GRGDSP $(GVGVP)_{10}$ (SEQ ID NO:13), FIG. 5, was carried out by the following protocol. The basic gene for $(GVGVP)_{10}$ (SEQ ID NO:29) was constructed such that a sequence containing the cell attachment site, GRGDSP, could be flanked on both sides by the basic $(GVGVP)_{10}$ gene. This was done as follows: The plasmid consisting of pUC118 containing the basic gene of $(GVGVP)_{10}$ was cleaved with restriction endonuclease PflM1 to release the gene fragments for purification. In addition, the resulting pUC 118 plasmid with PflM1 ends was purified and used as the cloning vector for the subsequent gene constructs. For each polymer, a ligation reaction was performed including the PflM1 gene fragment and a synthetic double-stranded oligonucleotide encoding the GRGDSP cell attachment sequence. As illustrated with the sequence information presented in FIG. 3, the GRGDSP oligo has 3-base 3' extensions that are complimentary to the PflM1 ends of the gene fragments; however, upon ligation of these PflM1 ends to complementary ends, the PflM1 site is not restored at this junction. Notice also that the GRGDSP oligo includes a GVGVP coding sequence. The above ligation mix was then digested with PflM1 to resolve the concatenated ligation products to the smallest units spanning the enzyme recognition sites. The digestion mix was then electrophoresed through a polyacrylamide gel where fragments of the appropriate size (333 bp) were purified by excision and electroelution. These PflM1 fragments were then cloned by ligating to the prior generated pUC 118 having PflM1 ends. Clones representing the catemer gene for $(GVGVP)_{10}$ GVGVP GRGDSP $(GVGVP)_{10}$ (SEQ ID NO:13) were isolated and characterized. This catemer gene has PflM1 restriction sites at its termini that allow their subsequent purification and concatanation as described below. DNA sequencing was performed to verify the sequence of the basic catemer genes. This was done, as has become our routine, using standard methodology of the "Sequenase" kit from Amersham Life Science, Inc.

To produce a concatamer of the above GRGDSP containing base monomer gene, the required large amount of the base gene fragment was prepared by releasing the gene from plasmid pUC118 by cleavage with PflM1, separation by electrophoresis through a polyacrylamide gel, followed by electroelution from the gel. The gene fragments were then concatanated by ligation through the PflM1 ends in the presence of double-stranded oligonucleotide adapters whose purpose was to terminate further polymer growth from the ends that they adjoin and provide the terminal restriction endonuclease sites required for cloning the gene polymers, as shown in FIG. 8.

In this case, the concatanation ligation product was digested with BamH1, mixed with BamH1-cleaved pUC118 and ligase, and was inserted into *E. coli* by transformation. Concatamer clones were analyzed by restriction endonuclease digestion and electrophoresis versus known size standards, including a concatamer ligation ladder where it was possible to count from the basic gene in multiples of this gene right up to the particular isolated concatamer size. Following this protocol, the gene for this polymer was successfully constructed, with an n as large as 18, i.e., [(GVGVP)$_{10}$ GVGVP GRGDSP (GVGVP)$_{10}$]$_{18}$ GVGVP, which is 2003 residues (SEQ ID NO:34). This polymer has been expressed in good levels. The particular polymer of this construction which was used for the injectable implant studies, however, had an n of 7.

a. Mass Spectrometry

As determined by MALDI-TOF (matrix assisted laser desorption ionization-time of flight) mass spectrometry, the molecular weights of the microbially prepared polymers are:

I: [(GVGVP)$_3$ GKGVP (GVGVP)$_2$]$_{36}$ GVGVP, 90,800 Da (SEQ ID NO:35)

II: [(GVGVP)$_2$ GKGVP GVGVP GVGFP GFGFP]$_{21}$ GVGVP, 55,400 Da (SEQ ID NO:36)

III: [(GVGVP)$_{10}$ GVGVPGRGDSP (GVGVP)$_{10}$]$_7$ GVGVP, 64,300 Da (SEQ ID NO:37)

IV: [(GVGVP)$_{10}$ (GVGVAP)$_8$ (GVGVP)$_{10}$]$_5$ GVGVP, 60,300 Da (SEQ ID NO:38)

V: [(GVGVP)$_3$ GEGVP (GVGVP)$_2$]$_{36}$ GVGVP, ~89,000 Da (SEQ ID NO:39)

Representative mass spectra are given for polymers III (64314.3 peak) and IV in FIG. 9 (60347.6 peak).

b. $T_t$ in Physiological Saline

Polymer I, 39° C.; polymer II, 4° C.; polymer III, 29° C.; polymer IV, 28° C., an polymer V, 58° C. at pH 7.3 in phosphate buffered saline and 20° C. at pH 3.

c. Coacervate Concentration and Extrusibility

Coacervate concentrations (the natural concentrations of the polymers under physiological conditions) of all of the polymers, I through V, are of the order of 400 mg/ml. The concentrations that were extrusible through 23 gauge hypodermic needles after the 2.5 Mrad sterilization to prevent bioburden were: I, 322 mg/ml; II, 242 mg/ml; III, 350 mg/ml; IV, 233 mg/ml, and V, 300 mg/ml. The advantage of extrusibility of these high concentrations is that the volume filling result of the injectable implant would exhibit a more limited volume change due to water removal into the tissues in the short term following injection. The collagen injections are commonly at concentrations of less than 50 mg/ml where substantial volume loss due to water uptake occurs.

d. Acid-base Titrations to Determine pKa Values as Relevant

The three polymers with potentially interesting pKa values are polymers I, II and V; these are 9.8, 9.1, and, 4.4, respectively.

e. In Vivo Evaluation of the Prepared Elastic Protein-based Polymers as Injectable Implants The in vivo testing was carried out by NAmSA of Northwood, Ohio. The injectable implant animal model was the guinea pig, strain Crl:(HA)BR from the Charles River Laboratories. The fur was clipped free along the left and right flanks to provide for 3 injection sites on each side of the animal, and six different materials were used with each animal. The control was cottonseed oil and the injection volumes for each test material and control were 100 µL. For both the two week and four week studies, all sites were examined at 4 and 8 hours and every 24 hours thereafter for erythema and edema. In no case for the two week study was edema apparent, and the numerical scale for erythema was 0, no erythema; 1, very slight (barely perceptible); 2, well-defined (pink); 3, moderate to severe (red), and 4, severe (beet redness) to slight eschar formation (injuries in depth). At the two and four week termination times, all sites were examined for histopathology.

f. Injectable for the Comparison of the Test Compositions at 2 Weeks

In all cases there was no edema reported; the rating for erythema never exceeded 1 for any of the test compositions, i.e., a very slight (barely perceptible) erythema and the results were similar for the Control, cottonseed oil. Polymer II which exhibited a detectable impurity at the Western blot level of characterization for the two week sample presented with the most marked acanthosis and dermatitis, yet with no significant neofibrosis, because of this a purer sample of polymer II was selected for characterization after four weeks of implantation.

Reactive fibrosis was not particularly prominent within any of the sites but was present to the greatest degree in polymer III injection sites and further, polymer V injection sites were less inflamed than the Control (cottonseed oil) injection sites. Polymer V was the least reactive most innocuous of the microbially-prepared protein-based polymers.

Representative histological prints (at low and higher power) of four animal test sites were evaluated: the original Control, cottonseed oil; polymer III; polymer IV; and polymer V. All tissue sections at the two week study were stained with hemotoxylin and eosin, and the following descriptions are taken in major part from the NAmSA pathologist's report.

Control

A medium power (x108) photomicrograph was taken of the deep dermis and subcutis of a control (cottonseed oil) injection site. This photomicrograph showed clear spaces, indicative of fat cells. Spaces which were slightly larger in size and had slightly thicker walls represented injection site cysts containing cottonseed oil. A high power (x430) photomicrograph was also taken of the subcutis of the same control site. The newly formed collagenous connective tissue was moderately cellular and characterized by thinner collagen fibers than those seen in mature collagenous connective tissue. A mitotic figure, probably within a fibroblast or histiocyte, was also present.

Polymer III

A low power (x43) photomicrograph was taken of the deep subcutis, deep to the panniculus camosus, which also showed a band of muscle fibers. As the result of injection of polymer III, the subcutaneous fatty tissue was replaced by multifocal to confluent infiltrates of inflammatory cells and spindle-shaped fibroblasts or fibrocytic cells. A high power (x430) photomicrograph of another area of the panniculus from the same injection site was also taken. In this area only a minimal degree of inflammation was present, but moderate numbers of spindle-shaped cells consistent with fibroblasts were evident. At that time only small amounts of collagen had been formed, and this collagen was rather pale in staining character. The photomicrographs also showed numerous small capillaries representing angiogenesis. Remarkably, the only compositional difference between Polymer III and (GVGVP)$_{251}$ (SEQ ID NO:18), is the addition of a peptide sequence toward which fibroblasts are chemotactic and to which fibroblasts attach (GRGDSP(SEQ ID NO:46)). The dramatic difference in the tissue response is consistent with the introduction of such activity.

Polymer IV

A low power (x43) photomicrograph was taken of the dermis and subcutis and showed numerous irregularly-shaped cysts and rather diffuse inflammation within both the subcutis and dermis, yet neutrophils were limited in number. The skeletal muscle layer present deep to the subcutis was also shown. A high power (x430) photomicrograph of the deep subcutis was characterized by inflammatory cell infiltrates and by scattered spindle-shaped cells and fine strands of collagen indicative of a possible early neofibrotic reaction. Again, the tissue appears to be responding selectively to the compositional variation introduced into the elastic protein-based polymer The synthesis of elastin can be the key factor in the generation or reconstruction of stable loose connective tissue rather than scar tissue where there are few if any elastic fibers. As noted by Peacock in *Wound Repair* (1984), "in a scar, where there are few elastic fibers and where collagen fibers become oriented primarily along lines of tension, there is little 'give', and stretching and relaxation are not possible. This accounts for the rigidity of scar tissue and inability to forego repeated deformation and recovery as needed in skin covering a joint or other moving part. Failure to include new elastic fibers in repair tissue until long after collagen fibers are formed is another example of the inferiority of scar tissue to normal tissue and has obvious implications in the repair of skin defects, ligamentous structures and large arteries." In developing a periurethral support volume for the correction of stress urinary incontinence, as in any tissue repair process, the objective should be the regeneration or reconstruction of the natural tissue. Since the half life of elastic fibers in the human body is greater than 70 years, the effective introduction of elastic fibers into the repair process is a guiding premise. Accordingly, when the polymers used for tissue repair have the ability to generate tissue that includes elastic fibers, one can achieve tissue augmentation of longer duration.

Polymer V

Medium power (x108) photomicrographs of the dermis and subcutis of four different sites injected with approximately 30 mg each of the elastic protein based polymer V were taken, each showing the most inflammatory regions of each site. In all of the sites there was no remaining trace of the implant, and normal tissue was observed. In two of the sites no inflammatory cells could be found. In another two sites, the most inflammation that could be found was an extremely limited reaction.

Of the approximately 30 mg injected per site, all of the material with its entire load of endotoxin and trace *E. coli* impurities were released to the tissue and yet there resulted no significant inflammatory response. This represents perhaps the most stringent test of purification, and, therefore, this sample became the target level for purification for each of the elastic protein-based polymers of different compositions which were designed for eliciting selected tissue responses. It is essential to know that the tissue response is due to the particular composition and not due to a different impurity resulting from a modified purification procedure required of the varied composition.

g. Injectable Implants for the Evaluation of Two Test Compositions at 4 Weeks

In addition to the hemotoxylin and eosin stain used for the two week study, for the samples examined at four weeks, the trichrome and Verhoeff-van Gieson stains were used to better assess connective tissue development.

Control

Photomicrographs of several control sites of cottonseed oil injection at four weeks were taken. No lesions are present in the low power (x43) photomicrograph of the full thickness of the skin stained with hematoxylin and rosin. A medium power (x108) photomicrograph of microscopically normal skin stained with a trichrome stain was taken, along with a medium-high power (x216) photomicrograph of dermis showing the normal pattern of slender elastic fibers as demonstrated with the Verhoeff-van Gieson technique. Another medium-high power photomicrograph of the deep dermis and subcutis was taken, showing a paucity of elastic fibers in the region using the Verhoeff-van Gieson stain for elastic fibers. In general, therefore, the sites injected with cottonseed oil had recovered to exhibit essentially normal tissue by four weeks.

Polymer I

Four photomicrographs were taken of sites injected with lysine containing polymer I using two different stains, hematoxylin and eosin, and Verhoeff-van Gieson with the purpose of the latter being to assess elastic fiber or elastic fiber-like activity. A medium power (x108) photomicrograph of the subcutis of a site injected with polymer I showed a marked degree of pyogranulomatous panniculitis, associated with large irregularly-shaped eosinophilic deposits (presumably representing the injected material). The origin of the eosinophilic granules was verified by means of the Verhoeff-van Gieson staining of the additional three sections. A photomicrograph at medium power (x108) of the same area of the subcutis was taken, but stained with the Verhoeff-van Gieson technique. As expected above, the material which was eosinophilic in the H&E-stained sections appeared as black bodies using the Verhoeff-van Gieson stain. A high power (x430) photomicrograph of the same area of the subcutis showed a giant cell which appeared to be digesting/remodeling the black material. Another high power (x430) photomicrograph of the subcutis of a Verhoeff-van Gieson-stained section from the same site indicated that some of the black-staining material was being remodeled into long broad fiber.

Polymer II

Four histological sections of the lysine/phenylalanine-containing polymer II were taken. A medium power (x108) photomicrograph of the deep dermis and subcutis of a site injected with polymer II stained with hematoxylin and eosin showed large eosinophilic deposits present which were surrounded by granulomatous and pyogranulomatous inflammatory cell infiltrates. A medium-high power (x108) photomicrograph of the dermis/subcutis of the same injection site showed the injected material as black when stained with the Verhoeff-van Gieson technique. Most of the deposits were surrounded by giant cells, and there was evidence of remodeling of this material at the perimeter of the deposits, i.e. at the interface between the material and the giant cell cytoplasm. At high power (x430) the same field showed that the black deposits were being remodeled into slender fibers which stained similar to elastic fibers when using the Verhoeff-van Gieson stain. A similar high power micrograph of the subcutis of another site injected with polymer II showed that the Verhoeff-van Gieson stain showed some of the black deposits present within giant cells becoming elongated and convoluted in configuration.

Example 4

Protein-Based Polymers for Intervertebral Disc Restoration

The relevant polymers VI and VII, indicated below can be readily prepared for use with intervertebral discs from human cadavers, and polymers VIII, IX, X and XI can be prepared by means of the recombinant DNA technologies of gene construction, E. coli transformation, expression and fermentation for use in both in vivo animal studies and in more extended studies using cadaver discs.

a. Bioelastic Materials as Pressure Active Viscoelastic Fillers

Polymer VI: $(GVGIP)_{10}$ (SEQ ID NO:56)

Polymer VII: $(GVGVP)_2$ GKGVP GVGFP GFGFP (SEQ ID NO:54)

Transformed E. coli can be used for the synthesis of Polymers VI and VII, such as is described in the Examples above.

i. Compression Under Pressure and Expansion by Swelling to an Equilibrium Pressure Approximately 10 grams of $[(GVGIP)_{10}]_n$ where n=26, i.e., $(GVGIP)_{260}$ (SEQ ID NO:55), with a $T_t$ of about 10° C. can be dissolved in 30 ml at a temperature below 10° C., placed in a refrigerated centrifuge at 2° C., and centrifuged at a mean pressure of 440 MPa while the temperature is ramped over a period of eight hours to 25° C. and held at 25° C. for sixteen hours. At this stage, 10 g of the phase separated coacervate state occupies 6.5 mL. On standing for one and a half hours at atmospheric pressure, the coacervate phase slowly expands to 10 mL. This compression/expansion characteristic of the phase separated state of $(GVGIP)_{260}$ is reproducible and can be varied according to the length of time and the force applied during centrifugation. It should be appreciated that this property is not exhibited by $(GVGVP)_{251}$ (SEQ ID NO:18). Thus, with an appropriate pressure cell, the volume for arthroscopic emplacement of the compressed coacervate state of polymer VI can be chosen to give the desired pressure development after emplacement and standing in the hydrostatically competent space of the nucleus pulposus.

ii. The Pressure Sensitivity Imparted by Phe (F) Residues

The application of pressure raises the value of $T_t$ when phenylalanine (Phe, F) residues are present (Urry, et al., Chem. Phys. Letters 182:101–106 (1991)). This means, for a Phe-containing composition in which the pressure difference can shift the equilibrium from the folded to the unfolded and the hydrophobically hydrated state, that the application of pressure results in a back-pressure that limits the volume change and prevents the channeling of water flow. The channeling of water flow with the periodic application of pressure could lead to disruption of structure. This is perhaps why the major protein of the adductor muscle of bivalves that supports large and variable compressional forces, contains Phe residues as a prominent residue in the dominant repeating sequence. It is for this reason and property that polymer VII (SEQ ID NO:54) is chosen, but it is also chosen for the presence of lysine residues which allows for cross-linking either by glutaraldehyde for the cadaver studies or by lysyl oxidase, the natural cross-linking enzyme, for the in vivo studies. Poly [4(GVGVP), GKGVP] (SEQ ID NO:61) was the first peptide substrate found for lysyl oxidase that was not the natural elastin or collagen substrate (Kagan, et al., J. Biol. Chem. 255:3656–3659 (1980)). Thus, polymer VII (SEQ ID NO:54) above and polymer XI (SEQ ID NO:60) below, are expected to be crosslinked to some degree, in vivo buy the natural extracellular cross-linking enzyme, lysyl oxidase.

b. Bioelastic Materials for Disc Restoration

The polymers have the following sequences:

VIII: $(GVGIP)_{10}$ GVGVPGRGDSP $(GVGIP)_{10}$ (SEQ ID NO:57)

IX: $(GVGIP)_{10}$ GVGVPGRGDSP $(GVGVP)_{10}$ (SEQ ID NO:58)

X: $\{(GVGVP)_2 \text{ GFGVP}\}_3$ (SEQ ID NO:59)

XI: $(GVGIP)_{10}$ GVGVPGRGDSP (GVGVP GVGVP GKGVP GVGFP GFGFP)$_2$ (SEQ ID NO:60)

Polymers VIII, IX and XI contain the cell attachment sequence GRGDSP, and are of the family of compositions that have been shown to stimulate tissue generation when implanted subcutaneously in guinea pigs (Urry, et al., J. Biomaterials Science. Polymer Edition 9(10):1015–1114 (1998)). They are also of the composition, when crosslinked, that provided cell attachment sites through urothelial cells attached and by means of which tensional forces applied to the matrix stimulated cellular proliferation and extracellular matrix formation. The change in going from polymer VIII to polymer IX is to allow working with a polymer with a more moderate compression/expansion response. The purpose of polymer X is to observe the effect of the F residues without the presence of the K residue of polymer VII. Finally, polymer XI combines all four variables: $(GVGIP)_{10}$ for the compression/expansion effect, GRGDSP for the cell attachment property, K for the enzymatic cross-linking potential and F residues for the effect that aromatic residues introduce on varying $T_t$ with pressure.

Example 5

Gene Construction, E. coli Transformation, Expression, Fermentation and Polymer Purification a. Construction of the Monomer Gene for Polymer XI (SEQ ID NO:60)

A strategy for construction the gene for polymer XI (SEQ ID NO:60), is presented here, as it is the most complex construction of the polymers being studied. This first requires the construction of the gene for $[(GVGVP)_2$ GKGVP GVGFP GFGFP]$_2$ (SEQ ID NO:62), encoding two repeats of the basic monomer gene for polymer VII (SEQ ID NO:54). This can be accomplished by joining two copies of the polymer VII basic monomer gene with a double-stranded synthetic oligonucleotide linker through the Hinf I and Kpn I sites located at the 3' and 5' ends of the gene, respectively, as shown in FIG. 10.

This will create a tandem gene repeat that has the PflM1 sites at the 5' and 3' ends, as needed for the subsequent gene concatanation. Also, the linker sequence is composed such that the Kpn I site is not restored upon ligation.

Next, the gene encoding the basic monomer gene for polymer XI (SEQ ID NO:60). This will be done using the above gene coding for $[(GVGVP)_2$ GKGVP GVGFP GFGFP]$_2$ (SEQ ID NO:62) in conjunction with the currently existing gene for $(GVGIP)_{10}$ (SEQ ID NO:56) and a linker encoding GVGVP GRGDSP (SEQ ID NOS: 20 and 46). The linker has cohesive ends that are compatible with the terminal PflM1 ends of both genes. However, upon ligation with the linker, the PflM1 sites are not restored, thereby maintaining only the PflM1 terminal sites for gene concatanation.

b. Concatamer Gene Construction for Polymer XI (SEQ ID NO:60) and E. coli Transformation The large amount of the catemer gene fragment was prepared by releasing the gene from plasmid pUC 118 by cleavage with PflM1, separation by electrophoresis through a polyacrylamide gel, followed by elution from the gel. The gene fragments were then concatanated by ligation through the PflM1 ends in the presence of double-stranded oligonucleotide adaptors. These adaptors terminate further polymer growth from the ends that they adjoin and provide the terminal restriction endonuclease sites required for cloning the gene polymer. In this case, the concatanation ligation product was digested with BamH1, mixed with BamH1- cleaved pUC118 and ligase, and was inserted into *E. coli* by transformation. Concatamer clones were analyzed by restriction endonuclease digestion and electrophoresis versus known size standards, including a concatamer ligation ladder.

c. *E. coli* Expression and Fermentation i. Expression

The pET plasmids (Novagen), such as pET-lld, were used for expression of the concatamer genes described above. For each of the concatamer genes, the gene fragment was released from the puC118 plasmid by cleavage with Nco1 and BamH1 and purified. It was then cloned into the pET plasmid at the Nco1 and BamH1 sites placing the initiator ATG codon of the concatamer gene immediately adjacent to the $T_7$ promoter and ribosome binding sequences.

Expression of the concatamer genes can then by analyzed following bench-scale culture and induction with or without the inducer isopropylthio-β-galactosidase ("IPTG"). Crude cell lysates of the cultures, taken pre- and post-induction, were electrophoresed on an SDS-PAGE and viewed following staining of the gels with $CuCl_2$. In addition, the proteins expressed from these small-scale cultures were purified following the procedures described below.

ii. Fermentation

Fermentations were performed using either Luria broth or Terrific Broth. Production of the protein-based polymers may be induced with the addition of the inducing agent IPTG. After the appropriate number of hours of growth, the culture was harvested by centrifugation and cells disrupted by means of a French press to release the cell contents.

d. Purification

The polymers can be conveniently purified from culture lysates using their inverse temperature transitional properties, as described above in Example 1d. For the Lys (K)-containing and GRGDSP-containing polymers, VII, VIII, IX and XI, variance of the pH is used to achieve the differential phase separation that is key to the purification process.

Example 6

Models for Determination of Efficacy a. Testing Using the Human Cadaver Spine

Ten whole lumbar spine segments (L1–L5), each with two selected disc sites, will be used to give a total of 20 disc sites for examination. Two different bioelastic compositions will be used so that there are 10 sites per composition. In addition, two different degrees of degeneration are to be considered so that there are 5 sites per composition for each of the two degrees of degeneration. A volume of approximately 2 mL of bioelastic polymer is o be placed in each disc following nucleotomy, requiring a total of about 25 g for each composition.

i. Specimen Preparation

Ten whole lumbar spine segments (L1–L5) will be obtained from fresh frozen human cadavers, reporting the age, sex and cause of death for each specimen. On arrival, the lumbar disc is thawed while immersed in a bath filled with saline solution (36 g NaCl per 4 L water) for eight hours. The segment is then dissected free from the soft musculature tissues with osseous and ligaments spinal structures kept intact. The spines are to be kept hydrated throughout the procedure.

ii. Pre-test Procedures for Evaluation of Disc Degeneration

The spinal segment is divided into 2 separate levels, L2–L3 and L4–L5 spinal functional units ("FSU") Radiographs of each lumbar section are taken, and used to verify the pathological condition of the vertebral bone with vertebrae exhibiting metastatic defects, pre-existing fractures and osteophytes formation rejected from the study. Lumbar FSU exhibiting arthritic facet joints may be treated separately in the analysis stage. The radiographs are also used for the measurements of the height of each intervertebral disc in accordance with the protocol suggested by Brinckmann, et al., *Clinical Biomechanics* 22(Suppl 1): 1–63 (1997).

The Bone Mineral Content ("BMC") and Bone Mineral Density ("BMD") of the spinal segments vertebral bodies are measured, for example using a DXA measurement device (Hologic QDR 2000+, Hologic Co., Waltham, Mass.). Vertebral bodies BMC has been reported to be strongly correlated with the viscoelastic properties of the intervertebral disc (Keller, et al., *J. Orthopedic Research* 5:467–478 (1987)). The measurement of the BMC and width adjusted BMD data may allow to partially account for the likely inter- and intra-subject variability in the specimens' mechanical properties.

The intervertebral discs for each of the spinal segments are then imaged, for example using an MRI device (SIEMENS Vision 1.5T, Siemens Co., CO), and the resulting images are graded in accordance with established clinical practices for the degradation and hydration states of the discs. The MRI data will also allow the assessment of the likely effects of both indicators on the viscoelastic properties of the intervertebral disc.

At the end of these procedures, the spine will be wrapped in saline soaked gauze and bagged, and frozen at −25° C. until the day of testing.

iii. Testing

Prior to testing, the spines will be thawed for 8 hours under refrigeration and for an additional 6 hours at room temperature. The superior and caudal end-plate sections of the top and bottom vertebral bodies, respectively, will be positioned, secured and embedded with PMMA inside circular aluminum mold rings. The FSU are positioned to ensure that the end caps are aligned parallel with the disc horizontal mid-plane. Throughout the procedure, the spine is kept hydrated.

(1) Specimen Mounting and Registration

The upper aluminum end cap will be secured to the upper actuator of a bi-axial hydraulic material testing system (Interlaken, U.S.A) with the segment center of rotation aligned with the long axis of the test system. The location of the center of rotation is found prior to the test (Liu, et al., *Spine* 13:1129–1134 (1988)).

The MacReflex Optical system (Qualisys, U.S.A) will be used to acquire the resultant motions along the FSU. Ten cylindrical markers having a diameter of 7 mm mounted on 3 mm pins will be positioned on the spinal specimen. The calibration, measurement and analysis of the FSU motions will be carried out using established laboratory protocols. The spine is kept hydrated throughout the procedures.

(2) Testing Procedures

The obtained discs, having been previously graded, will be divided into two groups. Disc grades I and II indicate moderate degeneration in one group and disc grades III and Iv indicate severe degeneration. Each of the following tests will be performed on the respective disc groups, before and after the bioelastic polymer has been injected into the disc space. For grade I and II discs, removal of the nucleus pulposus will be carried out using an established clinical procedures employing an arthroscope. The bioelastic polymer will be arthroscopically introduced into the nucleus pulposus cavity for both groups. A dye will be included with the polymer to indicate leakage of the polymer during the tests. The following test sequence was chosen so each test was designed as part of the conditioning cycle for the proceeding test. This sequence is aimed at keeping both the consecutive and cumulative damage to the FSU and in particular, the to intervertebral disc structures to a minimum.

(a) Anatomical Relationship Measurements

Under load control, three ramp type loading and un-loading compressive load cycles ranging 5–440 N at a rate of 25 N/sec, will be applied to condition the FSU. At the end of the conditioning cycles, the spatial relationships between the various markers are acquired using the MacReflex system to established reference values for the FSU spatial relationships. A compression load is applied to a value of 440 N at a rate of 25 N/sec, the load level held for a period of two seconds and subsequently removed using the same load rate until a load of 5 N is registered. The compressive load and axial displacement of the actuators is recorded using the material test transducers throughout the test with the markers position acquired for the duration of the test at one second intervals. The relative displacement of the upper vertebral body with respect to the lower vertebral body and the vertical change in the neural canal dimensions will be calculated using the MacReflex software.

(b) Creep Test

The spatial relationships between the various markers are acquired first using the MacReflex system. A compressive load is applied to the FSU at a rate of 25 N/sec until a value of 440 N is registered. The load is then maintained at a constant level for a duration of 30 minutes. At the end of this period, the load is removed at a similar rate until a compression load of 2 N is registered. The disc is then allowed to recover for 30 minutes. The compressive load, actuator axial displacement and marker position as a function of time will be recorded for the duration of the test. A three element Kelvin model will be used to estimate the rheological parameters describing the viscoelastic behavior of the disc, namely the elastic ($E_1$) and viscous ($E_2$) stiffness and viscosity ($\eta$), in accordance with the protocol proposed by Keller, et al., supra.

(c) Dynamic Tests

Under load control, three ramp type loading and un-loading compressive load cycles ranging 5–440 N at a rate of 25 N/sec, will be applied to the FSU in a similar manner to the first test procedure. The FSU will then be subjected to axial compression sinusoidal forces with frequencies ranging from 0.5–40 Hz. The test is carried out using varying pre-load magnitude namely, 60, 200, 340, 480 and 620 N with the load amplitude kept to a value of 20N to maintain a near linear response. The disc compliance data is then collected using a frequency sweep technique with the data recorded at intervals of 2–3 Hz at frequencies distant from the segment resonant frequency and in 0.5 Hz intervals at frequencies approaching the resonant frequency. The applied force, frequency of application and the specimen response amplitude will be recorded using the material test system transducers. The intervertebral disc damping, hysteresis, dynamic stiffness and energy dissipation, will be estimated from the frequency versus amplitude curve using standard techniques (Clough, et al., *Dynamic Structures* $2^{nd}$ edition, McGraw Hill, 1993).

(d) Flexibility Test

The motion segment will be loaded in flexion and extension using couple moments in accordance with the protocol proposed by Panjabi, et al., *Spine* 8(8):857–865 (1983). For this purpose, a flexion/extension jig is employed to load the specimen under a constant moment with the resulting deformations measured using the MacReflex system. The load-deflection curves are then used to establish the segment neutral and elastic zones as indicators for changes in segmental stability.

iv. Analysis

The interactions likely to occur between the various viscoelastic and dynamic variables and the effect of co-variants on the responses of the disc under the different tests, are then assessed using exploratory and graphic analysis techniques.

b. In vivo Animal Model

Degenerated intervertebral discs can be created by performing percutaneous nucleotomies on the micro-pig. Under general anesthesia, a posterolateral percutaneous approach would be used to perform a nucleotomy. The instrumentation for the percutaneous nucleotomy is currently available for human clinical use. The arthroscopic portal is approximately 3 mm in diameter. At one level, the tested polymer would be inserted through the arthroscopic device to regenerate the nucleus. The other level would be retained, without polymer, as an in vivo control. The site of insertion of the polymer can be randomized to prevent any skewing of results relative to anatomic level. The animals would be subjected to MRI studies at 4 and 8 weeks post-surgery to assess the status of the discs. At three months, the animals would be sacrificed for histologic evaluation of the motion segments involved.

BRIEF DESCRIPTION OF THE SEQUENCE LISTING

SEQ ID NO:1 depicts a 5' oligomer construct for producing polymer units of SEQ ID NO:9.

SEQ ID NO:2 depicts a 3' oligomer construct for producing polymer units of SEQ ID NO:10 and polymer II (SEQ ID NO:36).

SEQ ID NO:3 and 4 depict 3' oligomer constructs for producing polymer units of SEQ ID NO:11.

SEQ ID NO:5 depicts a 3' oligomer construct for producing polymer units of SEQ ID No. 12 and polymer I (SEQ ID NO:35).

SEQ ID NO:6 is a synthetic gene sequence coding for SEQ ID No. 13 and polymer III (SEQ ID NO:37).

SEQ ID NO:7 is a synthetic gene sequence coding for SEQ ID No. 14 and polymer IV (SEQ ID NO:38).

SEQ ID NO:8 is a synthetic gene sequence coding for SEQ ID No. 15 and polymer V (SEQ ID NO:39).

SEQ ID NO:9 is the protein sequence of a tetrameric elastomer.

SEQ ID NO:10 is the protein sequence of a lysine and phenylalanine containing elastomer.

SEQ ID NO:11 is the protein sequence of GRGDSP cell adhesion containing sequence.

SEQ ID NO:12 is the protein sequence of a lysine containing elastomer.

SEQ ID NO:13 is the protein sequence of a GRGDSP containing elastomer.

SEQ ID NO:14 is the protein sequence of an alanine containing elastomer.

SEQ ID NO:15 is the protein sequence of a glutamic acid containing elastomer.

SEQ ID NO:16 and 17 are tetrapeptide and pentapeptide monomers, respectively.

SEQ ID NO:18 is a polypentapeptide elastomer.

SEQ ID NO:19 is a pentapeptide monomer.

SEQ ID NO:20 is a polymer comprised of pentapeptide monomers.

SEQ ID NO:21 is the protein sequence of a GRGDSP containing elastomer.

SEQ ID NO:22 is the protein sequence of a glutamic acid containing elastomer.

SEQ ID NO:23 and 24 are oligonucleotides for producing a phenylalanine containing elastomer (SEQ ID NO:9).

SEQ ID NO:25 is the protein sequence of a lysine and phenylalanine containing elastomer.

SEQ ID NO:26 and 27 are oligonucleotides for producing a lysine and phenylalanine containing elastomer (SEQ ID NO:10).

SEQ ID NO:28 is the protein sequence of the cell adhesion sequence.

SEQ ID NO:29 is the protein sequence of an elastomer comprised of pentapeptide monomers.

SEQ ID NOS:30, 31, 32 and 33 are synthetic gene sequences coding for adapter oligomers used to clone concatamers of the various elastomer genes.

SEQ ID NO:34 is the protein sequence of a GRGDSP containing elastomer.

SEQ ID NO:35 is the protein sequence of polymer I, which contains Lys.

SEQ ID NO:36 is the protein sequence of polymer II, which contains Phe and Lys.

SEQ ID NO:37 is the protein sequence of polymer III, which contains a cell adhesion sequence.

SEQ ID NO:38 is the protein sequence of polymer IV

SEQ ID NO:39 is the protein sequence of polymer V, which contains Glu.

SEQ ID NO:40 is a polypentapeptide elastomer.

SEQ ID NOS:41 and 42 are tetrapeptide monomers.

SEQ ID NOS:43, 44 and 45 are pentapeptide monomers.

SEQ ID NO:46 is the GRGDSP cell attachment sequence.

SEQ ID NO:47 is GVGVAP.

SEQ ID NOS:48 and 49 are pentapeptide monomers.

SEQ ID NO:50 is a tetrapeptide monomer.

SEQ ID NO:51 is a pentapeptide monomer.

SEQ ID NO:52 is VGVAPG.

SEQ ID NO:53 is the protein sequence of a GRGDSP containing elastomer.

SEQ ID NOS:54, 55 and 56 are protein sequences of elastomers comprised of pentapeptide monomers, where SEQ ID NO:54 is polymer VII and SEQ ID NO:56 is polymer VI.

SEQ ID NOS:57 and 58 are protein sequences of GRGDSP containing elastomers, polymers VIII and IX, respectively.

SEQ ID NO:59 is the protein sequence of an elastomer comprised of pentapeptide monomers, polymer X.

SEQ ID NO:60 is the protein sequence of a GRGDSP containing elastomer, polymer XI.

SEQ ID NO:61 is the protein sequence of an elastomer comprised of pentapeptide monomers.

SEQ ID NO:62 is the protein sequence of a fragment of polymer XI.

SEQ ID NOS:63 and 64 are synthetic gene sequences coding for adapter oligomers used to clone the gene for polymer XI.

SEQ ID NO:65 is the protein sequence of a fragment of polymer XI.

All publications and patent applications mentioned in this specification are herein incorporated by reference to the same extent as if each individual publication or patent application was specifically and individually indicated to be incorporated by reference at the location where cited.

The invention now being fully described, it will be apparent to one of ordinary skill in the art that many changes and modifications can be made thereto without departing from the spirit or scope of the invention.

---

What is claimed is:

1. A method for tissue restoration of intervertebral discs in a mammal, said method comprising: injecting a polymer into the depleted nucleus pulposus site, which has a site temperature, said polymer comprising repeating peptide monomeric units selected from the group consisting of nonapeptide, pentapeptide and tetrapeptide monomeric units, wherein said monomeric units form a series of β-turns separated by dynamic bridging segments suspended between said β-turns, wherein said polymer has an inverse temperature transition $T_t$ less than said site temperature, and wherein said polymer is injected as a water solution at coacervate concentration in the substantial absence of additional water and swells to increase the pressure within said disc.

2. The method of claim 1 wherein said coacervate has an elastic modulus at said site of $5 \times 10^4$ to $5 \times 10^6$ N/m².

3. The method of claim 1 wherein said polymer is cross-linked.

4. The method of claim 1 wherein said polymer is a copolymer formed from one of said monomeric units and a second peptide unit containing 1–100 amino acids.

5. The method of claim 4 wherein said second peptide unit contains 1–20 amino acids.

6. The method of claim 5 wherein said second peptide unit comprises the cell attachment sequence, GRGDSP (SEQ ID NO:46).

7. The method of claim 5 wherein said second peptide unit comprises GVGVAP (SEQ ID NO:47) or VGVAPG (SEQ ID NO:52).

8. The method of claim 4 wherein said second peptide unit comprises a cell attachment sequence selected from the group consisting of Type-III domains of fibronectin, vitronectin, tenascin, titin and other related cell attachment proteins.

9. The method of claim 1 wherein said polymer comprises a block or random copolymer comprising at least two of said monomeric units.

10. The method of claim 1 wherein said polymer comprises an elastomeric polytetrapeptide or polypentapeptide.

11. The method of claim 10 wherein said polymer comprises tetrapeptide units selected from the group consisting of VPGG (SEQ ID NO:16), GGVP (SEQ ID NO:41); GGFP (SEQ ID NO:42) and GGAP (SEQ ID NO:50).

12. The method of claim 10 wherein said polymer comprises pentapeptide units selected from the group consisting of VPGVG (SEQ ID NO:17), GVGVP (SEQ ID NO:20), GKGVP (SEQ ID NO:43), GVGFP (SEQ ID NO:44), GFGFP (SEQ ID NO:45), GEGVP (SEQ ID NO:48), GFGVP (SEQ ID NO:49) and (GVGIP) (SEQ ID NO:51).

13. The method of claim 1 wherein said polymer comprises at least one pentapeptide unit of (GVGIP) (SEQ ID NO:51).

14. The method of claim 1 wherein at least one of said monomeric units contains an aromatic residue.

15. The method of claim 14 wherein said aromatic residue is phenylalanine.

16. The method of claim 1 wherein said polymer is a copolymer comprised of tetrapeptide and pentapeptide units.

17. The method of claim 1 wherein said polymer comprises a plastic polypeptide.

18. The method of claim 1 wherein said polymer is contained within a pharmaceutically acceptable liquid carrier, which further comprises one or more biologically active factors to aid in the healing or regrowth of natural tissue.

19. A method for tissue restoration of intervertebral discs in a mammal, said method comprising to step of injecting a polymer into the depleted nucleus pulposus site, which has a site temperature ($T_s$), said polymer comprising repeating peptide monomeric units selected from the group consisting of pentapeptide and tetrapeptide monomeric units, alone or in combination, wherein said monomeric units form a series of β-turns separated by dynamic bridging segments suspended between said β-turns, and wherein (i) said polymer has an inverse temperature transition $T_t$ less than $T_s$, (ii) said polymer is injected as a water solution at coacervate concentration in the substantial absence of additional water and swells to increase the pressure within said disc, and (iii) said coacervate has a shear modulus at $T_s$ of $5 \times 10^4$ to $5 \times 10^6$ N/m².

20. The method of claim 19 wherein said polymer is cross-linked.

21. The method of claim 19 wherein said polymer is a copolymer formed from said monomeric units and a second peptide unit containing 1–20 amino acids.

22. The method of claim 21 wherein said second peptide unit is selected from the group consisting of GRGDSP (SEQ ID NO:46), GVGVAP (SEQ ID NO:47) and VGVAPG (SEQ ID NO:52).

23. The method of claim 19 wherein said polymer comprises a block or random copolymer comprising at least two different monomeric units.

24. The method of claim 19 wherein said polymer comprises an elastomeric polytetrapeptide or polypentapeptide.

25. The method of claim 24 wherein said polymer comprises tetrapeptide units selected from the group consisting of VPGG (SEQ ID NO:16), GGVP (SEQ ID NO:41); GGFP (SEQ ID NO:42) and GGAP (SEQ ID NO:50).

26. The method of claim 24 wherein said polymer comprises pentapeptide units selected from the group consisting of VPGVG (SEQ ID NO:17), GVGVP (SEQ ID NO:20), GKGVP (SEQ ID NO:43), GVGFP (SEQ ID NO:44), GFGFP (SEQ ID NO:45), GEGVP (SEQ ID NO:48), GFGVP (SEQ ID NO:49) and (GVGIP) (SEQ ID NO:51).

27. The method of claim 26 wherein said polymer comprises at least one pentapeptide unit of (GVGIP) (SEQ ID NO:51).

28. The method of claim 19 wherein at least one of said monomeric units contains a phenylalanine residue.

29. The method of claim 19 wherein said polymer is a copolymer comprised of tetrapeptide and pentapeptide units.

30. The method of claim 19 wherein said polymer is contained within a pharmaceutically acceptable liquid carrier, which further comprises one or more biologically active factors to aid in the healing or regrowth of natural tissue.

* * * * *